US007199221B2

(12) United States Patent
Walke et al.

(10) Patent No.: US 7,199,221 B2
(45) Date of Patent: Apr. 3, 2007

(54) HUMAN SEMAPHORIN HOMOLOGS AND POLYNUCLEOTIDES ENCODING THE SAME

(75) Inventors: D. Wade Walke, Spring, TX (US); Xiaoming Wang, Northbrook, IL (US); John Scoville, Houston, TX (US); C. Alexander Turner, Jr., The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 510 days.

(21) Appl. No.: 10/833,509

(22) Filed: Apr. 28, 2004

(65) Prior Publication Data

US 2005/0054040 A1 Mar. 10, 2005

Related U.S. Application Data

(63) Continuation of application No. 09/854,845, filed on May 14, 2001, now Pat. No. 6,750,054.

(60) Provisional application No. 60/205,274, filed on May 18, 2000, provisional application No. 60/208,893, filed on Jun. 2, 2000.

(51) Int. Cl.
*C07K 14/435* (2006.01)
(52) U.S. Cl. .............................. 530/350; 514/2; 514/12
(58) Field of Classification Search ...................... None
See application file for complete search history.

(56) References Cited

U.S. PATENT DOCUMENTS

| 4,215,051 A | 7/1980 | Schroeder et al. |
| 4,376,110 A | 3/1983 | David et al. |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,494,595 A | 2/1996 | Nieh |
| 5,556,752 A | 9/1996 | Lockhart et al. |
| 5,700,637 A | 12/1997 | Southern |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 5,981,222 A | 11/1999 | Jacobs et al. |
| 6,013,781 A | 1/2000 | Goodman et al. |
| 6,075,181 A | 6/2000 | Kucherlapati et al. |
| 6,110,490 A | 8/2000 | Thierry |
| 6,150,584 A | 11/2000 | Kucherlapati et al. |

FOREIGN PATENT DOCUMENTS

| WO | WO 00/11015 A1 | 3/2000 |
| WO | WO 01/32707 A1 | 5/2001 |

OTHER PUBLICATIONS

Tessier-Lavigne et al. *Science*, vol. 274, pp. 1123-1133.*
Nagase et al. *DNA Res.*, vol. 7, pp. 143-150, 2000.*
Bird et al, 1988, "Single-Chain Antigen-Binding Proteins", Science 242:423-426.
Bitter et al, 1987, "Expression and Secretion Vectors for Yeast", Methods in Enzymology 153:516-544.
Colbere-Garapin et al, 1981, "A New Dominant Hybrid Selective Marker for Higher Eukaryotic Cells", J. Mol. Biol. 150:1-14.
Gautier et al, 1987, "α-DNA IV:α-anomeric and β-anomeric tetrathymidylates covalently linked to intercalating oxazolopyridocarbazole. Synthesis, physiochemical properties and poly (rA) binding", Nucleic Acids Research 15(16):6625-6641.
Gordon, 1989, "Transgenic Animals", International Review of Cytology, 115:171-229.
Greenspan et al, 1993, "Idiotypes: structure and immunogenicity", FASEB Journal 7:437-444.
Gu et al, 1994, "Deletion of a DNA Polymerase β Gene Segment in T Cells Using Cell Type-Specific Gene Targeting", Science 265:103-106.
Huse et al, 1989, "Generation of a Large Combinatorial Library of the Immunoglobulin Repertoire in Phage Lambda", Science 246:1275-1281.
Huston et al, 1988, "Protein engineering of antibody binding sites: Recovery of specific activity in an anti-digoxin single-chain FV analogue produced in *Escherichia coli*", Proc. Natl. Acad. Sci. USA 85:5879-5883.
Inoue et al, 1987, "Sequence-dependent hydrolysis of RNA using modified oligonucleotide splints and R Nase H", FEBS Letters 215(2):327-330.
Inoue et al, 1987, "Synthesis and hybridization studies on two complementary nona(2'-O-methyl)ribonucleotides", Nucleic Acids Research 15(15):6131-6149.
Inouye & Inouye, 1985, "Up-promoter mutations in the Ipp gene of *Escherichia coli*", Nucleic Acids Research 13(9):3101-3110.
Janknecht et al, 1991, "Rapid and efficient purification of native histidine-tagged protein expressed by recombinant vaccinia virus", PNAS 88:8972-8976.
Kohler & Milstein, 1975, "Continuous cultures of fused cells secreting antibody of predefined specificity", Nature 256:495-497.
Lakso et al, 1992, "Targeted oncogene activation by site-specific recombination in transgenic mice", Proc. Natl. Acad. Sci. USA 89:6232-6236.
Lam et al, 1991, "A new type of synthetic peptide library for identifying ligand-binding activity", Nature 354:82-86.
Lavitrano et al, 1989, "Sperm Cells ad Vectors for Introducing Froeign DNA into Eggs: Genetic Transformation of Mice", Cell 57:717-723.

(Continued)

*Primary Examiner*—Janet L. Andres
*Assistant Examiner*—Stephen Gucker

(57) ABSTRACT

Novel human polynucleotide and polypeptide sequences are disclosed that can be used in therapeutic, diagnostic, and pharmacogenomic applications.

10 Claims, No Drawings

OTHER PUBLICATIONS

Lo, 1983, "Transformation by Iontophoretic Microinjection of DNA: Multiple Integrations without Tandem Insertions", Mol. & Cell. Biology 3(10):1803-1814.

Logan et al, 1984, "Adenovirus tripartite leader sequence enhances translation of mRNAs late after infection", Proc. Natl. Acad. Sci. USA 81:3655-3659.

Lowy et al, 1980, "Isolation of Transforming DNA: Cloning the Hamster aprt Gene", Cell 22:817-823.

Morrison et al, 1984, "Chimeric human antibody molecules: Mouse antigen-binding domains with human constant region domains", Proc. Natl. Acad. Sci. USA 81:6851-6855.

Mulligan & Berg, 1981, "Selection for animal cells that express the *Escherichia coli* gene coding for xanthine-guanine phosphoribosyltransferase", Proc. Natl. Acad. Sci. USA 78(4):2072-2076.

Neuberger et al, 1984, "Recombinant antibodies possessing novel effector functions", Nature 312:604-608.

Nisonoff, 1991, "Idiotypes: Concepts and Applications", J. of Immunology 147:2429-2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527-1531.

Ruther et al, 1983, "Easy identification of cDNA clones", EMBO Journal 2(10):1791-1794.

Santerre et al, 1984, "Expression of prokaryotic genes for hygromycin B and G418 resistance as dominant-selection markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Smith et al, 1983, "Molecular Engineering of the Autographa californica Nuclear Polyhedrosis Virus Genome: Deletion Mutations within the Polyhedrin Gene", J. Virol. 46(2):584-593.

Stein et al, 1988, "Physiochemical properties of phosphorothioate oligodeoxynucleotides", Nucleic Acids Research 16(8):3209-3221.

Szybalska & Szybalski, 1962, "Genetics of Human Cell Lines, IV. DNA-Mediated Heritable Transformation of a Biochemical Trait", Proc. Natl. Acad. Sci. USA 48:2026-2034.

Takeda et al, 1985, "Construction of chimaeric processed immunoglobulin genes containing mouse variable and human constant region sequences", Nature 314:452-454.

Thompson et al, 1989, "Germ Line Transmission and Expression of a Corrected HPRT Gene Produced by Gene Targeting in Embryonic Stem Cells", Cell 56:313-321.

Van Der Putten et al, 1985, "Efficient insertion of genes into the mouse germ line via retroviral vectors", Proc. Natl. Acad. Sci. USA 82:6148-6152.

Van Heeke et al, 1989, "Expression of Human Asparagine Synthetase in *Escherichia coli*", J. Biol. Chemistry 264(10):5503-5509.

Ward et al, 1989, "Binding activities of a repertoire of single immunoglobulin variable domains secreted from *Escherichia coli*", Nature 341:544-546.

Wigler et al, 1977, "Transfer of Purified Herpes Virus Thymidine Kinase Gene to Cultured Mouse Cells", Cell 11:223-232.

Wigler et al, 1980, "Transformation of mammalian cells with an amplifiable dominant-acting gene", Proc. Natl. Acad. Sci. USA 77(6):3567-3570.

Adams et al., "A Novel Class of Murine Semaphorins with Homology to Thrombospondinis Differentially Expressed during early Embryogenesis," Mechanisms of Development, Elsevier Science Ireland Ltd., IE, vol. 57, 1996, pp. 33-45, XP000996385, ISSN: 0925-4773.

Database EMBL 'Online! Adams et al., "*M.musculus* mRNA for semaphorin G," Jun. 30, 1996, Database accession No. X97818, Q60519, XP002219588.

Database EMBL 'Online! Ohara, et al., "*Homo sapiens* mRNA for KIAA1445 protein, partial cds.," May 23, 2000, Database accession No. AB040878, Q9P283, XP002219589.

Simmons et al., "Molecular cloning and mapping of human semaphorin F from the Cri-du-chat candidate interval," Biochemical and Biophysical Research Communications, vol. 242, No. 3, Jan. 26, 1998, pp. 685-691, XP002219587, ISSN: 0006-291X.

International Search Report, International Application No. PCT/US01/15489, May 14, 2001.

* cited by examiner

SEQUENCE LISTING

<160> NUMBER OF SEQ ID NOS: 50

<210> SEQ ID NO 1
<211> LENGTH: 3150
<212> TYPE: DNA
<213> ORGANISM: homo sapiens

<400> SEQUENCE: 1

```
atgacggtgg ttaatccaca agacctgcag ccgtgggtct ctaacttcac ctaccctgga      60
gcccgggatt tctcccagct ggctttggac ccctccgggr accagctcat cgtgggagcc     120
```

```
aggaactacc tcttcagact cagccttgcc aatgtctctc ttcttcaggc cacagagtgg      180
gcctccagtg aggacacgcg ccgctcctgc caaagcaaag ggaagactga ggaggagtgt      240
cagaactacg tgcgagtcct gatcgtcgcc ggccggaagg tgttcatgtg tggaaccaat      300
gcctttcccc ccatgtgcac cagcagacag gtggggaacc tcagccggac tattgagaag      360
atcaatggtg tggcccgctg cccctatgac ccacgccaca actccacagc tgtcatctcc      420
tcccaggggg agctctatgc agccacggtc atcgacttct caggtcggga ccctgccatc      480
taccgcagcc tgggcagtgg gccaccgctt cgcactgccc aatataactc caagtggctt      540
aatgagccaa acttcgtggc agcctatgat attgggctgt tgcatacttc ttcctgcgg      600 gagaacgcag tggagcacga ctgtggacgc accgtgtact ctcgcgtggc ccgcgtgtgc      660
aagaatgacg tgggggggccg attcctgctg gaggacacat ggaccacatt catgaaggcc      720
cggctcaact gctcccgccc gggcgaggtc cccttctact ataacgagct gcagagtgcc      780
ttccacttgc crgagcagga cctcatctat ggagttttca caaccaacgt aaacagcaty      840
gcggcttctg ctgtctgcgc cttcaacctc agtgctatct cccaggcttt caatggccca      900
tttcgctacc aggagaaccc cagggctgcc tggctcccca tagccaaccc catccccaat      960
ttccagtgtg gcaccctgcc tgagaccggt cccaacgaga acctgacgga gcgcagcctg     1020
caggacgcgc agcgcctctt cctgatgagc gaggccgtgc agccggtgac acccgagccc     1080
tgtgtcaccc aggacagcgt gcgcttctca cacctcgtgg tggacctggt gcaggctaaa     1140
gacacgctct accatgtact ctacattggc accgagtcgg gcaccatcct gaaggcgctg     1200
tccacggcga gccgcagcct ccacggctgc tacctggagg agctgcacgt gctgcccccc     1260
gggcgccgcg agcccctgcg cagcctgcgc atcctgcaca cgcccgcgc gctcttcgtg     1320 gggctgagag acggcgtcct gcgggtccca ctggagaggt gcgccgccta ccgcagccag     1380
ggggcatgcc tgggggcccg ggacccgtac tgtggctggg acgggaagca gcaacgttgc     1440
agcacactcg aggacagctc caacatgagc ctctggaccc agaacatcac cgcctgtcct    1500
gtgcggaatg tgacacggga tgggggcttc ggcccatggt caccatggca accatgtgag     1560
cacttggatg gggacaactc aggctcttgc ctgtgtcgag ctcgatcctg tgattcccct     1620 cgacccgct gtgggggcct tgactgcctg gggccagcca tccacatcgc caactgctcc      1680
aggaatgggg cgtggacccc gtggtcatcg tgggcgctgt gcagcacgtc ctgtggcatc     1740
ggcttccagg tccgccagcg aagttgcagc aaccctgctc cccgccacgg gggccgcatc     1800
tgcgtgggca agagccggga ggaacggttc tgtaatgaga cacgccttg cccggtgccc     1860 atcttctggg cttcctgggg ctcctggagc aagtgcagca gcaactgtgg aggggggcatg   1920 cagtcgcggc gtcgggcctg cgagaacggc aactcctgcc tgggctgcgg cgtggagttc     1980
aagacgtgca accccgaggg ctgccccgaa gtgcggcgca acacccctg gacgccgtgg     2040 ctgcccgtga acgtgacgca gggcggggca cggcaggagc agcggttccg cttcacctgc     2100 cgcgcgccc ttgcagaccc gcacggcctg cagttcggca ggagaaggac cgagacgagg     2160
acctgtcccg cggacggctc cggctcctgc gacaccgacg ccctggtgga ggacctcctg     2220
cgcagcggga gcacctcccc gcacacggtg agcggggct gggccgcctg gggcccgtgg     2280
tcgtcctgct cccgggactg cgagctgggc ttccgcgtcc gcaagagaac gtgcactaac     2340
ccggagcccc gcaacggggg cctgccctgc gtgggcgatg ctgccgagta ccaggactgc     2400 aaccccagg cttgcccagt tcgggtgctt tggtcctgct ggacctcatg gtctccatgc     2460
tcagcttcct gtggtggggg tcactatcaa cgcacccgtt cctgcaccag ccccgcaccc    2520
```

-continued

```
tccccaggtg aggacatctg tctcgggctg cacacggagg aggcactatg tgccacacag    2580
gcctgcccag aaggctggtc gccctggtct gagtggagta agtgcactga cgacggagcc    2640
cagagccgaa gccggcactg tgaggagctc ctcccagggt ccagcgcctg tgctggaaac    2700
agcagccaga gccgcccctg ccctacagc gagattccg tcatcctgcc agcctccagc     2760
atggaggagg ccaccggctg tgcagggttc aatctcatcc acttggtggc cacgggcatc    2820
tcctgcttct tgggctctgg gctcctgacc ctagcagtgt acctgtcttg ccagcactgc    2880
cagcgtcagt cccaggagtc cacactggtc catcctgcca cccccaacca tttgcactac    2940
aagggcggag gcaccccgaa gaatgaaaag tacacaccca tggaattcaa gaccctgaac    3000
aagaataact tgatccctga tgacagagcc aacttctacc cattgcagca gaccaatgtg    3060
tacacgacta cttactaccc aagcccctg aacaaacaca gcttccggcc cgaggcctca    3120
cctggacaac ggtgcttccc caacagctga                                    3150
```

<210> SEQ ID NO 2
<211> LENGTH: 1049
<212> TYPE: PRT
<213> ORGANISM: homo sapiens

<400> SEQUENCE: 2

```
Met Thr Val Val Asn Pro Gln Asp Leu Gln Pro Trp Val Ser Asn Phe
  1               5                  10                  15

Thr Tyr Pro Gly Ala Arg Asp Phe Ser Gln Leu Ala Leu Asp Pro Ser
                 20                  25                  30

Gly Asn Gln Leu Ile Val Gly Ala Arg Asn Tyr Leu Phe Arg Leu Ser
             35                  40                  45

Leu Ala Asn Val Ser Leu Leu Gln Ala Thr Glu Trp Ala Ser Ser Glu
 50                  55                  60

Asp Thr Arg Arg Ser Cys Gln Ser Lys Gly Lys Thr Glu Glu Glu Cys
 65                  70                  75                  80

Gln Asn Tyr Val Arg Val Leu Ile Val Ala Gly Arg Lys Val Phe Met
                 85                  90                  95

Cys Gly Thr Asn Ala Phe Ser Pro Met Cys Thr Ser Arg Gln Val Gly
                100                 105                 110

Asn Leu Ser Arg Thr Ile Glu Lys Ile Asn Gly Val Ala Arg Cys Pro
            115                 120                 125

Tyr Asp Pro Arg His Asn Ser Thr Ala Val Ile Ser Ser Gln Gly Glu
        130                 135                 140

Leu Tyr Ala Ala Thr Val Ile Asp Phe Ser Gly Arg Asp Pro Ala Ile
145                 150                 155                 160

Tyr Arg Ser Leu Gly Ser Gly Pro Pro Leu Arg Thr Ala Gln Tyr Asn
                165                 170                 175

Ser Lys Trp Leu Asn Glu Pro Asn Phe Val Ala Ala Tyr Asp Ile Gly
            180                 185                 190

Leu Phe Ala Tyr Phe Phe Leu Arg Glu Asn Ala Val Glu His Asp Cys
        195                 200                 205

Gly Arg Thr Val Tyr Ser Arg Val Ala Arg Val Cys Lys Asn Asp Val
    210                 215                 220

Gly Gly Arg Phe Leu Leu Glu Asp Thr Trp Thr Thr Phe Met Lys Ala
225                 230                 235                 240

Arg Leu Asn Cys Ser Arg Pro Gly Glu Val Pro Phe Tyr Tyr Asn Glu
                245                 250                 255
```

-continued

Leu Gln Ser Ala Phe His Leu Pro Glu Gln Asp Leu Ile Tyr Gly Val
             260                 265                 270

Phe Thr Thr Asn Val Asn Ser Ile Ala Ala Ser Ala Val Cys Ala Phe
         275                 280                 285

Asn Leu Ser Ala Ile Ser Gln Ala Phe Asn Gly Pro Phe Arg Tyr Gln
         290                 295                 300

Glu Asn Pro Arg Ala Ala Trp Leu Pro Ile Ala Asn Pro Ile Pro Asn
305                 310                 315                 320

Phe Gln Cys Gly Thr Leu Pro Glu Thr Gly Pro Asn Glu Asn Leu Thr
             325                 330                 335

Glu Arg Ser Leu Gln Asp Ala Gln Arg Leu Phe Leu Met Ser Glu Ala
             340                 345                 350

Val Gln Pro Val Thr Pro Glu Pro Cys Val Thr Gln Asp Ser Val Arg
             355                 360                 365

Phe Ser His Leu Val Val Asp Leu Val Gln Ala Lys Asp Thr Leu Tyr
             370                 375                 380

His Val Leu Tyr Ile Gly Thr Glu Ser Gly Thr Ile Leu Lys Ala Leu
385                 390                 395                 400

Ser Thr Ala Ser Arg Ser Leu His Gly Cys Tyr Leu Glu Glu Leu His
             405                 410                 415

Val Leu Pro Pro Gly Arg Arg Glu Pro Leu Arg Ser Leu Arg Ile Leu
             420                 425                 430

His Ser Ala Arg Ala Leu Phe Val Gly Leu Arg Asp Gly Val Leu Arg
             435                 440                 445

Val Pro Leu Glu Arg Cys Ala Ala Tyr Arg Ser Gln Gly Ala Cys Leu
             450                 455                 460

Gly Ala Arg Asp Pro Tyr Cys Gly Trp Asp Gly Lys Gln Gln Arg Cys
465                 470                 475                 480

Ser Thr Leu Glu Asp Ser Ser Asn Met Ser Leu Trp Thr Gln Asn Ile
             485                 490                 495

Thr Ala Cys Pro Val Arg Asn Val Thr Arg Asp Gly Gly Phe Gly Pro
             500                 505                 510

Trp Ser Pro Trp Gln Pro Cys Glu His Leu Asp Gly Asp Asn Ser Gly
             515                 520                 525

Ser Cys Leu Cys Arg Ala Arg Ser Cys Asp Ser Pro Arg Pro Arg Cys
             530                 535                 540

Gly Gly Leu Asp Cys Leu Gly Pro Ala Ile His Ile Ala Asn Cys Ser
545                 550                 555                 560

Arg Asn Gly Ala Trp Thr Pro Trp Ser Ser Trp Ala Leu Cys Ser Thr
             565                 570                 575

Ser Cys Gly Ile Gly Phe Gln Val Arg Gln Arg Ser Cys Ser Asn Pro
             580                 585                 590

Ala Pro Arg His Gly Gly Arg Ile Cys Val Gly Lys Ser Arg Glu Glu
             595                 600                 605

Arg Phe Cys Asn Glu Asn Thr Pro Cys Pro Val Pro Ile Phe Trp Ala
             610                 615                 620

Ser Trp Gly Ser Trp Ser Lys Cys Ser Ser Asn Cys Gly Gly Gly Met
625                 630                 635                 640

Gln Ser Arg Arg Arg Ala Cys Glu Asn Gly Asn Ser Cys Leu Gly Cys
             645                 650                 655

Gly Val Glu Phe Lys Thr Cys Asn Pro Glu Gly Cys Pro Glu Val Arg
             660                 665                 670

-continued

Arg Asn Thr Pro Trp Thr Pro Trp Leu Pro Val Asn Val Thr Gln Gly
    675                 680                 685

Gly Ala Arg Gln Glu Gln Arg Phe Arg Phe Thr Cys Arg Ala Pro Leu
    690                 695                 700

Ala Asp Pro His Gly Leu Gln Phe Gly Arg Arg Thr Glu Thr Arg
705                 710                 715                 720

Thr Cys Pro Ala Asp Gly Ser Gly Ser Cys Asp Thr Asp Ala Leu Val
                725                 730                 735

Glu Asp Leu Leu Arg Ser Gly Ser Thr Ser Pro His Thr Val Ser Gly
                740                 745                 750

Gly Trp Ala Ala Trp Gly Pro Trp Ser Ser Cys Ser Arg Asp Cys Glu
                755                 760                 765

Leu Gly Phe Arg Val Arg Lys Arg Thr Cys Thr Asn Pro Glu Pro Arg
    770                 775                 780

Asn Gly Gly Leu Pro Cys Val Gly Asp Ala Ala Glu Tyr Gln Asp Cys
785                 790                 795                 800

Asn Pro Gln Ala Cys Pro Val Arg Gly Ala Trp Ser Cys Trp Thr Ser
                805                 810                 815

Trp Ser Pro Cys Ser Ala Ser Cys Gly Gly His Tyr Gln Arg Thr
                820                 825                 830

Arg Ser Cys Thr Ser Pro Ala Pro Ser Pro Gly Glu Asp Ile Cys Leu
                835                 840                 845

Gly Leu His Thr Glu Glu Ala Leu Cys Ala Thr Gln Ala Cys Pro Glu
    850                 855                 860

Gly Trp Ser Pro Trp Ser Glu Trp Ser Lys Cys Thr Asp Asp Gly Ala
865                 870                 875                 880

Gln Ser Arg Ser Arg His Cys Glu Glu Leu Leu Pro Gly Ser Ser Ala
                885                 890                 895

Cys Ala Gly Asn Ser Ser Gln Ser Arg Pro Cys Pro Tyr Ser Glu Ile
                900                 905                 910

Pro Val Ile Leu Pro Ala Ser Ser Met Glu Glu Ala Thr Gly Cys Ala
    915                 920                 925

Gly Phe Asn Leu Ile His Leu Val Ala Thr Gly Ile Ser Cys Phe Leu
    930                 935                 940

Gly Ser Gly Leu Leu Thr Leu Ala Val Tyr Leu Ser Cys Gln His Cys
945                 950                 955                 960

Gln Arg Gln Ser Gln Glu Ser Thr Leu Val His Pro Ala Thr Pro Asn
                965                 970                 975

His Leu His Tyr Lys Gly Gly Gly Thr Pro Lys Asn Glu Lys Tyr Thr
                980                 985                 990

Pro Met Glu Phe Lys Thr Leu Asn Lys Asn Asn Leu Ile Pro Asp Asp
                995                 1000                1005

Arg Ala Asn Phe Tyr Pro Leu Gln Gln Thr Asn Val Tyr Thr Thr Thr
    1010                1015                1020

Tyr Tyr Pro Ser Pro Leu Asn Lys His Ser Phe Arg Pro Glu Ala Ser
1025                1030                1035                1040

Pro Gly Gln Arg Cys Phe Pro Asn Ser
                1045

<210> SEQ ID NO 3
<211> LENGTH: 3282
<212> TYPE: DNA
<213> ORGANISM: homo sapiens -continued

<400> SEQUENCE: 3

```
atggtgcttg caggcccct ggctgtctcg ctgttgctgc ccagcctcac actgctggtg      60
tcccacctct ccagctccca ggatgtctcc agtgagccca gcagtgagca gcagctgtgc     120
gcccttagca agcaccccac cgtggccttt gaagacctgc agccgtgggt ctctaacttc     180
acctaccctg gagcccggga tttctcccag ctggctttgg accctccgg graccagctc     240
atcgtgggag ccaggaacta cctcttcaga ctcagccttg ccaatgtctc tcttcttcag     300
gccacagagt gggcctccag tgaggacacg cgccgctcct gccaaagcaa agggaagact     360
gaggaggagt gtcagaacta cgtgcgagtc ctgatcgtcg ccggccggaa ggtgttcatg     420
tgtggaacca atgccttttc ccccatgtgc accagcagac aggtggggaa cctcagccgg     480
actattgaga agatcaatgg tgtggcccgc tgcccctatg acccacgcca caactccaca     540
gctgtcatct cctcccaggg ggagctctat gcagccacgg tcatcgactt ctcaggtcgg     600
gaccctgcca tctaccgcag cctgggcagt gggccaccgc ttcgcactgc ccaatataac     660
tccaagtggc ttaatgagcc aaacttcgtg gcagcctatg atattgggct gtttgcatac     720
ttcttcctgc gggagaacgc agtggagcac gactgtggac gcaccgtgta ctctcgcgtg     780
gcccgcgtgt gcaagaatga cgtgggggc cgattcctgc tggaggacac atggaccaca     840
ttcatgaagg cccggctcaa ctgctcccgc cgggcgagg tccccttcta ctataacgag     900
ctgcagagtg ccttccactt gccrgagcag gacctcatct atggagtttt cacaaccaac     960
gtaaacagca tygcggcttc tgctgtctgc gccttcaacc tcagtgctat ctcccaggct    1020
ttcaatggcc catttcgcta ccaggagaac cccaggctg cctggctccc catagccaac    1080
cccatcccca atttccagtg tggcaccctg cctgagaccg gtcccaacga gaacctgacg    1140
gagcgcagcc tgcaggacgc gcagcgcctc ttcctgatga gcgaggccgt gcagccggtg    1200
acacccgagc cctgtgtcac ccaggacagc gtgcgcttct cacacctcgt ggtggacctg    1260
gtgcaggcta agacacgct ctaccatgta ctctacattg gcaccgagtc gggcaccatc    1320
ctgaaggcgc tgtccacggc gagccgcagc ctccacggct gctacctgga ggagctgcac    1380
gtgctgcccc ccgggcgccg cgagcccctg cgcagcctgc gcatcctgca cagcgcccgc    1440
gcgctcttcg tggggctgag agacggcgtc ctgcgggtcc cactggagag gtgcgccgcc    1500
taccgcagcc aggggggcatg cctggggggcc cgggacccgt actgtggctg ggacgggaag    1560
cagcaacgtt gcagcacact cgaggacagc tccaacatga gcctctggac ccagaacatc    1620
accgcctgtc ctgtgcggaa tgtgacacgg gatgggggct tcggcccatg gtcaccatgg    1680
caaccatgtg agcacttgga tgggacaac tcaggctctt gcctgtgtcg agctcgatcc    1740
tgtgattccc ctcgaccccg ctgtggggc cttgactgcc tggggccagc catccacatc    1800
gccaactgct ccaggaatgg ggcgtggacc ccgtggtcat cgtgggcgct gtgcagcacg    1860
tcctgtggca tcgcttcca ggtccgccag cgaagttgca gcaaccctgc tccccgccac    1920
ggggccgca tctgcgtggg caagagccgg gaggaacggt tctgtaatga aacacgcct    1980
tgcccggtgc ccatcttctg ggcttcctgg ggctcctgga gcaagtgcag cagcaactgt    2040
ggagggggca tgcagtcgcg gcgtcgggcc tgcgagaacg gcaactcctg cctgggctgc    2100
ggcgtggagt tcaagacgtg caaccccgag ggctgccccg aagtgcggcg caacaccccc    2160
tggacgccgt ggctgcccgt gaacgtgacg cagggcgggg cacggcagga gcagcggttc    2220
cgcttcaccct gccgcgcgcc ccttgcagac ccgcacggcc tgcagttcgg caggagaagg    2280
accgagacga ggacctgtcc cgcggacggc tccggctcct gcgacaccga cgccctggtg    2340
```

-continued

```
gaggacctcc tgcgcagcgg gagcacctcc ccgcacacgg tgagcggggg ctgggccgcc      2400
tggggcccgt ggtcgtcctg ctcccgggac tgcgagctgg gcttccgcgt ccgcaagaga      2460
acgtgcacta acccggagcc ccgcaacggg ggcctgccct gcgtgggcga tgctgccgag      2520
taccaggact gcaaccccca ggcttgccca gttcggggtg cttggtcctg ctggacctca      2580
tggtctccat gctcagcttc ctgtggtggg ggtcactatc aacgcaccg ttcctgcacc       2640 agccccgcac cctccccagg tgaggacatc tgtctcgggc tgcacacgga ggaggcacta     2700
tgtgccacac aggcctgccc agaaggctgg tcgccctggt ctgagtggag taagtgcact      2760
gacgacggag cccagagccg aagccggcac tgtgaggagc tcctcccagg gtccagcgcc      2820
tgtgctggaa acagcagcca gagccgcccc tgcccctaca gcagagattcc cgtcatcctg      2880 ccagcctcca gcatggagga ggccaccggc tgtgcagggt tcaatctcat ccacttggtg      2940
gccacgggca tctcctgctt cttgggctct gggctcctga ccctagcagt gtacctgtct      3000
tgccagcact gccagcgtca gtcccaggag tccacactgg tccatcctgc cacccccaac      3060
catttgcact acaagggcgg aggcaccccg aagaatgaaa agtacacacc catggaattc      3120
aagaccctga acaagaataa cttgatccct gatgacagag ccaacttcta cccattgcag      3180
cagaccaatg tgtacacgac tacttactac ccaagccccc tgaacaaaca cagcttccgg      3240
cccgaggcct cacctggaca acggtgcttc cccaacagct ga                         3282
```

<210> SEQ ID NO 4
<211> LENGTH: 1093
<212> TYPE: PRT
<213> ORGANISM: homo sapiens

<400> SEQUENCE: 4

```
Met Val Leu Ala Gly Pro Leu Ala Val Ser Leu Leu Pro Ser Leu
1               5                   10                  15

Thr Leu Leu Val Ser His Leu Ser Ser Gln Asp Val Ser Ser Glu
                20                  25                  30

Pro Ser Ser Glu Gln Gln Leu Cys Ala Leu Ser Lys His Pro Thr Val
        35                  40                  45

Ala Phe Glu Asp Leu Gln Pro Trp Val Ser Asn Phe Thr Tyr Pro Gly
    50                  55                  60

Ala Arg Asp Phe Ser Gln Leu Ala Leu Asp Pro Ser Gly Asn Gln Leu
65                  70                  75                  80

Ile Val Gly Ala Arg Asn Tyr Leu Phe Arg Leu Ser Leu Ala Asn Val
                85                  90                  95

Ser Leu Leu Gln Ala Thr Glu Trp Ala Ser Ser Glu Asp Thr Arg Arg
            100                 105                 110

Ser Cys Gln Ser Lys Gly Lys Thr Glu Glu Glu Cys Gln Asn Tyr Val
        115                 120                 125

Arg Val Leu Ile Val Ala Gly Arg Lys Val Phe Met Cys Gly Thr Asn
    130                 135                 140

Ala Phe Ser Pro Met Cys Thr Ser Arg Gln Val Gly Asn Leu Ser Arg
145                 150                 155                 160

Thr Ile Glu Lys Ile Asn Gly Val Ala Arg Cys Pro Tyr Asp Pro Arg
                165                 170                 175

His Asn Ser Thr Ala Val Ile Ser Ser Gln Gly Glu Leu Tyr Ala Ala
            180                 185                 190

Thr Val Ile Asp Phe Ser Gly Arg Asp Pro Ala Ile Tyr Arg Ser Leu
        195                 200                 205
```

-continued

```
Gly Ser Gly Pro Pro Leu Arg Thr Ala Gln Tyr Asn Ser Lys Trp Leu
        210                 215                 220

Asn Glu Pro Asn Phe Val Ala Ala Tyr Asp Ile Gly Leu Phe Ala Tyr
225                 230                 235                 240

Phe Phe Leu Arg Glu Asn Ala Val Glu His Asp Cys Gly Arg Thr Val
                245                 250                 255

Tyr Ser Arg Val Ala Arg Val Cys Lys Asn Asp Val Gly Gly Arg Phe
                260                 265                 270

Leu Leu Glu Asp Thr Trp Thr Thr Phe Met Lys Ala Arg Leu Asn Cys
            275                 280                 285

Ser Arg Pro Gly Glu Val Pro Phe Tyr Tyr Asn Glu Leu Gln Ser Ala
        290                 295                 300

Phe His Leu Pro Glu Gln Asp Leu Ile Tyr Gly Val Phe Thr Thr Asn
305                 310                 315                 320

Val Asn Ser Ile Ala Ala Ser Ala Val Cys Ala Phe Asn Leu Ser Ala
                325                 330                 335

Ile Ser Gln Ala Phe Asn Gly Pro Phe Arg Tyr Gln Glu Asn Pro Arg
            340                 345                 350

Ala Ala Trp Leu Pro Ile Ala Asn Pro Ile Pro Asn Phe Gln Cys Gly
        355                 360                 365

Thr Leu Pro Glu Thr Gly Pro Asn Glu Asn Leu Thr Glu Arg Ser Leu
370                 375                 380

Gln Asp Ala Gln Arg Leu Phe Leu Met Ser Glu Ala Val Gln Pro Val
385                 390                 395                 400

Thr Pro Glu Pro Cys Val Thr Gln Asp Ser Val Arg Phe Ser His Leu
                405                 410                 415

Val Val Asp Leu Val Gln Ala Lys Asp Thr Leu Tyr His Val Leu Tyr
            420                 425                 430

Ile Gly Thr Glu Ser Gly Thr Ile Leu Lys Ala Leu Ser Thr Ala Ser
        435                 440                 445

Arg Ser Leu His Gly Cys Tyr Leu Glu Glu Leu His Val Leu Pro Pro
450                 455                 460

Gly Arg Arg Glu Pro Leu Arg Ser Leu Arg Ile Leu His Ser Ala Arg
465                 470                 475                 480

Ala Leu Phe Val Gly Leu Arg Asp Gly Val Leu Arg Val Pro Leu Glu
                485                 490                 495

Arg Cys Ala Ala Tyr Arg Ser Gln Gly Ala Cys Leu Gly Ala Arg Asp
            500                 505                 510

Pro Tyr Cys Gly Trp Asp Gly Lys Gln Gln Arg Cys Ser Thr Leu Glu
        515                 520                 525

Asp Ser Ser Asn Met Ser Leu Trp Thr Gln Asn Ile Thr Ala Cys Pro
530                 535                 540

Val Arg Asn Val Thr Arg Asp Gly Gly Phe Gly Pro Trp Ser Pro Trp
545                 550                 555                 560

Gln Pro Cys Glu His Leu Asp Gly Asp Asn Ser Gly Ser Cys Leu Cys
                565                 570                 575

Arg Ala Arg Ser Cys Asp Ser Pro Arg Pro Arg Cys Gly Gly Leu Asp
            580                 585                 590

Cys Leu Gly Pro Ala Ile His Ile Ala Asn Cys Ser Arg Asn Gly Ala
        595                 600                 605

Trp Thr Pro Trp Ser Ser Trp Ala Leu Cys Ser Thr Ser Cys Gly Ile
610                 615                 620
```

-continued

```
Gly Phe Gln Val Arg Gln Arg Ser Cys Ser Asn Pro Ala Pro Arg His
625                 630                 635                 640

Gly Gly Arg Ile Cys Val Gly Lys Ser Arg Glu Glu Arg Phe Cys Asn
            645                 650                 655

Glu Asn Thr Pro Cys Pro Val Pro Ile Phe Trp Ala Ser Trp Gly Ser
                660                 665                 670

Trp Ser Lys Cys Ser Ser Asn Cys Gly Gly Met Gln Ser Arg Arg
            675                 680                 685

Arg Ala Cys Glu Asn Gly Asn Ser Cys Leu Gly Cys Gly Val Glu Phe
        690                 695                 700

Lys Thr Cys Asn Pro Glu Gly Cys Pro Glu Val Arg Arg Asn Thr Pro
705                 710                 715                 720

Trp Thr Pro Trp Leu Pro Val Asn Val Thr Gln Gly Gly Ala Arg Gln
                725                 730                 735

Glu Gln Arg Phe Arg Phe Thr Cys Arg Ala Pro Leu Ala Asp Pro His
            740                 745                 750

Gly Leu Gln Phe Gly Arg Arg Thr Glu Thr Arg Thr Cys Pro Ala
        755                 760                 765

Asp Gly Ser Gly Ser Cys Asp Thr Asp Ala Leu Val Glu Asp Leu Leu
770                 775                 780

Arg Ser Gly Ser Thr Ser Pro His Thr Val Ser Gly Gly Trp Ala Ala
785                 790                 795                 800

Trp Gly Pro Trp Ser Ser Cys Ser Arg Asp Cys Glu Leu Gly Phe Arg
                805                 810                 815

Val Arg Lys Arg Thr Cys Thr Asn Pro Glu Pro Arg Asn Gly Gly Leu
                820                 825                 830

Pro Cys Val Gly Asp Ala Ala Glu Tyr Gln Asp Cys Asn Pro Gln Ala
            835                 840                 845

Cys Pro Val Arg Gly Ala Trp Ser Cys Trp Thr Ser Trp Ser Pro Cys
850                 855                 860

Ser Ala Ser Cys Gly Gly Gly His Tyr Gln Arg Thr Arg Ser Cys Thr
865                 870                 875                 880

Ser Pro Ala Pro Ser Pro Gly Glu Asp Ile Cys Leu Gly Leu His Thr
                885                 890                 895

Glu Glu Ala Leu Cys Ala Thr Gln Ala Cys Pro Glu Gly Trp Ser Pro
            900                 905                 910

Trp Ser Glu Trp Ser Lys Cys Thr Asp Asp Gly Ala Gln Ser Arg Ser
            915                 920                 925

Arg His Cys Glu Glu Leu Leu Pro Gly Ser Ser Ala Cys Ala Gly Asn
        930                 935                 940

Ser Ser Gln Ser Arg Pro Cys Pro Tyr Ser Glu Ile Pro Val Ile Leu
945                 950                 955                 960

Pro Ala Ser Ser Met Glu Glu Ala Thr Gly Cys Ala Gly Phe Asn Leu
                965                 970                 975

Ile His Leu Val Ala Thr Gly Ile Ser Cys Phe Leu Gly Ser Gly Leu
            980                 985                 990

Leu Thr Leu Ala Val Tyr Leu Ser Cys Gln His Cys Gln Arg Gln Ser
        995                 1000                1005

Gln Glu Ser Thr Leu Val His Pro Ala Thr Pro Asn His Leu His Tyr
    1010                1015                1020

Lys Gly Gly Gly Thr Pro Lys Asn Glu Lys Tyr Thr Pro Met Glu Phe
1025                1030                1035                1040
```

```
Lys Thr Leu Asn Lys Asn Asn Leu Ile Pro Asp Asp Arg Ala Asn Phe
            1045                1050                1055

Tyr Pro Leu Gln Gln Thr Asn Val Tyr Thr Thr Thr Tyr Tyr Pro Ser
        1060                1065                1070

Pro Leu Asn Lys His Ser Phe Arg Pro Glu Ala Ser Pro Gly Gln Arg
    1075                1080                1085

Cys Phe Pro Asn Ser
    1090

<210> SEQ ID NO 5
<211> LENGTH: 3105
<212> TYPE: DNA
<213> ORGANISM: homo sapiens

<400> SEQUENCE: 5
atgacggtgg ttaatccaca agacctgcag ccgtgggtct ctaacttcac ctaccctgga      60
gcccgggatt tctcccagct ggctttggac ccctccggr accagctcat cgtgggagcc     120
aggaactacc tcttcagact cagccttgcc aatgtctctc ttcttcaggc cacagagtgg     180
gcctccagtg aggacacgcg ccgctcctgc aaaagcaaag gaagactga ggaggagtgt     240 cagaactacg tgcgagtcct gatcgtcgcc ggccggaagg tgttcatgtg tggaaccaat     300
gccttttccc ccatgtgcac cagcagacag gtggggaacc tcagccggac tattgagaag     360
atcaatggtg tgcccgctg cccctatgac ccacgccaca actccacagc tgtcatctcc     420 tcccagggg agctctatgc agccacggtc atcgacttct caggtcggga ccctgccatc     480
taccgcagcc tgggcagtgg gccaccgctt cgcactgccc aatataactc caagtggctt     540
aatgagccaa acttcgtggc agcctatgat attgggctgt ttgcatactt cttcctgcgg     600
gagaacgcag tggagcacga ctgtggacgc accgtgtact ctcgcgtggc ccgcgtgtgc     660
aagaatgacg tgggggccg attcctgctg gaggacacat ggaccacatt catgaaggcc     720
cggctcaact gctcccgccc gggcgaggtc cccttctact ataacgagct gcagagtgcc     780
ttccacttgc crgagcagga cctcatctat ggagttttca caaccaacgt aaacagcaty     840
gcggcttctg ctgtctgcgc cttcaacctc agtgctatct cccaggcttt caatggccca     900
tttcgctacc aggagaaccc cagggctgcc tggctcccca tagccaaccc catccccaat     960
ttccagtgtg gcaccctgcc tgagaccggt cccaacgaga acctgacgga gcgcagcctg    1020
caggacgcgc agcgcctctt cctgatgagc gaggccgtgc agccggtgac acccgagccc    1080
tgtgtcaccc aggacagcgt gcgcttctca cacctcgtgg tggacctggt gcaggctaaa    1140
gacacgctct accatgtact ctacattggc accgagtcgg gcaccatcct gaaggcgctg    1200
tccacggcga gccgcagcct ccacggctgc taccctggagg agctgcacgt gctgcccccc    1260
gggcgccgcg agcccctgcg cagcctgcgc atcctgcaca cgcccgcgc gctcttcgtg    1320 gggctgagag acgcgtcct gcgggtccca ctggagaggt cgccgccta ccgcagccag    1380 ggggcatgcc tgggggcccg ggacccgtac tgtggctggg acgggaagca gcaacgttgc    1440
agcacactcg aggacagctc caacatgagc ctctggaccc agaacatcac cgcctgtcct    1500
gtgcggaatg tgacacggga tgggggcttc ggcccatggt caccatggca accatgtgag    1560
cacttggatg gggacaactc aggctcttgc ctgtgtcgag ctcgatcctg tgattcccct    1620
cgaccccgct gtggggcct tgactgcctg gggccagcca tccacatcgc caactgctcc    1680
aggaatgggg cgtggacccc gtggtcatcg tgggcgctgt gcagcacgtc ctgtggcatc    1740
ggcttccagg tccgccagcg aagttgcagc aaccctgctc cccgccacgg gggccgcatc    1800
```

-continued

```
tgcgtgggca agagccggga ggaacggttc tgtaatgaga acacgccttg cccggtgccc      1860
atcttctggg cttcctgggg ctcctggagc aagtgcagca gcaactgtgg aggggcatg       1920 cagtcgcggc gtcgggcctg cgagaacggc aactcctgcc tgggctgcgg cgtggagttc      1980
aagacgtgca accccgaggg ctgccccgaa gtgcggcgca caccccctg gacgccgtgg       2040 ctgcccgtga acgtgacgca gggcggggca cggcaggagc agcggttccg cttcacctgc      2100
cgcgcgcccc ttgcagaccc gcacggcctg cagttcggca ggagaaggac cgagacgagg      2160
acctgtcccg cggacggctc cggctcctgc gacaccgacg ccctggtgga ggacctcctg      2220
cgcagcggga gcacctcccc gcacacggtg agcgggggct gggccgcctg ggggcccgtgg     2280 tcgtcctgct cccgggactg cgagctgggc ttccgcgtcc gcaagagaac gtgcactaac      2340
ccggagcccc gcaacggggg cctgcccctgc gtgggcgatg ctgccgagta ccaggactgc    2400 aaccccagg cttgcccagt tcggggtgct tggtcctgct ggacctcatg gtctccatgc      2460
tcagcttcct gtggtggggg tcactatcaa cgcacccgtt cctgcaccag cccgcaccc     2520 tccccaggtg aggacatctg tctcgggctg cacacggagg aggcactatg tgccacacag     2580
gcctgcccag aaggctggtc gccctggtct gagtggagta agtgcactga cgacggagcc     2640
cagagccgaa gccggcactg tgaggagctc ctcccagggt ccagcgcctg tgctggaaac    2700 agcagcaga gccgccccctg cccctacagc gagattcccg ggttcaatct catccacttg     2760
gtggccacgg gcatctcctg cttcttgggc tctgggctcc tgaccctagc agtgtacctg     2820
tcttgccagc actgccagcg tcagtcccag gagtccacac tggtccatcc tgccacccc     2880 aaccatttgc actacaaggg cggaggcacc ccgaagaatg aaaagtacac acccatggaa     2940
ttcaagaccc tgaacaagaa taacttgatc cctgatgaca gagccaactt ctacccattg     3000
cagcagacca atgtgtacac gactacttac tacccaagcc ccctgaacaa acacagcttc     3060
cggcccgagg cctcacctgg acaacggtgc ttccccaaca gctga                    3105
```

<210> SEQ ID NO 6
<211> LENGTH: 1034
<212> TYPE: PRT
<213> ORGANISM: homo sapiens

<400> SEQUENCE: 6

```
Met Thr Val Val Asn Pro Gln Asp Leu Gln Pro Trp Val Ser Asn Phe
 1               5                  10                  15

Thr Tyr Pro Gly Ala Arg Asp Phe Ser Gln Leu Ala Leu Asp Pro Ser
            20                  25                  30

Gly Asn Gln Leu Ile Val Gly Ala Arg Asn Tyr Leu Phe Arg Leu Ser
        35                  40                  45

Leu Ala Asn Val Ser Leu Leu Gln Ala Thr Glu Trp Ala Ser Ser Glu
    50                  55                  60

Asp Thr Arg Arg Ser Cys Gln Ser Lys Gly Lys Thr Glu Glu Glu Cys
65                  70                  75                  80

Gln Asn Tyr Val Arg Val Leu Ile Val Ala Gly Arg Lys Val Phe Met
                85                  90                  95

Cys Gly Thr Asn Ala Phe Ser Pro Met Cys Thr Ser Arg Gln Val Gly
            100                 105                 110

Asn Leu Ser Arg Thr Ile Glu Lys Ile Asn Gly Val Ala Arg Cys Pro
        115                 120                 125

Tyr Asp Pro Arg His Asn Ser Thr Ala Val Ile Ser Ser Gln Gly Glu
    130                 135                 140
```

-continued

```
Leu Tyr Ala Ala Thr Val Ile Asp Phe Ser Gly Arg Asp Pro Ala Ile
145                 150                 155                 160

Tyr Arg Ser Leu Gly Ser Gly Pro Pro Leu Arg Thr Ala Gln Tyr Asn
            165                 170                 175

Ser Lys Trp Leu Asn Glu Pro Asn Phe Val Ala Ala Tyr Asp Ile Gly
            180                 185                 190

Leu Phe Ala Tyr Phe Phe Leu Arg Glu Asn Ala Val Glu His Asp Cys
            195                 200                 205

Gly Arg Thr Val Tyr Ser Arg Val Ala Arg Val Cys Lys Asn Asp Val
        210                 215                 220

Gly Gly Arg Phe Leu Leu Glu Asp Thr Trp Thr Phe Met Lys Ala
225                 230                 235                 240

Arg Leu Asn Cys Ser Arg Pro Gly Glu Val Pro Phe Tyr Tyr Asn Glu
            245                 250                 255

Leu Gln Ser Ala Phe His Leu Pro Glu Gln Asp Leu Ile Tyr Gly Val
            260                 265                 270

Phe Thr Thr Asn Val Asn Ser Ile Ala Ala Ser Ala Val Cys Ala Phe
        275                 280                 285

Asn Leu Ser Ala Ile Ser Gln Ala Phe Asn Gly Pro Phe Arg Tyr Gln
290                 295                 300

Glu Asn Pro Arg Ala Ala Trp Leu Pro Ile Ala Asn Pro Ile Pro Asn
305                 310                 315                 320

Phe Gln Cys Gly Thr Leu Pro Glu Thr Gly Pro Asn Glu Asn Leu Thr
            325                 330                 335

Glu Arg Ser Leu Gln Asp Ala Gln Arg Leu Phe Leu Met Ser Glu Ala
            340                 345                 350

Val Gln Pro Val Thr Pro Glu Pro Cys Val Thr Gln Asp Ser Val Arg
            355                 360                 365

Phe Ser His Leu Val Val Asp Leu Val Gln Ala Lys Asp Thr Leu Tyr
370                 375                 380

His Val Leu Tyr Ile Gly Thr Glu Ser Gly Thr Ile Leu Lys Ala Leu
385                 390                 395                 400

Ser Thr Ala Ser Arg Ser Leu His Gly Cys Tyr Leu Glu Glu Leu His
            405                 410                 415

Val Leu Pro Pro Gly Arg Arg Glu Pro Leu Arg Ser Leu Arg Ile Leu
            420                 425                 430

His Ser Ala Arg Ala Leu Phe Val Gly Leu Arg Asp Gly Val Leu Arg
            435                 440                 445

Val Pro Leu Glu Arg Cys Ala Ala Tyr Arg Ser Gln Gly Ala Cys Leu
450                 455                 460

Gly Ala Arg Asp Pro Tyr Cys Gly Trp Asp Gly Lys Gln Gln Arg Cys
465                 470                 475                 480

Ser Thr Leu Glu Asp Ser Ser Asn Met Ser Leu Trp Thr Gln Asn Ile
            485                 490                 495

Thr Ala Cys Pro Val Arg Asn Val Thr Arg Asp Gly Gly Phe Gly Pro
            500                 505                 510

Trp Ser Pro Trp Gln Pro Cys Glu His Leu Asp Gly Asp Asn Ser Gly
            515                 520                 525

Ser Cys Leu Cys Arg Ala Arg Ser Cys Asp Ser Pro Arg Pro Arg Cys
        530                 535                 540

Gly Gly Leu Asp Cys Leu Gly Pro Ala Ile His Ile Ala Asn Cys Ser
545                 550                 555                 560
```

-continued

```
Arg Asn Gly Ala Trp Thr Pro Trp Ser Ser Trp Ala Leu Cys Ser Thr
            565                 570                 575

Ser Cys Gly Ile Gly Phe Gln Val Arg Gln Arg Ser Cys Ser Asn Pro
            580                 585                 590

Ala Pro Arg His Gly Gly Arg Ile Cys Val Gly Lys Ser Arg Glu Glu
            595                 600                 605

Arg Phe Cys Asn Glu Asn Thr Pro Cys Pro Val Pro Ile Phe Trp Ala
            610                 615                 620

Ser Trp Gly Ser Trp Ser Lys Cys Ser Ser Asn Cys Gly Gly Gly Met
625                 630                 635                 640

Gln Ser Arg Arg Arg Ala Cys Glu Asn Gly Asn Ser Cys Leu Gly Cys
            645                 650                 655

Gly Val Glu Phe Lys Thr Cys Asn Pro Glu Gly Cys Pro Glu Val Arg
            660                 665                 670

Arg Asn Thr Pro Trp Thr Pro Trp Leu Pro Val Asn Val Thr Gln Gly
            675                 680                 685

Gly Ala Arg Gln Glu Gln Arg Phe Arg Phe Thr Cys Arg Ala Pro Leu
            690                 695                 700

Ala Asp Pro His Gly Leu Gln Phe Gly Arg Arg Arg Thr Glu Thr Arg
705                 710                 715                 720

Thr Cys Pro Ala Asp Gly Ser Gly Ser Cys Asp Thr Asp Ala Leu Val
            725                 730                 735

Glu Asp Leu Leu Arg Ser Gly Ser Thr Ser Pro His Thr Val Ser Gly
            740                 745                 750

Gly Trp Ala Ala Trp Gly Pro Trp Ser Ser Cys Ser Arg Asp Cys Glu
            755                 760                 765

Leu Gly Phe Arg Val Arg Lys Arg Thr Cys Thr Asn Pro Glu Pro Arg
            770                 775                 780

Asn Gly Gly Leu Pro Cys Val Gly Asp Ala Ala Glu Tyr Gln Asp Cys
785                 790                 795                 800

Asn Pro Gln Ala Cys Pro Val Arg Gly Ala Trp Ser Cys Trp Thr Ser
            805                 810                 815

Trp Ser Pro Cys Ser Ala Ser Cys Gly Gly Gly His Tyr Gln Arg Thr
            820                 825                 830

Arg Ser Cys Thr Ser Pro Ala Pro Ser Pro Gly Glu Asp Ile Cys Leu
            835                 840                 845

Gly Leu His Thr Glu Glu Ala Leu Cys Ala Thr Gln Ala Cys Pro Glu
            850                 855                 860

Gly Trp Ser Pro Trp Ser Glu Trp Ser Lys Cys Thr Asp Asp Gly Ala
865                 870                 875                 880

Gln Ser Arg Ser Arg His Cys Glu Glu Leu Leu Pro Gly Ser Ser Ala
            885                 890                 895

Cys Ala Gly Asn Ser Ser Gln Ser Arg Pro Cys Pro Tyr Ser Glu Ile
            900                 905                 910

Pro Gly Phe Asn Leu Ile His Leu Val Ala Thr Gly Ile Ser Cys Phe
            915                 920                 925

Leu Gly Ser Gly Leu Leu Thr Leu Ala Val Tyr Leu Ser Cys Gln His
            930                 935                 940

Cys Gln Arg Gln Ser Gln Glu Ser Thr Leu Val His Pro Ala Thr Pro
945                 950                 955                 960

Asn His Leu His Tyr Lys Gly Gly Gly Thr Pro Lys Asn Glu Lys Tyr
            965                 970                 975
```

-continued

Thr Pro Met Glu Phe Lys Thr Leu Asn Lys Asn Asn Leu Ile Pro Asp
            980                 985                 990

Asp Arg Ala Asn Phe Tyr Pro Leu Gln Gln Thr Asn Val Tyr Thr Thr
        995                 1000                1005

Thr Tyr Tyr Pro Ser Pro Leu Asn Lys His Ser Phe Arg Pro Glu Ala
    1010                1015                1020

Ser Pro Gly Gln Arg Cys Phe Pro Asn Ser
1025                1030

<210> SEQ ID NO 7
<211> LENGTH: 3237
<212> TYPE: DNA
<213> ORGANISM: homo sapiens

<400> SEQUENCE: 7

| | |
|---|---|
| atggtgcttg caggccccct ggctgtctcg ctgttgctgc ccagcctcac actgctggtg | 60 |
| tcccacctct ccagctccca ggatgtctcc agtgagccca gcagtgagca gcagctgtgc | 120 |
| gcccttagca agcaccccac cgtggccttt gaagacctgc agccgtgggt ctctaacttc | 180 |
| acctaccctg gagcccggga tttctcccag ctggctttgg acccctccgg graccagctc | 240 |
| atcgtgggag ccaggaacta cctcttcaga ctcagccttg ccaatgtctc tcttcttcag | 300 |
| gccacagagt gggcctccag tgaggacacg cgccgtcct gccaaagcaa agggaagact | 360 |
| gaggaggagt gtcagaacta cgtgcgagtc ctgatcgtcg ccggccggaa ggtgttcatg | 420 |
| tgtggaacca atgccttttc ccccatgtgc accagcagac aggtggggaa cctcagccgg | 480 |
| actattgaga agatcaatgg tgtggcccgc tgcccctatg acccacgcca caactccaca | 540 |
| gctgtcatct cctcccaggg ggagctctat gcagccacgg tcatcgactt ctcaggtcgg | 600 |
| gaccctgcca tctaccgcag cctgggcagt gggccaccgc ttcgcactgc caatataac | 660 |
| tccaagtggc ttaatgagcc aaacttcgtg gcagcctatg atattgggct gtttgcatac | 720 |
| ttcttcctgc gggagaacgc agtggagcac gactgtggac gcaccgtgta ctctcgcgtg | 780 |
| gcccgcgtgt gcaagaatga cgtgggggc cgattcctgc tggaggacac atggaccaca | 840 |
| ttcatgaagg cccggctcaa ctgctcccgc ccgggcgagg tccccttcta ctataacgag | 900 |
| ctgcagagtg cctccacctt gccrgagcag gacctcatct atggagtttt cacaaccaac | 960 |
| gtaaacagca tygcggcttc tgctgtctgc gccttcaacc tcagtgctat ctcccaggct | 1020 |
| ttcaatggcc catttcgcta ccaggagaac cccaggggctg cctggctccc catagccaac | 1080 |
| cccatcccca atttccagtg tggcacctg cctgagaccg tcccaacga gaacctgacg | 1140 |
| gagcgcagcc tgcaggacgc gcagcgcctc ttcctgatga gcgaggccgt gcagccggtg | 1200 |
| acacccgagc cctgtgtcac ccaggacagc gtgcgcttct cacacctcgt ggtggacctg | 1260 |
| gtgcaggcta agacacgct ctaccatgta ctctacattg caccgagtc gggcaccatc | 1320 |
| ctgaaggcgc tgtccacggc gagccgcagc tccacggct gctacctgga ggagctgcac | 1380 |
| gtgctgcccc ccgggcgccg cgagcccctg cgcagcctgc gcatcctgca gcgcccgc | 1440 |
| gcgctcttcg tgggctgag agacggcgtc ctgcgggtcc cactggagag gtgcgccgcc | 1500 |
| taccgcagcc agggggcatg cctgggggcc cgggaccgt actgtggctg ggacgggaag | 1560 |
| cagcaacgtt gcagcacact cgaggacagc tccaacatga gcctctggac ccagaacatc | 1620 |
| accgcctgtc ctgtgcggaa tgtgacacgg gatgggggct cggcccatg gtcaccatgg | 1680 |
| caaccatgtg agcacttgga tgggacaac tcaggctctt gcctgtgtcg agctcgatcc | 1740 |
| tgtgattccc ctcgaccccg ctgtgggggc cttgactgcc tggggccagc catccacatc | 1800 |

-continued

```
gccaactgct ccaggaatgg ggcgtggacc ccgtggtcat cgtgggcgct gtgcagcacg    1860
tcctgtggca tcggcttcca ggtccgccag cgaagttgca gcaaccctgc tccccgccac    1920
ggggccgca tctgcgtggg caagagccgg aggaacggt tctgtaatga aacacgcct       1980
tgcccggtgc ccatcttctg ggcttcctgg ggctcctgga gcaagtgcag cagcaactgt    2040
ggagggggca tgcagtcgcg cgtcgggcc tgcgagaacg gcaactcctg cctgggctgc     2100
ggcgtggagt tcaagacgtg caaccccgag ggctgccccg aagtgcggcg caacaccccc    2160
tggacgccgt ggctgcccgt gaacgtgacg cagggcgggg cacggcagga gcagcggttc    2220
cgcttcacct gccgcgcgcc ccttgcagac ccgcacggcc tgcagttcgg caggagaagg    2280
accgagacga ggacctgtcc cgcggacggc tccggctcct gcgacaccga cgccctggtg    2340
gaggacctcc tgcgcagcgg gagcacctcc ccgcacacgg tgagcggggg ctgggccgcc    2400
tggggcccgt ggtcgtcctg ctcccgggac tgcgagctgg gcttccgcgt ccgcaagaga    2460
acgtgcacta acccggagcc ccgcaacggg ggcctgccct gcgtgggcga tgctgccgag    2520
taccaggact gcaaccccca ggcttgccca gttcggggtg cttggtcctg ctggacctca    2580
tggtctccat gctcagcttc ctgtggtggg ggtcactatc aacgcacccg ttcctgcacc    2640
agccccgcac cctccccagg tgaggacatc tgtctcgggc tgcacacgga ggaggcacta    2700
tgtgccacac aggcctgccc agaaggctgg tcgccctggt ctgagtggag taagtgcact    2760
gacgacggag cccagagccg aagccggcac tgtgaggagc tcctcccagg tccagcgcc    2820
tgtgctggaa acagcagcca gagccgcccc tgccccctaca gcgagattcc cgggttcaat    2880
ctcatccact ggtggccac gggcatctcc tgcttcttgg gctctgggct cctgacccta    2940
gcagtgtacc tgtcttgcca gcactgccag cgtcagtccc aggagtccac actggtccat    3000
cctgccaccc ccaaccattt gcactacaag ggcggaggca cccccgaagaa tgaaaagtac    3060
acacccatgg aattcaagac cctgaacaag aataacttga tccctgatga cagagccaac    3120
ttctacccat tgcagcagac caatgtgtac acgactactt actacccaag ccccctgaac    3180
aaacacagct ccggcccga ggcctcacct ggacaacggt gcttccccaa cagctga       3237
```

<210> SEQ ID NO 8
<211> LENGTH: 1078
<212> TYPE: PRT
<213> ORGANISM: homo sapiens

<400> SEQUENCE: 8

```
Met Val Leu Ala Gly Pro Leu Ala Val Ser Leu Leu Pro Ser Leu
 1               5                  10                  15

Thr Leu Val Ser His Leu Ser Ser Ser Gln Asp Val Ser Ser Glu
                20                  25                  30

Pro Ser Glu Gln Gln Leu Cys Ala Leu Ser Lys His Pro Thr Val
                35                  40                  45

Ala Phe Glu Asp Leu Gln Pro Trp Val Ser Asn Phe Thr Tyr Pro Gly
    50                  55                  60

Ala Arg Asp Phe Ser Gln Leu Ala Leu Asp Pro Ser Gly Asn Gln Leu
65                  70                  75                  80

Ile Val Gly Ala Arg Asn Tyr Leu Phe Arg Leu Ser Leu Ala Asn Val
                    85                  90                  95

Ser Leu Leu Gln Ala Thr Glu Trp Ala Ser Ser Glu Asp Thr Arg Arg
                100                 105                 110

Ser Cys Gln Ser Lys Gly Lys Thr Glu Glu Glu Cys Gln Asn Tyr Val
            115                 120                 125
```

-continued

```
Arg Val Leu Ile Val Ala Gly Arg Lys Val Phe Met Cys Gly Thr Asn
    130                 135                 140

Ala Phe Ser Pro Met Cys Thr Ser Arg Gln Val Gly Asn Leu Ser Arg
145                 150                 155                 160

Thr Ile Glu Lys Ile Asn Gly Val Ala Arg Cys Pro Tyr Asp Pro Arg
                165                 170                 175

His Asn Ser Thr Ala Val Ile Ser Ser Gln Gly Glu Leu Tyr Ala Ala
                180                 185                 190

Thr Val Ile Asp Phe Ser Gly Arg Asp Pro Ala Ile Tyr Arg Ser Leu
            195                 200                 205

Gly Ser Gly Pro Pro Leu Arg Thr Ala Gln Tyr Asn Ser Lys Trp Leu
210                 215                 220

Asn Glu Pro Asn Phe Val Ala Ala Tyr Asp Ile Gly Leu Phe Ala Tyr
225                 230                 235                 240

Phe Phe Leu Arg Glu Asn Ala Val Glu His Asp Cys Gly Arg Thr Val
                245                 250                 255

Tyr Ser Arg Val Ala Arg Val Cys Lys Asn Asp Val Gly Gly Arg Phe
                260                 265                 270

Leu Leu Glu Asp Thr Trp Thr Thr Phe Met Lys Ala Arg Leu Asn Cys
            275                 280                 285

Ser Arg Pro Gly Glu Val Pro Phe Tyr Asn Glu Leu Gln Ser Ala
290                 295                 300

Phe His Leu Pro Glu Gln Asp Leu Ile Tyr Gly Val Phe Thr Thr Asn
305                 310                 315                 320

Val Asn Ser Ile Ala Ala Ser Ala Val Cys Ala Phe Asn Leu Ser Ala
                325                 330                 335

Ile Ser Gln Ala Phe Asn Gly Pro Phe Arg Tyr Gln Glu Asn Pro Arg
                340                 345                 350

Ala Ala Trp Leu Pro Ile Ala Asn Pro Ile Pro Asn Phe Gln Cys Gly
            355                 360                 365

Thr Leu Pro Glu Thr Gly Pro Asn Glu Asn Leu Thr Glu Arg Ser Leu
370                 375                 380

Gln Asp Ala Gln Arg Leu Phe Leu Met Ser Glu Ala Val Gln Pro Val
385                 390                 395                 400

Thr Pro Glu Pro Cys Val Thr Gln Asp Ser Val Arg Phe Ser His Leu
                405                 410                 415

Val Val Asp Leu Val Gln Ala Lys Asp Thr Leu Tyr His Val Leu Tyr
            420                 425                 430

Ile Gly Thr Glu Ser Gly Thr Ile Leu Lys Ala Leu Ser Thr Ala Ser
            435                 440                 445

Arg Ser Leu His Gly Cys Tyr Leu Glu Glu Leu His Val Leu Pro Pro
450                 455                 460

Gly Arg Arg Glu Pro Leu Arg Ser Leu Arg Ile Leu His Ser Ala Arg
465                 470                 475                 480

Ala Leu Phe Val Gly Leu Arg Asp Gly Val Leu Arg Val Pro Leu Glu
                485                 490                 495

Arg Cys Ala Ala Tyr Arg Ser Gln Gly Ala Cys Leu Gly Ala Arg Asp
                500                 505                 510

Pro Tyr Cys Gly Trp Asp Gly Lys Gln Gln Arg Cys Ser Thr Leu Glu
            515                 520                 525

Asp Ser Ser Asn Met Ser Leu Trp Thr Gln Asn Ile Thr Ala Cys Pro
530                 535                 540
```

-continued

Val Arg Asn Val Thr Arg Asp Gly Gly Phe Gly Pro Trp Ser Pro Trp
545                 550                 555                 560

Gln Pro Cys Glu His Leu Asp Gly Asp Asn Ser Gly Ser Cys Leu Cys
                565                 570                 575

Arg Ala Arg Ser Cys Asp Ser Pro Arg Pro Arg Cys Gly Gly Leu Asp
            580                 585                 590

Cys Leu Gly Pro Ala Ile His Ile Ala Asn Cys Ser Arg Asn Gly Ala
        595                 600                 605

Trp Thr Pro Trp Ser Ser Trp Ala Leu Cys Ser Thr Ser Cys Gly Ile
    610                 615                 620

Gly Phe Gln Val Arg Gln Arg Ser Cys Ser Asn Pro Ala Pro Arg His
625                 630                 635                 640

Gly Gly Arg Ile Cys Val Gly Lys Ser Arg Glu Glu Arg Phe Cys Asn
                645                 650                 655

Glu Asn Thr Pro Cys Pro Val Pro Ile Phe Trp Ala Ser Trp Gly Ser
            660                 665                 670

Trp Ser Lys Cys Ser Ser Asn Cys Gly Gly Met Gln Ser Arg Arg
        675                 680                 685

Arg Ala Cys Glu Asn Gly Asn Ser Cys Leu Gly Cys Gly Val Glu Phe
    690                 695                 700

Lys Thr Cys Asn Pro Glu Gly Cys Pro Glu Val Arg Arg Asn Thr Pro
705                 710                 715                 720

Trp Thr Pro Trp Leu Pro Val Asn Val Thr Gln Gly Gly Ala Arg Gln
                725                 730                 735

Glu Gln Arg Phe Arg Phe Thr Cys Arg Ala Pro Leu Ala Asp Pro His
            740                 745                 750

Gly Leu Gln Phe Gly Arg Arg Thr Glu Thr Arg Thr Cys Pro Ala
        755                 760                 765

Asp Gly Ser Gly Ser Cys Asp Thr Asp Ala Leu Val Glu Asp Leu Leu
    770                 775                 780

Arg Ser Gly Ser Thr Ser Pro His Thr Val Ser Gly Gly Trp Ala Ala
785                 790                 795                 800

Trp Gly Pro Trp Ser Ser Cys Ser Arg Asp Cys Glu Leu Gly Phe Arg
                805                 810                 815

Val Arg Lys Arg Thr Cys Thr Asn Pro Glu Pro Arg Asn Gly Gly Leu
            820                 825                 830

Pro Cys Val Gly Asp Ala Ala Glu Tyr Gln Asp Cys Asn Pro Gln Ala
        835                 840                 845

Cys Pro Val Arg Gly Ala Trp Ser Cys Trp Thr Ser Trp Ser Pro Cys
    850                 855                 860

Ser Ala Ser Cys Gly Gly His Tyr Gln Arg Thr Arg Ser Cys Thr
865                 870                 875                 880

Ser Pro Ala Pro Ser Pro Gly Glu Asp Ile Cys Leu Gly Leu His Thr
                885                 890                 895

Glu Glu Ala Leu Cys Ala Thr Gln Ala Cys Pro Glu Gly Trp Ser Pro
            900                 905                 910

Trp Ser Glu Trp Ser Lys Cys Thr Asp Asp Gly Ala Gln Ser Arg Ser
        915                 920                 925

Arg His Cys Glu Glu Leu Leu Pro Gly Ser Ser Ala Cys Ala Gly Asn
    930                 935                 940

Ser Ser Gln Ser Arg Pro Cys Pro Tyr Ser Glu Ile Pro Gly Phe Asn
945                 950                 955                 960

```
Leu Ile His Leu Val Ala Thr Gly Ile Ser Cys Phe Leu Gly Ser Gly
            965                 970                 975
Leu Leu Thr Leu Ala Val Tyr Leu Ser Cys Gln His Cys Gln Arg Gln
            980                 985                 990
Ser Gln Glu Ser Thr Leu Val His Pro Ala Thr Pro Asn His Leu His
            995                 1000                1005
Tyr Lys Gly Gly Gly Thr Pro Lys Asn Glu Lys Tyr Thr Pro Met Glu
            1010                1015                1020
Phe Lys Thr Leu Asn Lys Asn Asn Leu Ile Pro Asp Asp Arg Ala Asn
1025                1030                1035                1040
Phe Tyr Pro Leu Gln Gln Thr Asn Val Tyr Thr Thr Tyr Tyr Pro
            1045                1050                1055
Ser Pro Leu Asn Lys His Ser Phe Arg Pro Glu Ala Ser Pro Gly Gln
            1060                1065                1070
Arg Cys Phe Pro Asn Ser
        1075
```

<210> SEQ ID NO 9
<211> LENGTH: 3456
<212> TYPE: DNA
<213> ORGANISM: homo sapiens

<400> SEQUENCE: 9

```
atgccctgtg gcttcagtcc gtctcctgtt gcccaccacc tcgtccctgg ccgcctgat      60
accccagccc aacagctaag gtgtggatgg acagtagggg gctggcttct ctcactggtc    120
agggtcttc tcccctgtct gcctcccgga gctaggactg cagaggggcc tatcatggtg     180
cttgcaggcc cctggctgt ctcgctgttg ctgcccagcc tcacactgct ggtgtcccac     240
ctctccagct cccaggatgt ctccagtgag cccagcagtg agcagcagct gtgcgccctt    300
agcaagcacc ccaccgtggc cttgaagac ctgcagccgt gggtctctaa cttcacctac     360
cctggagccc gggatttctc ccagctggct ttggaccct ccgggtacca gctcatcgtg     420
ggagccagga actacctctt cagactcagc cttgccaatg tctctcttct tcaggccaca    480
gagtgggcct ccagtgagga cacgcgccgc tcctgccaaa gcaaagggaa gactgaggag    540
gagtgtcaga actacgtgcg agtcctgatc gtcgccggcc ggaaggtgtt catgtgtgga    600
accaatgcct ttccccccat gtgcaccagc agacaggtgg ggaacctcag ccggactatt    660
gagaagatca atggtgtggc ccgctgcccc tatgacccac gccacaactc acagctgtc    720
atctcctccc aggggagct ctatgcagcc acggtcatcg acttctcagg tcgggaccct     780
gccatctacc gcagcctggg cagtgggcca ccgcttcgca ctgcccaata taactccaag    840
tggcttaatg agccaaactt cgtggcagcc tatgatattg gctgtttgc atacttcttc     900
ctgcggggaga acgcagtgga gcacgactgt ggacgcaccg tgtactctcg cgtggcccgc    960
gtgtgcaaga atgacgtggg gggccgattc ctgctggagg acacatggac acattcatg    1020
aaggcccggc tcaactgctc ccgcccgggc gaggtcccct ctactataa cgagctgcag    1080
agtgccttcc acttgccrga gcaggacctc atctatggag ttttcacaac caacgtaaac    1140
agcatygcgg cttctgctgt ctgcgccttc aacctcagtg ctatctccca ggctttcaat    1200
ggcccatttc gctaccagga gaaccccagg gctgcctggc tcccatagc caaccccatc    1260
cccaatttcc agtgtggcac cctgcctgag accggtccca cgagaacct gacggagcgc    1320
agcctgcagg acgcgcagcg cctcttcctg atgagcgagg ccgtgcagcc ggtgacaccc    1380
```

-continued

```
gagccctgtg tcacccagga cagcgtgcgc ttctcacacc tcgtggtgga cctggtgcag    1440
gctaaagaca cgctctacca tgtactctac attggcaccg agtcgggcac catcctgaag    1500
gcgctgtcca cggcgagccg cagcctccac ggctgctacc tggaggagct gcacgtgctg    1560
ccccccgggc gccgcgagcc cctgcgcagc ctgcgcatcc tgcacagcgc ccgcgcgctc    1620
ttcgtggggc tgagagacgg cgtcctgcgg gtcccactgg agaggtgcgc cgcctaccgc    1680
agccaggggg catgcctggg ggcccgggac ccgtactgtg gctgggacgg gaagcagcaa    1740
cgttgcagca cactcgagga cagctccaac atgagcctct ggacccagaa catcaccgcc    1800
tgtcctgtgc ggaatgtgac acgggatggg ggcttcggcc catggtcacc atggcaacca    1860
tgtgagcact tggatgggga caactcaggc tcttgcctgt gtcgagctcg atcctgtgat    1920
tcccctcgac cccgctgtgg gggccttgac tgcctggggc cagccatcca catcgccaac    1980
tgctccagga atggggcgtg gaccccgtgg tcatcgtggg cgctgtgcag cacgtcctgt    2040
ggcatcggct ccaggtccg ccagcgaagt tgcagcaacc ctgctccccg ccacggggc     2100 cgcatctgcg tgggcaagag ccgggaggaa cggttctgta atgagaacac gccttgcccg    2160
gtgcccatct tctgggcttc ctggggctcc tggagcaagt gcagcagcaa ctgtggaggg    2220
ggcatgcagt cgcggcgtcg ggcctgcgag aacggcaact cctgcctggg ctgcggcgtg    2280
gagttcaaga cgtgcaaccc cgagggctgc ccgaagtgc ggcgcaacac ccctggacg     2340 ccgtggctgc ccgtgaacgt gacgcagggc ggggcacggc aggagcagcg gttccgcttc    2400
acctgccgcg cgcccttgc agacccgcac ggcctgcagt tcggcaggag aaggaccgag    2460
acgaggacct gtcccgcgga cggctccggc tcctgcgaca ccgacgccct ggtggaggac    2520
ctcctgcgca gcgggagcac ctccccgcac acggtgagcg ggggctgggc cgcctggggc    2580
ccgtggtcgt cctgctcccg ggactgcgag ctgggcttcc gcgtccgcaa gagaacgtgc    2640
actaacccgg agccccgcaa cggggggcctg ccctgcgtgg gcgatgctgc cgagtaccag    2700
gactgcaacc cccaggcttg cccagttcgg ggtgcttggt cctgctggac ctcatggtct    2760
ccatgctcag cttcctgtgg tggggtcac tatcaacgca cccgttcctg caccagcccc    2820
gcaccctccc caggtgagga catctgtctc gggctgcaca cggaggaggc actatgtgcc    2880
acacaggcct gccagaagg ctggtcgccc tggtctgagt ggagtaagtg cactgacgac    2940
ggagcccaga gccgaagccg gcactgtgag gagctcctcc cagggtccag cgcctgtgct    3000
ggaaacagca gccagagccg cccctgcccc tacagcgaga ttcccgtcat cctgccagcc    3060
tccagcatgg aggaggccac cggctgtgca gggttcaatc tcatccactt ggtggccacg    3120
ggcatctcct gcttcttggg ctctgggctc ctgaccctag cagtgtacct gtcttgccag    3180
cactgccagc gtcagtccca ggagtccaca ctggtccatc ctgccacccc caaccatttg    3240
cactacaagg gcggaggcac cccgaagaat gaaaagtaca cacccatgga attcaagacc    3300
ctgaacaaga ataacttgat ccctgatgac agagccaact tctacccatt gcagcagacc    3360
aatgtgtaca cgactactta ctacccaagc ccctgaaca aacacagctt ccggcccgag    3420
gcctcacctg gacaacggtg cttccccaac agctga                              3456
```

<210> SEQ ID NO 10
<211> LENGTH: 1151
<212> TYPE: PRT
<213> ORGANISM: homo sapiens

<400> SEQUENCE: 10

```
Met Pro Cys Gly Phe Ser Pro Ser Pro Val Ala His His Leu Val Pro
  1               5                  10                  15
Gly Pro Pro Asp Thr Pro Ala Gln Gln Leu Arg Cys Gly Trp Thr Val
                 20                  25                  30
Gly Gly Trp Leu Leu Ser Leu Val Arg Gly Leu Leu Pro Cys Leu Pro
             35                  40                  45
Pro Gly Ala Arg Thr Ala Glu Gly Pro Ile Met Val Leu Ala Gly Pro
         50                  55                  60
Leu Ala Val Ser Leu Leu Leu Pro Ser Leu Thr Leu Leu Val Ser His
 65                  70                  75                  80
Leu Ser Ser Ser Gln Asp Val Ser Ser Glu Pro Ser Ser Glu Gln Gln
                 85                  90                  95
Leu Cys Ala Leu Ser Lys His Pro Thr Val Ala Phe Glu Asp Leu Gln
                100                 105                 110
Pro Trp Val Ser Asn Phe Thr Tyr Pro Gly Ala Arg Asp Phe Ser Gln
            115                 120                 125
Leu Ala Leu Asp Pro Ser Gly Asn Gln Leu Ile Val Gly Ala Arg Asn
130                 135                 140
Tyr Leu Phe Arg Leu Ser Leu Ala Asn Val Ser Leu Leu Gln Ala Thr
145                 150                 155                 160
Glu Trp Ala Ser Ser Glu Asp Thr Arg Arg Ser Cys Gln Ser Lys Gly
                165                 170                 175
Lys Thr Glu Glu Glu Cys Gln Asn Tyr Val Arg Val Leu Ile Val Ala
                180                 185                 190
Gly Arg Lys Val Phe Met Cys Gly Thr Asn Ala Phe Ser Pro Met Cys
            195                 200                 205
Thr Ser Arg Gln Val Gly Asn Leu Ser Arg Thr Ile Glu Lys Ile Asn
        210                 215                 220
Gly Val Ala Arg Cys Pro Tyr Asp Pro Arg His Asn Ser Thr Ala Val
225                 230                 235                 240
Ile Ser Ser Gln Gly Glu Leu Tyr Ala Ala Thr Val Ile Asp Phe Ser
                245                 250                 255
Gly Arg Asp Pro Ala Ile Tyr Arg Ser Leu Gly Ser Gly Pro Pro Leu
            260                 265                 270
Arg Thr Ala Gln Tyr Asn Ser Lys Trp Leu Asn Glu Pro Asn Phe Val
        275                 280                 285
Ala Ala Tyr Asp Ile Gly Leu Phe Ala Tyr Phe Phe Leu Arg Glu Asn
    290                 295                 300
Ala Val Glu His Asp Cys Gly Arg Thr Val Tyr Ser Arg Val Ala Arg
305                 310                 315                 320
Val Cys Lys Asn Asp Val Gly Gly Arg Phe Leu Leu Glu Asp Thr Trp
                325                 330                 335
Thr Thr Phe Met Lys Ala Arg Leu Asn Cys Ser Arg Pro Gly Glu Val
            340                 345                 350
Pro Phe Tyr Tyr Asn Glu Leu Gln Ser Ala Phe His Leu Pro Glu Gln
        355                 360                 365
Asp Leu Ile Tyr Gly Val Phe Thr Thr Asn Val Asn Ser Ile Ala Ala
    370                 375                 380
Ser Ala Val Cys Ala Phe Asn Leu Ser Ala Ile Ser Gln Ala Phe Asn
385                 390                 395                 400
Gly Pro Phe Arg Tyr Gln Glu Asn Pro Arg Ala Ala Trp Leu Pro Ile
                405                 410                 415
```

```
Ala Asn Pro Ile Pro Asn Phe Gln Cys Gly Thr Leu Pro Glu Thr Gly
            420                 425                 430

Pro Asn Glu Asn Leu Thr Glu Arg Ser Leu Gln Asp Ala Gln Arg Leu
        435                 440                 445

Phe Leu Met Ser Glu Ala Val Gln Pro Val Thr Pro Glu Pro Cys Val
    450                 455                 460

Thr Gln Asp Ser Val Arg Phe Ser His Leu Val Val Asp Leu Val Gln
465                 470                 475                 480

Ala Lys Asp Thr Leu Tyr His Val Leu Tyr Ile Gly Thr Glu Ser Gly
                485                 490                 495

Thr Ile Leu Lys Ala Leu Ser Thr Ala Ser Arg Ser Leu His Gly Cys
            500                 505                 510

Tyr Leu Glu Glu Leu His Val Leu Pro Pro Gly Arg Arg Glu Pro Leu
        515                 520                 525

Arg Ser Leu Arg Ile Leu His Ser Ala Arg Ala Leu Phe Val Gly Leu
    530                 535                 540

Arg Asp Gly Val Leu Arg Val Pro Leu Glu Arg Cys Ala Ala Tyr Arg
545                 550                 555                 560

Ser Gln Gly Ala Cys Leu Gly Ala Arg Asp Pro Tyr Cys Gly Trp Asp
                565                 570                 575

Gly Lys Gln Gln Arg Cys Ser Thr Leu Glu Asp Ser Ser Asn Met Ser
            580                 585                 590

Leu Trp Thr Gln Asn Ile Thr Ala Cys Pro Val Arg Asn Val Thr Arg
        595                 600                 605

Asp Gly Gly Phe Gly Pro Trp Ser Pro Trp Gln Pro Cys Glu His Leu
    610                 615                 620

Asp Gly Asp Asn Ser Gly Ser Cys Leu Cys Arg Ala Arg Ser Cys Asp
625                 630                 635                 640

Ser Pro Arg Pro Arg Cys Gly Gly Leu Asp Cys Leu Gly Pro Ala Ile
                645                 650                 655

His Ile Ala Asn Cys Ser Arg Asn Gly Ala Trp Thr Pro Trp Ser Ser
            660                 665                 670

Trp Ala Leu Cys Ser Thr Ser Cys Gly Ile Gly Phe Gln Val Arg Gln
        675                 680                 685

Arg Ser Cys Ser Asn Pro Ala Pro Arg His Gly Gly Arg Ile Cys Val
    690                 695                 700

Gly Lys Ser Arg Glu Glu Arg Phe Cys Asn Glu Asn Thr Pro Cys Pro
705                 710                 715                 720

Val Pro Ile Phe Trp Ala Ser Trp Gly Ser Trp Ser Lys Cys Ser Ser
                725                 730                 735

Asn Cys Gly Gly Gly Met Gln Ser Arg Arg Arg Ala Cys Glu Asn Gly
            740                 745                 750

Asn Ser Cys Leu Gly Cys Gly Val Glu Phe Lys Thr Cys Asn Pro Glu
        755                 760                 765

Gly Cys Pro Glu Val Arg Arg Asn Thr Pro Trp Thr Pro Trp Leu Pro
    770                 775                 780

Val Asn Val Thr Gln Gly Gly Ala Arg Gln Glu Gln Arg Phe Arg Phe
785                 790                 795                 800

Thr Cys Arg Ala Pro Leu Ala Asp Pro His Gly Leu Gln Phe Gly Arg
                805                 810                 815

Arg Arg Thr Glu Thr Arg Thr Cys Pro Ala Asp Gly Ser Gly Ser Cys
            820                 825                 830
```

| | | | | | | | | | | | | |
|---|---|---|---|---|---|---|---|---|---|---|---|---|
|Asp|Thr|Asp|Ala|Leu|Val|Glu|Asp|Leu|Leu|Arg|Ser|Gly Ser Thr Ser|
| |835| | | |840| | | |845| | | |

Pro His Thr Val Ser Gly Gly Trp Ala Ala Trp Gly Pro Trp Ser Ser
            850                 855                 860

Cys Ser Arg Asp Cys Glu Leu Gly Phe Arg Val Arg Lys Arg Thr Cys
865                 870                 875                 880

Thr Asn Pro Glu Pro Arg Asn Gly Gly Leu Pro Cys Val Gly Asp Ala
                885                 890                 895

Ala Glu Tyr Gln Asp Cys Asn Pro Gln Ala Cys Pro Val Arg Gly Ala
            900                 905                 910

Trp Ser Cys Trp Thr Ser Trp Ser Pro Cys Ser Ala Ser Cys Gly Gly
            915                 920                 925

Gly His Tyr Gln Arg Thr Arg Ser Cys Thr Ser Pro Ala Pro Ser Pro
            930                 935                 940

Gly Glu Asp Ile Cys Leu Gly Leu His Thr Glu Ala Leu Cys Ala
945                 950                 955                 960

Thr Gln Ala Cys Pro Glu Gly Trp Ser Pro Trp Ser Glu Trp Ser Lys
                965                 970                 975

Cys Thr Asp Asp Gly Ala Gln Ser Arg Ser Arg His Cys Glu Glu Leu
            980                 985                 990

Leu Pro Gly Ser Ser Ala Cys Ala Gly Asn Ser Ser Gln Ser Arg Pro
            995                 1000                1005

Cys Pro Tyr Ser Glu Ile Pro Val Ile Leu Pro Ala Ser Ser Met Glu
        1010                1015                1020

Glu Ala Thr Gly Cys Ala Gly Phe Asn Leu Ile His Leu Val Ala Thr
1025                1030                1035                1040

Gly Ile Ser Cys Phe Leu Gly Ser Gly Leu Leu Thr Leu Ala Val Tyr
                1045                1050                1055

Leu Ser Cys Gln His Cys Gln Arg Gln Ser Gln Glu Ser Thr Leu Val
            1060                1065                1070

His Pro Ala Thr Pro Asn His Leu His Tyr Lys Gly Gly Gly Thr Pro
            1075                1080                1085

Lys Asn Glu Lys Tyr Thr Pro Met Glu Phe Lys Thr Leu Asn Lys Asn
            1090                1095                1100

Asn Leu Ile Pro Asp Asp Arg Ala Asn Phe Tyr Pro Leu Gln Gln Thr
1105                1110                1115                1120

Asn Val Tyr Thr Thr Thr Tyr Tyr Pro Ser Pro Leu Asn Lys His Ser
                1125                1130                1135

Phe Arg Pro Glu Ala Ser Pro Gly Gln Arg Cys Phe Pro Asn Ser
            1140                1145                1150

<210> SEQ ID NO 11
<211> LENGTH: 3411
<212> TYPE: DNA
<213> ORGANISM: homo sapiens

<400> SEQUENCE: 11

| | | |
|---|---|---|
|atgccctgtg gcttcagtcc gtctcctgtt gcccaccacc tcgtccctgg gccgcctgat|60|
|acccagccc aacagctaag gtgtggatgg acagtagggg gctggcttct ctcactggtc|120|
|agggtcttc tccctgtct gcctcccgga gctaggactg cagagggcc tatcatggtg|180|
|cttgcaggcc cctggctgt ctcgctgttg ctgcccagcc tcacactgct ggtgtcccac|240|
|ctctccagct cccaggatgt ctccagtgag cccagcagtg agcagcagct gtgcgccctt|300|
|agcaagcacc ccaccgtggc cttttgaagac ctgcagccgt gggtctctaa cttcacctac|360|

-continued

```
cctggagccc gggatttctc ccagctggct ttggaccccct ccgggracca gctcatcgtg      420
ggagccagga actacctctt cagactcagc cttgccaatg tctctcttct tcaggccaca      480
gagtgggcct ccagtgagga cacgcgccgc tcctgccaaa gcaaagggaa gactgaggag      540
gagtgtcaga actacgtgcg agtcctgatc gtcgccggcc ggaaggtgtt catgtgtgga      600
accaatgcct tttcccccat gtgcaccagc agacaggtgg ggaacctcag ccggactatt      660
gagaagatca atggtgtggc ccgctgcccc tatgacccac gccacaactc cacagctgtc      720
atctcctccc aggggagct ctatgcagcc acggtcatcg acttctcagg tcgggaccct      780
gccatctacc gcagcctggg cagtgggcca ccgcttcgca ctgcccaata taactccaag      840
tggcttaatg agccaaactt cgtggcagcc tatgatattg gctgttttgc atacttcttc      900
ctgcgggaga acgcagtgga gcacgactgt ggacgcaccg tgtactctcg cgtggcccgc      960
gtgtgcaaga atgacgtggg gggccgattc ctgctggagg acacatggac cacattcatg     1020
aaggcccggc tcaactgctc ccgcccgggc gaggtcccct tctactataa cgagctgcag     1080
agtgccttcc acttgccrga gcaggacctc atctatggag ttttcacaac caacgtaaac     1140
agcatygcgg cttctgctgt ctgcgccttc aacctcagtg ctatctccca ggctttcaat     1200
ggcccatttc gctaccagga gaaccccagg gctgcctggc tccccatagc caaccccatc     1260
cccaatttcc agtgtggcac cctgcctgag accggtccca acgagaacct gacggagcgc     1320
agcctgcagg acgcgcagcg cctcttcctg atgagcgagg ccgtgcagcc ggtgacaccc     1380
gagccctgtg tcacccagga cagcgtgcgc ttctcacacc tcgtggtgga cctggtgcag     1440
gctaaagaca cgctctacca tgtactctac attggcaccg agtcgggcac catcctgaag     1500
gcgctgtcca cggcgagccg cagcctccac ggctgctacc tggaggagct gcacgtgctg     1560
ccccccgggc gccgcgagcc cctgcgcagc ctgcgcatcc tgcacagcgc ccgcgcgctc     1620
ttcgtggggc tgagagacgg cgtcctgcgg gtcccactgg agaggtgcgc cgcctaccgc     1680
agccaggggg catgcctggg ggcccgggac ccgtactgtg gctgggacgg gaagcagcaa     1740
cgttgcagca cactcgagga cagctccaac atgagcctct ggacccagaa catcaccgcc     1800
tgtcctgtgc ggaatgtgac acgggatggg ggcttcggcc catggtcacc atggcaacca     1860
tgtgagcact ggatggggga caactcaggc tcttgcctgt gtcgagctcg atcctgtgat     1920 tccctcgac cccgctgtgg gggccttgac tgcctggggc cagccatcca catcgccaac     1980
tgctccagga atggggcgtg gaccccgtgg tcatcgtggg cgctgtgcag cacgtcctgt     2040
ggcatcggct tccaggtccg ccagcgaagt tgcagcaacc ctgctccccg ccacggggggc     2100 cgcatctgcg tgggcaagag ccgggaggaa cggttctgta atgagaacac gccttgcccg     2160
gtgcccatct tctgggcttc ctgggggctcc tggagcaagt gcagcagcaa ctgtggagggg     2220 ggcatgcagt cgcggcgtcg ggcctgcgag aacggcaact cctgcctggg ctgcggcgtg     2280
gagttcaaga cgtgcaaccc cgagggctgc cccgaagtgc ggcgcaacac ccctggacg     2340 ccgtggctgc ccgtgaacgt gacgcagggc ggggcacggc aggagcagcg gttccgcttc     2400
acctgccgcg cgcccttgc agacccgcac ggcctgcagt tcggcaggag aaggaccgag     2460
acgaggacct gtccgcggga cggctccggc tcctgcgaca ccgacgccct ggtggaggac     2520
ctcctgcgca gcgggagcac ctcccccgca cacggtgagcg ggggctgggc cgcctggggc     2580
ccgtggtcgt cctgctcccg ggactgcgag ctgggcttcc gcgtccgcaa gagaacgtgc     2640 actaaccccgg agccccgcaa cggggggcctg ccctgcgtgg gcgatgctgc cgagtaccag     2700
gactgcaacc cccaggcttg cccagttcgg ggtgcttggt cctgctggac ctcatggtct     2760
```

```
ccatgctcag cttcctgtgg tgggggtcac tatcaacgca cccgttcctg caccagcccc   2820
gcaccctccc caggtgagga catctgtctc gggctgcaca cggaggaggc actatgtgcc   2880
acacaggcct gcccagaagg ctggtcgccc tggtctgagt ggagtaagtg cactgacgac   2940
ggagcccaga gccgaagccg gcactgtgag gagctcctcc cagggtccag cgcctgtgct   3000
ggaaacagca gccagagccg cccctgcccc tacagcgaga ttcccgggtt caatctcatc   3060
cacttggtgg ccacgggcat ctcctgcttc ttgggtctg gctcctgac cctagcagtg    3120 tacctgtctt gccagcactg ccagcgtcag tcccaggagt ccacactggt ccatcctgcc   3180
acccccaacc atttgcacta caaggcgga ggcaccccga agaatgaaaa gtacacaccc    3240
atggaattca agaccctgaa caagaataac ttgatccctg atgacagagc caacttctac   3300
ccattgcagc agaccaatgt gtacacgact acttactacc aagccccct gaacaaacac    3360 agcttccggc ccgaggcctc acctggacaa cggtgcttcc ccaacagctg a            3411
```

<210> SEQ ID NO 12
<211> LENGTH: 1136
<212> TYPE: PRT
<213> ORGANISM: homo sapiens

<400> SEQUENCE: 12

```
Met Pro Cys Gly Phe Ser Pro Ser Pro Val Ala His His Leu Val Pro
 1               5                  10                  15

Gly Pro Pro Asp Thr Pro Ala Gln Gln Leu Arg Cys Gly Trp Thr Val
            20                  25                  30

Gly Gly Trp Leu Leu Ser Leu Val Arg Gly Leu Leu Pro Cys Leu Pro
        35                  40                  45

Pro Gly Ala Arg Thr Ala Glu Gly Pro Ile Met Val Leu Ala Gly Pro
    50                  55                  60

Leu Ala Val Ser Leu Leu Leu Pro Ser Leu Thr Leu Leu Val Ser His
65                  70                  75                  80

Leu Ser Ser Ser Gln Asp Val Ser Ser Glu Pro Ser Glu Gln Gln
                85                  90                  95

Leu Cys Ala Leu Ser Lys His Pro Thr Val Ala Phe Glu Asp Leu Gln
            100                 105                 110

Pro Trp Val Ser Asn Phe Thr Tyr Pro Gly Ala Arg Asp Phe Ser Gln
        115                 120                 125

Leu Ala Leu Asp Pro Ser Gly Asn Gln Leu Ile Val Gly Ala Arg Asn
    130                 135                 140

Tyr Leu Phe Arg Leu Ser Leu Ala Asn Val Ser Leu Leu Gln Ala Thr
145                 150                 155                 160

Glu Trp Ala Ser Ser Glu Asp Thr Arg Arg Ser Cys Gln Ser Lys Gly
                165                 170                 175

Lys Thr Glu Glu Glu Cys Gln Asn Tyr Val Arg Val Leu Ile Val Ala
            180                 185                 190

Gly Arg Lys Val Phe Met Cys Gly Thr Asn Ala Phe Ser Pro Met Cys
        195                 200                 205

Thr Ser Arg Gln Val Gly Asn Leu Ser Arg Thr Ile Glu Lys Ile Asn
    210                 215                 220

Gly Val Ala Arg Cys Pro Tyr Asp Pro Arg His Asn Ser Thr Ala Val
225                 230                 235                 240

Ile Ser Ser Gln Gly Glu Leu Tyr Ala Ala Thr Val Ile Asp Phe Ser
                245                 250                 255
```

-continued

```
Gly Arg Asp Pro Ala Ile Tyr Arg Ser Leu Gly Ser Gly Pro Pro Leu
            260                 265                 270

Arg Thr Ala Gln Tyr Asn Ser Lys Trp Leu Asn Glu Pro Asn Phe Val
        275                 280                 285

Ala Ala Tyr Asp Ile Gly Leu Phe Ala Tyr Phe Phe Leu Arg Glu Asn
    290                 295                 300

Ala Val Glu His Asp Cys Gly Arg Thr Val Tyr Ser Arg Val Ala Arg
305                 310                 315                 320

Val Cys Lys Asn Asp Val Gly Arg Phe Leu Leu Glu Asp Thr Trp
                325                 330                 335

Thr Thr Phe Met Lys Ala Arg Leu Asn Cys Ser Arg Pro Gly Glu Val
            340                 345                 350

Pro Phe Tyr Tyr Asn Glu Leu Gln Ser Ala Phe His Leu Pro Glu Gln
        355                 360                 365

Asp Leu Ile Tyr Gly Val Phe Thr Thr Asn Val Asn Ser Ile Ala Ala
370                 375                 380

Ser Val Cys Ala Phe Asn Leu Ser Ala Ile Ser Gln Ala Phe Asn
385                 390                 395                 400

Gly Pro Phe Arg Tyr Gln Glu Asn Pro Arg Ala Ala Trp Leu Pro Ile
                405                 410                 415

Ala Asn Pro Ile Pro Asn Phe Gln Cys Gly Thr Leu Pro Glu Thr Gly
            420                 425                 430

Pro Asn Glu Asn Leu Thr Glu Arg Ser Leu Gln Asp Ala Gln Arg Leu
        435                 440                 445

Phe Leu Met Ser Glu Ala Val Gln Pro Val Thr Pro Glu Pro Cys Val
    450                 455                 460

Thr Gln Asp Ser Val Arg Phe Ser His Leu Val Val Asp Leu Val Gln
465                 470                 475                 480

Ala Lys Asp Thr Leu Tyr His Val Leu Tyr Ile Gly Thr Glu Ser Gly
                485                 490                 495

Thr Ile Leu Lys Ala Leu Ser Thr Ala Ser Arg Ser Leu His Gly Cys
            500                 505                 510

Tyr Leu Glu Glu Leu His Val Leu Pro Pro Gly Arg Arg Glu Pro Leu
        515                 520                 525

Arg Ser Leu Arg Ile Leu His Ser Ala Arg Ala Leu Phe Val Gly Leu
    530                 535                 540

Arg Asp Gly Val Leu Arg Val Pro Leu Glu Arg Cys Ala Ala Tyr Arg
545                 550                 555                 560

Ser Gln Gly Ala Cys Leu Gly Ala Arg Asp Pro Tyr Cys Gly Trp Asp
                565                 570                 575

Gly Lys Gln Gln Arg Cys Ser Thr Leu Glu Asp Ser Ser Asn Met Ser
            580                 585                 590

Leu Trp Thr Gln Asn Ile Thr Ala Cys Pro Val Arg Asn Val Thr Arg
        595                 600                 605

Asp Gly Gly Phe Gly Pro Trp Ser Pro Trp Gln Pro Cys Glu His Leu
    610                 615                 620

Asp Gly Asp Asn Ser Gly Ser Cys Leu Cys Arg Ala Arg Ser Cys Asp
625                 630                 635                 640

Ser Pro Arg Pro Arg Cys Gly Gly Leu Asp Cys Leu Gly Pro Ala Ile
                645                 650                 655

His Ile Ala Asn Cys Ser Arg Asn Gly Ala Trp Thr Pro Trp Ser Ser
            660                 665                 670
```

-continued

```
Trp Ala Leu Cys Ser Thr Ser Cys Gly Ile Gly Phe Gln Val Arg Gln
        675                 680                 685

Arg Ser Cys Ser Asn Pro Ala Pro Arg His Gly Gly Arg Ile Cys Val
    690                 695                 700

Gly Lys Ser Arg Glu Glu Arg Phe Cys Asn Glu Asn Thr Pro Cys Pro
705                 710                 715                 720

Val Pro Ile Phe Trp Ala Ser Trp Gly Ser Trp Ser Lys Cys Ser Ser
                725                 730                 735

Asn Cys Gly Gly Gly Met Gln Ser Arg Arg Arg Ala Cys Glu Asn Gly
                740                 745                 750

Asn Ser Cys Leu Gly Cys Gly Val Glu Phe Lys Thr Cys Asn Pro Glu
            755                 760                 765

Gly Cys Pro Glu Val Arg Arg Asn Thr Pro Trp Thr Pro Trp Leu Pro
        770                 775                 780

Val Asn Val Thr Gln Gly Gly Ala Arg Gln Glu Gln Arg Phe Arg Phe
785                 790                 795                 800

Thr Cys Arg Ala Pro Leu Ala Asp Pro His Gly Leu Gln Phe Gly Arg
                805                 810                 815

Arg Arg Thr Glu Thr Arg Thr Cys Pro Ala Asp Gly Ser Gly Ser Cys
                820                 825                 830

Asp Thr Asp Ala Leu Val Glu Asp Leu Leu Arg Ser Gly Ser Thr Ser
            835                 840                 845

Pro His Thr Val Ser Gly Gly Trp Ala Ala Trp Gly Pro Trp Ser Ser
        850                 855                 860

Cys Ser Arg Asp Cys Glu Leu Gly Phe Arg Val Arg Lys Arg Thr Cys
865                 870                 875                 880

Thr Asn Pro Glu Pro Arg Asn Gly Gly Leu Pro Cys Val Gly Asp Ala
                885                 890                 895

Ala Glu Tyr Gln Asp Cys Asn Pro Gln Ala Cys Pro Val Arg Gly Ala
                900                 905                 910

Trp Ser Cys Trp Thr Ser Trp Ser Pro Cys Ser Ala Ser Cys Gly Gly
            915                 920                 925

Gly His Tyr Gln Arg Thr Arg Ser Cys Thr Ser Pro Ala Pro Ser Pro
        930                 935                 940

Gly Glu Asp Ile Cys Leu Gly Leu His Thr Glu Glu Ala Leu Cys Ala
945                 950                 955                 960

Thr Gln Ala Cys Pro Glu Gly Trp Ser Pro Trp Ser Glu Trp Ser Lys
                965                 970                 975

Cys Thr Asp Asp Gly Ala Gln Ser Arg Ser Arg His Cys Glu Glu Leu
            980                 985                 990

Leu Pro Gly Ser Ser Ala Cys Ala Gly Asn Ser Ser Gln Ser Arg Pro
        995                 1000                1005

Cys Pro Tyr Ser Glu Ile Pro Gly Phe Asn Leu Ile His Leu Val Ala
        1010                1015                1020

Thr Gly Ile Ser Cys Phe Leu Gly Ser Gly Leu Leu Thr Leu Ala Val
1025                1030                1035                1040

Tyr Leu Ser Cys Gln His Cys Gln Arg Gln Ser Gln Glu Ser Thr Leu
                1045                1050                1055

Val His Pro Ala Thr Pro Asn His Leu His Tyr Lys Gly Gly Gly Thr
            1060                1065                1070

Pro Lys Asn Glu Lys Tyr Thr Pro Met Glu Phe Lys Thr Leu Asn Lys
        1075                1080                1085
```

| Asn | Asn | Leu | Ile | Pro | Asp | Asp | Arg | Ala | Asn | Phe | Tyr | Pro | Leu | Gln | Gln |
| | 1090 | | | | 1095 | | | | 1100 | | | | | | |

| Thr | Asn | Val | Tyr | Thr | Thr | Thr | Tyr | Tyr | Pro | Ser | Pro | Leu | Asn | Lys | His |
| 1105 | | | | | 1110 | | | | | 1115 | | | | | 1120 |

| Ser | Phe | Arg | Pro | Glu | Ala | Ser | Pro | Gly | Gln | Arg | Cys | Phe | Pro | Asn | Ser |
| | | | 1125 | | | | | 1130 | | | | | 1135 | | |

<210> SEQ ID NO 13
<211> LENGTH: 2865
<212> TYPE: DNA
<213> ORGANISM: homo sapiens

<400> SEQUENCE: 13

```
atgtgtggaa ccaatgcctt tccccccatg tgcaccagca gacaggtggg gaacctcagc      60
cggactattg agaagatcaa tggtgtggcc cgctgcccct atgacccacg ccacaactcc     120
acagctgtca tctcctccca gggggagctc tatgcagcca cggtcatcga cttctcaggt     180
cgggaccctg ccatctaccg cagcctgggc agtgggccac cgcttcgcac tgcccaatat     240
aactccaagt ggcttaatga gccaaacttc gtggcagcct atgatattgg gctgtttgca     300
tacttcttcc tgcgggagaa cgcagtggag cacgactgtg gacgcaccgt gtactctcgc     360
gtggcccgcg tgtgcaagaa tgacgtgggg ggccgattcc tgctggagga cacatggacc     420
acattcatga aggcccggct caactgctcc cgcccgggcg aggtcccctt ctactataac     480
gagctgcaga gtgccttcca cttgccrgag caggacctca tctatggagt tttcacaacc     540
aacgtaaaca gcatygcggc ttctgctgtc tgcgccttca acctcagtgc tatctcccag     600
gctttcaatg gcccatttcg ctaccaggag aaccccaggg ctgcctggct ccccatagcc     660
aaccccatcc ccaatttcca gtgtggcacc ctgcctgaga ccggtcccaa cgagaacctg     720
acggagcgca gcctgcagga cgcgcagcgc ctcttcctga tgagcgaggc cgtgcagccg     780
gtgacacccg agcctgtgt cacccaggac agcgtgcgct tctcacacct cgtggtggac     840
ctggtgcagg ctaaagacac gctctaccat gtactctaca ttggcaccga gtcgggcacc     900
atcctgaagg cgctgtccac ggcgagccgc agcctccacg gctgctacct ggaggagctg     960
cacgtgctgc cccccgggcg ccgcgagccc ctgcgcagcc tgcgcatcct gcacagcgcc    1020
cgcgcgctct tcgtggggct gagagacggc gtcctgcggg tcccactgga gaggtgcgcc    1080
gcctaccgca gccaggggagc atgcctgggg gcccgggacc cgtactgtgg ctgggacggg    1140
aagcagcaac gttgcagcac actcgaggac agctccaaca tgagcctctg gacccagaac    1200
atcaccgcct gtcctgtgcg gaatgtgaca cgggatgggg gcttcggccc atggtcacca    1260
tggcaaccat gtgagcactt ggatggggac aactcaggct cttgcctgtg tcgagctcga    1320
tcctgtgatt cccctcgacc ccgctgtggg ggccttgact gcctggggcc agccatccac    1380
atcgccaact gctccaggaa tggggcgtgg acccgtggt catcgtgggc gctgtgcagc    1440
acgtcctgtg gcatcggctt ccaggtccgc cagcgaagtt gcagcaaccc tgctccccgc    1500
cacgggggcc gcatctgcgt gggcaagagc cggaggaac ggttctgtaa tgagaacacg    1560
ccttgcccgg tgcccatctt ctgggcttcc tggggctcct ggagcaagtg cagcagcaac    1620
tgtggagggg gcatgcagtc gcggcgtcgg gcctgcgaga acggcaactc ctgcctgggc    1680
tgcggcgtgg agttcaagac gtgcaacccc gagggctgcc ccgaagtgcg gcgcaacacc    1740
ccctggacgc cgtggctgcc cgtgaacgtg acgcaggggcg gggcacggca ggagcagcgg    1800
ttccgcttca cctgccgcgc gccccttgca gacccgcacg gcctgcagtt cggcaggaga    1860
```

-continued

```
aggaccgaga cgaggacctg tcccgcggac ggctccggct cctgcgacac cgacgccctg      1920
gtggaggacc tcctgcgcag cgggagcacc tccccgcaca cggtgagcgg gggctgggcc      1980
gcctggggcc cgtggtcgtc ctgctcccgg gactgcgagc tgggcttccg cgtccgcaag      2040
agaacgtgca ctaaccccgga gccccgcaac gggggcctgc cctgcgtggg cgatgctgcc     2100
gagtaccagg actgcaaccc ccaggcttgc ccagttcggg gtgcttggtc ctgctggacc      2160
tcatggtctc catgctcagc ttcctgtggt ggggtcact atcaacgcac ccgttcctgc       2220
accagccccg cacctccc aggtgaggac atctgtctcg gctgcacac ggaggaggca         2280
ctatgtgcca cacaggcctg cccagaaggc tggtcgccct ggtctgagtg gagtaagtgc      2340
actgacgacg gagcccagag ccgaagccgg cactgtgagg agctcctccc agggtccagc      2400
gcctgtgctg aaacagcag ccagagccgc ccctgcccct acagcgagat tcccgtcatc       2460
ctgccagcct ccagcatgga ggaggccacc ggctgtgcag ggttcaatct catccacttg      2520
gtggccacgg gcatctcctg cttcttgggc tctgggctcc tgaccctagc agtgtacctg      2580
tcttgccagc actgccagcg tcagtcccag gagtccacac tggtccatcc tgccaccccc     2640
aaccatttgc actacaaggg cggaggcacc ccgaagaatg aaaagtacac acccatggaa      2700
ttcaagaccc tgaacaagaa taacttgatc cctgatgaca gagccaactt ctacccattg      2760
cagcagacca atgtgtacac gactacttac tacccaagcc ccctgaacaa acacagcttc      2820
cggcccgagg cctcacctgg acaacggtgc ttccccaaca gctga                     2865
```

<210> SEQ ID NO 14
<211> LENGTH: 954
<212> TYPE: PRT
<213> ORGANISM: homo sapiens

<400> SEQUENCE: 14

```
Met Cys Gly Thr Asn Ala Phe Ser Pro Met Cys Thr Ser Arg Gln Val
 1               5                  10                  15

Gly Asn Leu Ser Arg Thr Ile Glu Lys Ile Asn Gly Val Ala Arg Cys
             20                  25                  30

Pro Tyr Asp Pro Arg His Asn Ser Thr Ala Val Ile Ser Ser Gln Gly
         35                  40                  45

Glu Leu Tyr Ala Ala Thr Val Ile Asp Phe Ser Gly Arg Asp Pro Ala
     50                  55                  60

Ile Tyr Arg Ser Leu Gly Ser Gly Pro Pro Leu Arg Thr Ala Gln Tyr
 65                  70                  75                  80

Asn Ser Lys Trp Leu Asn Glu Pro Asn Phe Val Ala Ala Tyr Asp Ile
                 85                  90                  95

Gly Leu Phe Ala Tyr Phe Phe Leu Arg Glu Asn Ala Val Glu His Asp
            100                 105                 110

Cys Gly Arg Thr Val Tyr Ser Arg Val Ala Arg Val Cys Lys Asn Asp
        115                 120                 125

Val Gly Gly Arg Phe Leu Leu Glu Asp Thr Trp Thr Thr Phe Met Lys
    130                 135                 140

Ala Arg Leu Asn Cys Ser Arg Pro Gly Glu Val Pro Phe Tyr Tyr Asn
145                 150                 155                 160

Glu Leu Gln Ser Ala Phe His Leu Pro Glu Gln Asp Leu Ile Tyr Gly
                165                 170                 175

Val Phe Thr Thr Asn Val Asn Ser Ile Ala Ala Ser Ala Val Cys Ala
            180                 185                 190
```

-continued

```
Phe Asn Leu Ser Ala Ile Ser Gln Ala Phe Asn Gly Pro Phe Arg Tyr
            195                 200                 205

Gln Glu Asn Pro Arg Ala Ala Trp Leu Pro Ile Ala Asn Pro Ile Pro
        210                 215                 220

Asn Phe Gln Cys Gly Thr Leu Pro Glu Thr Gly Pro Asn Glu Asn Leu
225                 230                 235                 240

Thr Glu Arg Ser Leu Gln Asp Ala Gln Arg Leu Phe Leu Met Ser Glu
                245                 250                 255

Ala Val Gln Pro Val Thr Pro Glu Pro Cys Val Thr Gln Asp Ser Val
            260                 265                 270

Arg Phe Ser His Leu Val Val Asp Leu Val Gln Ala Lys Asp Thr Leu
        275                 280                 285

Tyr His Val Leu Tyr Ile Gly Thr Glu Ser Gly Thr Ile Leu Lys Ala
    290                 295                 300

Leu Ser Thr Ala Ser Arg Ser Leu His Gly Cys Tyr Leu Glu Glu Leu
305                 310                 315                 320

His Val Leu Pro Pro Gly Arg Arg Glu Pro Leu Arg Ser Leu Arg Ile
                325                 330                 335

Leu His Ser Ala Arg Ala Leu Phe Val Gly Leu Arg Asp Gly Val Leu
            340                 345                 350

Arg Val Pro Leu Glu Arg Cys Ala Ala Tyr Arg Ser Gln Gly Ala Cys
        355                 360                 365

Leu Gly Ala Arg Asp Pro Tyr Cys Gly Trp Asp Gly Lys Gln Gln Arg
    370                 375                 380

Cys Ser Thr Leu Glu Asp Ser Ser Asn Met Ser Leu Trp Thr Gln Asn
385                 390                 395                 400

Ile Thr Ala Cys Pro Val Arg Asn Val Thr Arg Asp Gly Gly Phe Gly
                405                 410                 415

Pro Trp Ser Pro Trp Gln Pro Cys Glu His Leu Asp Gly Asp Asn Ser
            420                 425                 430

Gly Ser Cys Leu Cys Arg Ala Arg Ser Cys Asp Ser Pro Arg Pro Arg
        435                 440                 445

Cys Gly Gly Leu Asp Cys Leu Gly Pro Ala Ile His Ile Ala Asn Cys
    450                 455                 460

Ser Arg Asn Gly Ala Trp Thr Pro Trp Ser Ser Trp Ala Leu Cys Ser
465                 470                 475                 480

Thr Ser Cys Gly Ile Gly Phe Gln Val Arg Gln Arg Ser Cys Ser Asn
                485                 490                 495

Pro Ala Pro Arg His Gly Gly Arg Ile Cys Val Gly Lys Ser Arg Glu
            500                 505                 510

Glu Arg Phe Cys Asn Glu Asn Thr Pro Cys Pro Val Pro Ile Phe Trp
        515                 520                 525

Ala Ser Trp Gly Ser Trp Ser Lys Cys Ser Ser Asn Cys Gly Gly Gly
    530                 535                 540

Met Gln Ser Arg Arg Arg Ala Cys Glu Asn Gly Asn Ser Cys Leu Gly
545                 550                 555                 560

Cys Gly Val Glu Phe Lys Thr Cys Asn Pro Glu Gly Cys Pro Glu Val
                565                 570                 575

Arg Arg Asn Thr Pro Trp Thr Pro Trp Leu Pro Val Asn Val Thr Gln
            580                 585                 590

Gly Gly Ala Arg Gln Glu Gln Arg Phe Arg Phe Thr Cys Arg Ala Pro
        595                 600                 605
```

```
Leu Ala Asp Pro His Gly Leu Gln Phe Gly Arg Arg Thr Glu Thr
    610                 615                 620
Arg Thr Cys Pro Ala Asp Gly Ser Gly Ser Cys Asp Thr Asp Ala Leu
625                 630                 635                 640
Val Glu Asp Leu Leu Arg Ser Gly Ser Thr Ser Pro His Thr Val Ser
                    645                 650                 655
Gly Gly Trp Ala Ala Trp Gly Pro Trp Ser Ser Cys Ser Arg Asp Cys
                660                 665                 670
Glu Leu Gly Phe Arg Val Arg Lys Arg Thr Cys Thr Asn Pro Glu Pro
            675                 680                 685
Arg Asn Gly Gly Leu Pro Cys Val Gly Asp Ala Ala Glu Tyr Gln Asp
    690                 695                 700
Cys Asn Pro Gln Ala Cys Pro Val Arg Gly Ala Trp Ser Cys Trp Thr
705                 710                 715                 720
Ser Trp Ser Pro Cys Ser Ala Ser Cys Gly Gly Gly His Tyr Gln Arg
                    725                 730                 735
Thr Arg Ser Cys Thr Ser Pro Ala Pro Ser Pro Gly Glu Asp Ile Cys
                740                 745                 750
Leu Gly Leu His Thr Glu Glu Ala Leu Cys Ala Thr Gln Ala Cys Pro
            755                 760                 765
Glu Gly Trp Ser Pro Trp Ser Glu Trp Ser Lys Cys Thr Asp Asp Gly
    770                 775                 780
Ala Gln Ser Arg Ser Arg His Cys Glu Glu Leu Leu Pro Gly Ser Ser
785                 790                 795                 800
Ala Cys Ala Gly Asn Ser Ser Gln Ser Arg Pro Cys Pro Tyr Ser Glu
                    805                 810                 815
Ile Pro Val Ile Leu Pro Ala Ser Ser Met Glu Glu Ala Thr Gly Cys
                820                 825                 830
Ala Gly Phe Asn Leu Ile His Leu Val Ala Thr Gly Ile Ser Cys Phe
            835                 840                 845
Leu Gly Ser Gly Leu Leu Thr Leu Ala Val Tyr Leu Ser Cys Gln His
    850                 855                 860
Cys Gln Arg Gln Ser Gln Glu Ser Thr Leu Val His Pro Ala Thr Pro
865                 870                 875                 880
Asn His Leu His Tyr Lys Gly Gly Thr Pro Lys Asn Glu Lys Tyr
                    885                 890                 895
Thr Pro Met Glu Phe Lys Thr Leu Asn Lys Asn Asn Leu Ile Pro Asp
                900                 905                 910
Asp Arg Ala Asn Phe Tyr Pro Leu Gln Gln Thr Asn Val Tyr Thr Thr
            915                 920                 925
Thr Tyr Tyr Pro Ser Pro Leu Asn Lys His Ser Phe Arg Pro Glu Ala
    930                 935                 940
Ser Pro Gly Gln Arg Cys Phe Pro Asn Ser
945                 950
```

<210> SEQ ID NO 15
<211> LENGTH: 2820
<212> TYPE: DNA
<213> ORGANISM: homo sapiens

<400> SEQUENCE: 15

```
atgtgtggaa ccaatgcctt tccccccatg tgcaccagca gacaggtggg gaacctcagc      60
cggactattg agaagatcaa tggtgtggcc cgctgcccct atgacccacg ccacaactcc     120
acagctgtca tctcctccca gggggagctc tatgcagcca cggtcatcga cttctcaggt     180
```

-continued

| | |
|---|---|
| cgggaccctg ccatctaccg cagcctgggc agtgggccac cgcttcgcac tgcccaatat | 240 |
| aactccaagt ggcttaatga gccaaacttc gtggcagcct atgatattgg gctgtttgca | 300 |
| tacttcttcc tgcgggagaa cgcagtggag cacgactgtg gacgcaccgt gtactctcgc | 360 |
| gtggcccgcg tgtgcaagaa tgacgtgggg ggccgattcc tgctggagga cacatggacc | 420 |
| acattcatga aggcccggct caactgctcc cgcccgggcg aggtccccctt ctactataac | 480 |
| gagctgcaga gtgccttcca cttgccrgag caggacctca tctatggagt tttcacaacc | 540 |
| aacgtaaaca gcatygcggc ttctgctgtc tgcgccttca acctcagtgc tatctcccag | 600 |
| gctttcaatg gcccatttcg ctaccaggag aaccccaggg ctgcctggct ccccatagcc | 660 |
| aaccccatcc ccaatttcca gtgtggcacc ctgcctgaga ccggtcccaa cgagaacctg | 720 |
| acggagcgca gcctgcagga cgcgcagcgc ctcttcctga tgagcgaggc cgtgcagccg | 780 |
| gtgacacccg agccctgtgt cacccaggac agcgtgcgct tctcacacct cgtggtggac | 840 |
| ctggtgcagg ctaaagacac gctctaccat gtactctaca ttggcaccga gtcgggcacc | 900 |
| atcctgaagg cgctgtccac ggcgagccgc agcctccacg gctgctacct ggaggagctg | 960 |
| cacgtgctgc cccccgggcg ccgcgagccc ctgcgcagcc tgcgcatcct gcacagcgcc | 1020 |
| cgcgcgctct tcgtggggct gagagacggc gtcctgcggg tcccactgga gaggtgcgcc | 1080 |
| gcctaccgca gccaggggggc atgcctgggg gcccgggacc cgtactgtgg ctgggacggg | 1140 |
| aagcagcaac gttgcagcac actcgaggac agctccaaca tgagcctctg acccagaac | 1200 |
| atcaccgcct gtcctgtgcg gaatgtgaca cgggatgggg gcttcggccc atggtcacca | 1260 |
| tggcaaccat gtgagcactt ggatggggac aactcaggct cttgcctgtg tcgagctcga | 1320 |
| tcctgtgatt cccctcgacc ccgctgtggg ggccttgact gcctggggcc agccatccac | 1380 |
| atcgccaact gctccaggaa tggggcgtgg accccgtggt catcgtgggc gctgtgcagc | 1440 |
| acgtcctgtg gcatcggctt ccaggtccgc cagcgaagtt gcagcaaccc tgctccccgc | 1500 |
| cacgggggcc gcatctgcgt gggcaagagc cgggaggaac ggttctgtaa tgagaacacg | 1560 |
| ccttgcccgg tgcccatctt ctgggcttcc tggggctcct ggagcaagtg cagcagcaac | 1620 |
| tgtggagggg gcatgcagtc gcggcgtcgg gcctgcgaga acggcaactc ctgcctgggc | 1680 |
| tgcggcgtgg agttcaagac gtgcaacccc gagggctgcc ccgaagtgcg gcgcaacacc | 1740 |
| ccctggacgc cgtggctgcc cgtgaacgtg acgcagggcg gggcacggca ggagcagcgg | 1800 |
| ttccgcttca cctgccgcgc gccccttgca gacccgcacg gcctgcagtt cggcaggaga | 1860 |
| aggaccgaga cgaggacctg tcccgcggac ggctccggcc cctgcgacac cgacgccctg | 1920 |
| gtggaggacc tcctgcgcag cgggagcacc tccccgcaca cggtgagcgg gggctgggcc | 1980 |
| gcctgggggcc cgtggtcgtc ctgctcccgg gactgcgagc tgggcttccg cgtccgcaag | 2040 |
| agaacgtgca ctaacccgga gccccgcaac gggggcctgc cctgcgtggg cgatgctgcc | 2100 |
| gagtaccagg actgcaaccc ccaggcttgc ccagttcggg gtgcttggtc ctgctggacc | 2160 |
| tcatggtctc catgctcagc ttcctgtggt gggggtcact atcaacgcac ccgttcctgc | 2220 |
| accagccccg caccctcccc aggtgaggac atctgtctcg gctgcacac ggaggaggca | 2280 |
| ctatgtgcca cacaggcctg cccagaaggc tggtcgccct ggtctgagtg gagtaagtgc | 2340 |
| actgacgacg gagcccagag ccgaagccgg cactgtgagg agctcctccc agggtccagc | 2400 |
| gcctgtgctg gaaacagcag ccagagccgc ccctgcccct acagcgagat tcccgggttc | 2460 |
| aatctcatcc acttggtggc cacgggcatc tcctgcttct gggctctgg gctcctgacc | 2520 |
| ctagcagtgt acctgtcttg ccagcactgc cagcgtcagt cccaggagtc cacactggtc | 2580 |

-continued

```
catcctgcca ccccccaacca tttgcactac aagggcggag gcaccccgaa gaatgaaaag    2640
tacacaccca tggaattcaa gaccctgaac aagaataact tgatccctga tgacagagcc    2700
aacttctacc cattgcagca gaccaatgtg tacacgacta cttactaccc aagcccctg     2760 aacaaacaca gcttccggcc cgaggcctca cctggacaac ggtgcttccc caacagctga    2820
```

<210> SEQ ID NO 16
<211> LENGTH: 939
<212> TYPE: PRT
<213> ORGANISM: homo sapiens

<400> SEQUENCE: 16

```
Met Cys Gly Thr Asn Ala Phe Ser Pro Met Cys Thr Ser Arg Gln Val
  1               5                  10                  15

Gly Asn Leu Ser Arg Thr Ile Glu Lys Ile Asn Gly Val Ala Arg Cys
             20                  25                  30

Pro Tyr Asp Pro Arg His Asn Ser Thr Ala Val Ile Ser Ser Gln Gly
         35                  40                  45

Glu Leu Tyr Ala Ala Thr Val Ile Asp Phe Ser Gly Arg Asp Pro Ala
     50                  55                  60

Ile Tyr Arg Ser Leu Gly Ser Gly Pro Pro Leu Arg Thr Ala Gln Tyr
 65                  70                  75                  80

Asn Ser Lys Trp Leu Asn Glu Pro Asn Phe Val Ala Ala Tyr Asp Ile
                 85                  90                  95

Gly Leu Phe Ala Tyr Phe Phe Leu Arg Glu Asn Ala Val Glu His Asp
            100                 105                 110

Cys Gly Arg Thr Val Tyr Ser Arg Val Ala Arg Val Cys Lys Asn Asp
        115                 120                 125

Val Gly Gly Arg Phe Leu Leu Glu Asp Thr Trp Thr Thr Phe Met Lys
    130                 135                 140

Ala Arg Leu Asn Cys Ser Arg Pro Gly Glu Val Pro Phe Tyr Tyr Asn
145                 150                 155                 160

Glu Leu Gln Ser Ala Phe His Leu Pro Glu Gln Asp Leu Ile Tyr Gly
                165                 170                 175

Val Phe Thr Thr Asn Val Asn Ser Ile Ala Ala Ser Ala Val Cys Ala
            180                 185                 190

Phe Asn Leu Ser Ala Ile Ser Gln Ala Phe Asn Gly Pro Phe Arg Tyr
        195                 200                 205

Gln Glu Asn Pro Arg Ala Ala Trp Leu Pro Ile Ala Asn Pro Ile Pro
    210                 215                 220

Asn Phe Gln Cys Gly Thr Leu Pro Glu Thr Gly Pro Asn Glu Asn Leu
225                 230                 235                 240

Thr Glu Arg Ser Leu Gln Asp Ala Gln Arg Leu Phe Leu Met Ser Glu
                245                 250                 255

Ala Val Gln Pro Val Thr Pro Glu Pro Cys Val Thr Gln Asp Ser Val
            260                 265                 270

Arg Phe Ser His Leu Val Val Asp Leu Val Gln Ala Lys Asp Thr Leu
        275                 280                 285

Tyr His Val Leu Tyr Ile Gly Thr Glu Ser Gly Thr Ile Leu Lys Ala
    290                 295                 300

Leu Ser Thr Ala Ser Arg Ser Leu His Gly Cys Tyr Leu Glu Glu Leu
305                 310                 315                 320

His Val Leu Pro Pro Gly Arg Arg Glu Pro Leu Arg Ser Leu Arg Ile
                325                 330                 335
```

-continued

```
Leu His Ser Ala Arg Ala Leu Phe Val Gly Leu Arg Asp Gly Val Leu
            340                 345                 350
Arg Val Pro Leu Glu Arg Cys Ala Ala Tyr Arg Ser Gln Gly Ala Cys
        355                 360                 365
Leu Gly Ala Arg Asp Pro Tyr Cys Gly Trp Asp Gly Lys Gln Gln Arg
    370                 375                 380
Cys Ser Thr Leu Glu Asp Ser Ser Asn Met Ser Leu Trp Thr Gln Asn
385                 390                 395                 400
Ile Thr Ala Cys Pro Val Arg Asn Val Thr Arg Asp Gly Phe Gly
            405                 410                 415
Pro Trp Ser Pro Trp Gln Pro Cys Glu His Leu Asp Gly Asp Asn Ser
        420                 425                 430
Gly Ser Cys Leu Cys Arg Ala Arg Ser Cys Asp Ser Pro Arg Pro Arg
    435                 440                 445
Cys Gly Gly Leu Asp Cys Leu Gly Pro Ala Ile His Ile Ala Asn Cys
450                 455                 460
Ser Arg Asn Gly Ala Trp Thr Pro Trp Ser Ser Trp Ala Leu Cys Ser
465                 470                 475                 480
Thr Ser Cys Gly Ile Gly Phe Gln Val Arg Gln Arg Ser Cys Ser Asn
            485                 490                 495
Pro Ala Pro Arg His Gly Gly Arg Ile Cys Val Gly Lys Ser Arg Glu
        500                 505                 510
Glu Arg Phe Cys Asn Glu Asn Thr Pro Cys Pro Val Pro Ile Phe Trp
    515                 520                 525
Ala Ser Trp Gly Ser Trp Ser Lys Cys Ser Ser Asn Cys Gly Gly Gly
    530                 535                 540
Met Gln Ser Arg Arg Ala Cys Glu Asn Gly Asn Ser Cys Leu Gly
545                 550                 555                 560
Cys Gly Val Glu Phe Lys Thr Cys Asn Pro Glu Gly Cys Pro Glu Val
            565                 570                 575
Arg Arg Asn Thr Pro Trp Thr Pro Trp Leu Pro Val Asn Val Thr Gln
        580                 585                 590
Gly Gly Ala Arg Gln Glu Gln Arg Phe Arg Phe Thr Cys Arg Ala Pro
    595                 600                 605
Leu Ala Asp Pro His Gly Leu Gln Phe Gly Arg Arg Thr Glu Thr
    610                 615                 620
Arg Thr Cys Pro Ala Asp Gly Ser Gly Ser Cys Asp Thr Asp Ala Leu
625                 630                 635                 640
Val Glu Asp Leu Leu Arg Ser Gly Ser Thr Ser Pro His Thr Val Ser
            645                 650                 655
Gly Gly Trp Ala Ala Trp Gly Pro Trp Ser Ser Cys Ser Arg Asp Cys
        660                 665                 670
Glu Leu Gly Phe Arg Val Arg Lys Arg Thr Cys Thr Asn Pro Glu Pro
    675                 680                 685
Arg Asn Gly Gly Leu Pro Cys Val Gly Asp Ala Ala Glu Tyr Gln Asp
    690                 695                 700
Cys Asn Pro Gln Ala Cys Pro Val Arg Gly Ala Trp Ser Cys Trp Thr
705                 710                 715                 720
Ser Trp Ser Pro Cys Ser Ala Ser Cys Gly Gly Gly His Tyr Gln Arg
            725                 730                 735
Thr Arg Ser Cys Thr Ser Pro Ala Pro Ser Pro Gly Glu Asp Ile Cys
        740                 745                 750
```

```
Leu Gly Leu His Thr Glu Glu Ala Leu Cys Ala Thr Gln Ala Cys Pro
        755                 760                 765
Glu Gly Trp Ser Pro Trp Ser Glu Trp Ser Lys Cys Thr Asp Asp Gly
    770                 775                 780
Ala Gln Ser Arg Ser Arg His Cys Glu Glu Leu Leu Pro Gly Ser Ser
785                 790                 795                 800
Ala Cys Ala Gly Asn Ser Ser Gln Ser Arg Pro Cys Pro Tyr Ser Glu
                805                 810                 815
Ile Pro Gly Phe Asn Leu Ile His Leu Val Ala Thr Gly Ile Ser Cys
            820                 825                 830
Phe Leu Gly Ser Gly Leu Leu Thr Leu Ala Val Tyr Leu Ser Cys Gln
        835                 840                 845
His Cys Gln Arg Gln Ser Gln Glu Ser Thr Leu Val His Pro Ala Thr
    850                 855                 860
Pro Asn His Leu His Tyr Lys Gly Gly Thr Pro Lys Asn Glu Lys
865                 870                 875                 880
Tyr Thr Pro Met Glu Phe Lys Thr Leu Asn Lys Asn Leu Ile Pro
                885                 890                 895
Asp Asp Arg Ala Asn Phe Tyr Pro Leu Gln Gln Thr Asn Val Tyr Thr
            900                 905                 910
Thr Thr Tyr Tyr Pro Ser Pro Leu Asn Lys His Ser Phe Arg Pro Glu
        915                 920                 925
Ala Ser Pro Gly Gln Arg Cys Phe Pro Asn Ser
    930                 935

<210> SEQ ID NO 17
<211> LENGTH: 4074
<212> TYPE: DNA
<213> ORGANISM: homo sapiens

<400> SEQUENCE: 17
cccgcggtct cctcctccct gctctctccg agcgccgggt cgggagctag ttggagcgcg       60
ggggttggtg ccagagccca gctccgccga gccgggcggg tcggcagcgc atccagcggc      120
tgctgggagc ccgagcgcag cgggcgcggg cccggtgggg gactgcaccg gagcgctgag      180
agctggaggc cgttcctgcg cggccgcccc attcccagac cggccgccag cccatctggt      240
tagctcccgc cgctccgcgc cgcccgggag tcggagccg cggggaaccg ggcacctgca      300
cccgcctctg ggaggtcttc tccctgtct gcctcccgga gctaggactg cagaggggcc      360
tatcatggtg cttgcaggcc ccctggctgt ctcgctgttg ctgcccagcc tcacactgct      420
ggtgtcccac ctctccagct cccaggatgt ctccagtgag cccagcagtg agcagcagct      480
gtgcgccctt agcaagcacc ccaccgtggc ctttgaagac ctgcagccgt gggtctctaa      540
cttcacctac cctggagccc ggatttctc ccagctggct ttggaccct ccgggracca      600
gctcatcgtg ggagccagga actacctctt cagactcagc cttgccaatg tctctcttct      660
tcaggccaca gagtgggcct ccagtgagga cacgcgccgc tcctgccaaa gcaaagggaa      720
gactgaggag gagtgtcaga actacgtgcg agtcctgatc gtcgccggcc ggaaggtgtt      780
catgtgtgga accaatgcct ttccccat gtgcaccagc agacaggtgg ggaacctcag      840
ccggactatt gagaagatca atggtgtggc ccgctgcccc atgacccac gccacaactc      900
cacagctgtc atctcctccc aggggagct ctatgcagcc acgtcatcg acttctcagg      960
tcgggaccct gccatctacc gcagcctggg cagtgggcca ccgcttcgca ctgcccaata     1020
taactccaag tggcttaatg agccaaactt cgtggcagcc tatgatattg gctgtttgc     1080
```

-continued

```
atacttcttc ctgcgggaga acgcagtgga gcacgactgt ggacgcaccg tgtactctcg    1140
cgtggcccgc gtgtgcaaga atgacgtggg gggccgattc ctgctggagg acacatggac    1200
cacattcatg aaggcccggc tcaactgctc ccgcccgggc gaggtcccct tctactataa    1260
cgagctgcag agtgccttcc acttgccrga gcaggacctc atctatggag ttttcacaac    1320
caacgtaaac agcatygcgg cttctgctgt ctgcgccttc aacctcagtg ctatctccca    1380
ggctttcaat ggcccatttc gctaccagga gaaccccagg gctgcctggc tccccatagc    1440 caacccatc cccaatttcc agtgtggcac cctgcctgag accggtccca acgagaacct    1500
gacggagcgc agcctgcagg acgcgcagcg cctcttcctg atgagcgagg ccgtgcagcc    1560
ggtgacaccc gagccctgtg tcacccagga cagcgtgcgc ttctcacacc tcgtggtgga    1620
cctggtgcag gctaaagaca cgctctacca tgtactctac attggcaccg agtcgggcac    1680
catcctgaag gcgctgtcca cggcgagccg cagcctccac ggctgctacc tggaggagct    1740
gcacgtgctg ccccccgggc gccgcgagcc cctgcgcagc ctgcgcatcc tgcacagcgc    1800
ccgcgcgctc ttcgtggggc tgagagacgg cgtcctgcgg gtcccactgg agaggtgcgc    1860
cgcctaccgc agccagggg catgcctggg ggcccgggac ccgtactgtg gctgggacgg    1920
gaagcagcaa cgttgcagca cactcgagga cagctccaac atgagcctct ggacccagaa    1980
catcaccgcc tgtcctgtgc ggaatgtgac acgggatggg ggcttcggcc catggtcacc    2040
atggcaacca tgtgagcact ggatgggga caactcaggc tcttgcctgt gtcgagctcg    2100
atcctgtgat tcccctcgac cccgctgtgg gggccttgac tgcctggggc cagccatcca    2160
catcgccaac tgctccagga atgggcgtg accccgtgg tcatcgtggg cgctgtgcag    2220
cacgtcctgt ggcatcggct tccaggtccg ccagcgaagt tgcagcaacc ctgctccccg    2280 ccacggggc cgcatctgcg tgggcaagag ccgggaggaa cggttctgta atgagaacac    2340
gccttgcccg gtgcccatct tctgggcttc ctggggctcc tggagcaagt gcagcagcaa    2400
ctgtggaggg ggcatgcagt cgcggcgtcg ggcctgcgag aacggcaact cctgcctggg    2460
ctgcggcgtg gagttcaaga cgtgcaaccc cgagggctgc cccgaagtgc ggcgcaacac    2520
cccctggacg ccgtggctgc ccgtgaacgt gacgcagggc ggggcacggc aggagcagcg    2580
gttccgcttc acctgccgcg cgcccccttgc agacccgcac ggcctgcagt tcggcaggag    2640
aaggaccgag acgaggacct gtcccgcgga cggctccggc tcctgcgaca ccgacgccct    2700
ggtggaggac ctcctgcgca gcgggagcac ctccccgcac acggtgagcg ggggctgggc    2760 cgcctgggc ccgtggtcgt cctgctcccg ggactgcgag ctgggcttcc gcgtccgcaa    2820
gagaacgtgc actaaccccgg agccccgcaa cggggcctg ccctgcgtgg gcgatgctgc    2880
cgagtaccag gactgcaacc cccaggcttg cccagttcgg ggtgcttggt cctgctggac    2940
ctcatggtct ccatgctcag cttcctgtgg tggggtcac tatcaacgca cccgttcctg    3000
caccagcccc gcaccctccc caggtgagga catctgtctc gggctgcaca cggaggaggc    3060
actatgtgcc acacaggcct gcccagaagg ctggtcgccc tggtctgagt ggagtaagtg    3120
cactgacgac ggagcccaga gccgaagccg cactgtgag gagctcctcc cagggtccag    3180
cgcctgtgct ggaaacagca gccagagccg cccctgcccc tacagcgaga ttcccgtcat    3240
cctgccagcc tccagcatgg aggaggccac ggctgtgca gggttcaatc tcatccactt    3300
ggtggccacg gcatctcct gcttcttggg ctctgggctc ctgaccctag cagtgtacct    3360
gtcttgccag cactgccagc gtcagtccca ggagtccaca ctggtccatc ctgccacccc    3420
caaccatttg cactacaagg gcggaggcac cccgaagaat gaaaagtaca cacccatgga    3480
```

-continued

```
attcaagacc ctgaacaaga ataacttgat ccctgatgac agagccaact tctacccatt      3540
gcagcagacc aatgtgtaca cgactactta ctacccaagc cccctgaaca aacacagctt      3600
ccggcccgag gcctcacctg acaacggtg cttccccaac agctgatacc gccgtcctgg      3660
ggacttgggc ttcttgcctt cataaggcac agagcagatg gagatgggac agtggagcca      3720
gtttggtttt ctccctctgc actaggccaa gaacttgctg ccttgcctgt gggggtccc       3780 atccggcttc agagagctct ggctggcatt gaccatgggg gaaagggctg gtttcaggct      3840
gacatatggc cgcaggtcca gttcagccca ggtctctcat ggttatcttc aacccactg       3900 tcacgctgac actatgctgc catgcctggg ctgtggacct actgggcatt tgaggaattg      3960
gagaatggag atggcaagag ggcaggcttt taagtttggg ttggagacaa cttcctgtgg      4020 ccccacaag ctgagtctgg ccttctccag ctggccccaa aaaggccttt tgct             4074

<210> SEQ ID NO 18
<211> LENGTH: 648
<212> TYPE: DNA
<213> ORGANISM: homo sapiens

<400> SEQUENCE: 18
atgtggggga ggctctggcc cctcctcctc agcatcctca cagcaactgc agtcccagga       60
ccctcactgc ggagaccgtc tagagaacta gatgccaccc ctcggatgac catacccctat      120 gaagagctct ctgggacccg gcacttcaag ggccaagccc agaactactc aacactgctg       180
ctggaggagg cctcagcaag gctgctggtg ggagcccgag gtgccctgtt ctctctcagt       240
gccaacgaca taggagatgg ggctcacaaa gagatccact gggaagcctc cccagagatg       300
caaagcaaat gtcatcaaaa agggaaaaac aaccagacgg agtgctttaa ccatgtgcgg       360
ttcctgcagc ggctcaattc tacccacctc tatgcatgtg ggactcacgc cttccagccc       420
ctctgtgcag ccattgatgc tgaggccttc accttgccaa ccagcttcga ggaggggaag       480
gagaagtgtc cttatgaccc agcccgtggc ttcacaggcc tcatcattga tggaggcctc       540
tacacagcca ctaggtatga attccggagc attcctgaca tccgccggag ccgccaccca       600
cactccctga gaactgagga gacaccaatg cattggctca atggttag                   648

<210> SEQ ID NO 19
<211> LENGTH: 215
<212> TYPE: PRT
<213> ORGANISM: homo sapiens

<400> SEQUENCE: 19

Met Trp Gly Arg Leu Trp Pro Leu Leu Leu Ser Ile Leu Thr Ala Thr
1               5                   10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110
```

```
Thr Glu Cys Phe Asn His Val Arg Phe Leu Gln Arg Leu Asn Ser Thr
        115                 120                 125
His Leu Tyr Ala Cys Gly Thr His Ala Phe Gln Pro Leu Cys Ala Ala
    130                 135                 140
Ile Asp Ala Glu Ala Phe Thr Leu Pro Thr Ser Phe Glu Glu Gly Lys
145                 150                 155                 160
Glu Lys Cys Pro Tyr Asp Pro Ala Arg Gly Phe Thr Gly Leu Ile Ile
                165                 170                 175
Asp Gly Gly Leu Tyr Thr Ala Thr Arg Tyr Glu Phe Arg Ser Ile Pro
            180                 185                 190
Asp Ile Arg Arg Ser Arg His Pro His Ser Leu Arg Thr Glu Glu Thr
        195                 200                 205
Pro Met His Trp Leu Asn Gly
    210                 215
```

<210> SEQ ID NO 20
<211> LENGTH: 1491
<212> TYPE: DNA
<213> ORGANISM: homo sapiens

<400> SEQUENCE: 20

```
atgtggggga ggctctggcc cctcctcctc agcatcctca cagcaactgc agtcccagga      60
ccctcactgc ggagaccgtc tagagaacta gatgccaccc tcggatgaca catacccctat    120
gaagagctct ctgggacccg gcacttcaag ggccaagccc agaactactc aacactgctg     180
ctggaggagg cctcagcaag gctgctggtg ggagcccgag gtgccctgtt ctctctcagt     240
gccaacgaca taggagatgg ggctcacaaa gagatccact gggaagcctc cccagagatg     300
caaagcaaat gtcatcaaaa agggaaaaac aaccagacgg agtgctttaa ccatgtgcgg     360
ttcctgcagc ggctcaattc tacccacctc tatgcatgtg ggactcacgc cttccagccc     420
ctctgtgcag ccattgatgc tgaggccttc accttgccaa ccagcttcga ggaggggaag     480
gagaagtgtc cttatgaccc agcccgtggc ttcacaggcc tcatcattga tggaggcctc     540
tacacagcca ctaggtatga attccggagc attcctgaca tccgccggag ccgccaccca    600
cactccctga aactgaggga cacccaatg cattggctca atgatgcgga gtttgtgttc      660
tccgtcctcg tgcggagag caaggccagt gcagtgggtg atgatgacaa ggtgtactac      720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca   960
gccttcacgc tgagcacaca gtggaagacc ctggaggcct cagccatctg ccgctatgac  1020
ctggcagaga tccaggctgt ctttgcagga ccctatatgg aataccagga tggttcccgg  1080
cgctggggtc gctatgaggg tggggtgcct gagccccggc ctggctcgtg tatcacagat  1140
tcattgcgca gccaaggcta caattcatcc aagacttgc catccctggt cctggacttt   1200
gtaaagttgc acccactgat ggctcggccc gttgtgccca cacgtggacg gccccctgctg  1260
ctcaagcgca acatacgcta cacacacctt acagggacac ctgtcaccac gcctgctgga  1320
cctaccatg acctgctctt tctgggcaca gctgatggct ggatccacaa ggccgtagtc    1380
ctgggctctg ggatgcacat tattgaagag acacaagtgt tcaggagtc ccagtctgtg    1440
gaaaatctag tcatctctct attgcaggta gcccttctct gtgacccta a              1491
```

<210> SEQ ID NO 21
<211> LENGTH: 496
<212> TYPE: PRT
<213> ORGANISM: homo sapiens

<400> SEQUENCE: 21

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

Met Glu Tyr Gln Asp Gly Ser Arg Arg Trp Gly Arg Tyr Glu Gly Gly
        355                 360                 365

Val Pro Glu Pro Arg Pro Gly Ser Cys Ile Thr Asp Ser Leu Arg Ser
    370                 375                 380
```

```
Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
                405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
            435                 440                 445

Gly Thr Ala Asp Gly Trp Ile His Lys Ala Val Val Leu Gly Ser Gly
    450                 455                 460

Met His Ile Ile Glu Glu Thr Gln Val Phe Arg Glu Ser Gln Ser Val
465             470                 475                 480

Glu Asn Leu Val Ile Ser Leu Leu Gln Val Ala Leu Leu Cys Asp Pro
                485                 490                 495

<210> SEQ ID NO 22
<211> LENGTH: 2109
<212> TYPE: DNA
<213> ORGANISM: homo sapiens

<400> SEQUENCE: 22
atgtggggga ggctctggcc cctcctcctc agcatcctca cagcaactgc agtcccagga      60
ccctcactgc ggagaccgtc tagagaacta gatgccaccc ctcggatgac catacccrat     120
gaagagctct ctgggacccg gcacttcaag ggccaagccc agaactactc aacactgctg     180
ctggaggagg cctcagcaag gctgctggtg ggagcccgag gtgccctgtt ctctctcagt     240
gccaacgaca taggagatgg ggctcacaaa gagatccact gggaagcctc cccagagatg     300
caaagcaaat gtcatcaaaa agggaaaaac aaccagacgg agtgctttaa ccatgtgcgg     360
ttcctgcagc ggctcaattc tacccacctc tatgcatgtg ggactcacgc cttccagccc     420
ctctgtgcag ccattgatgc tgaggccttc accttgccaa ccagcttcga ggaggggaag     480
gagaagtgtc cttatgaccc agcccgtggc ttcacaggcc tcatcattga tggaggcctc     540
tacacagcca ctaggtatga attccggagc attcctgaca tccgccggag ccgccaccca     600
cactccctga aactgaggga gacaccaatg cattggctca atgatgcgga gtttgtgttc     660
tccgtcctcg tgcgggagag caaggccagt gcagtgggtg atgatgacaa ggtgtactac     720
ttcttcacgg agcgtgccac tgaggagggc tctggcagct tcactcagag ccgcagcagt     780
caccgtgtgg cccgtgtggc tcgygtctgc aagggagacc tgggagggaa gaagatcctg     840
cagaagaagt ggacttcctt cctgaaagcc cgtctcatct gccacattcc actgtatgag     900
acactgcgtg gggtctgcag cctggatgct gaaacctcaa gccgtacaca cttctatgca     960
gccttcacgc tgagcacaca gtggaagacc ctggaggcct cagccatctg ccgctatgac    1020
ctggcagaga tccaggctgt cttttgcagga ccctatatgg aataccagga tggttcccgg    1080
cgctggggtc gctatgaggg tggggtgcct gagccccggc ctggctcgtg tatcacagat    1140
tcattgcgca gccaaggcta caattcatcc aagacttgc atccctggt cctggacttt     1200 gtaaagttgc acccactgat ggctcggccc gttgtgccca cacgtggacg gccctgctg     1260 ctcaagcgca acatacgcta cacacacctt acagggacac ctgtcaccac gcctgctgga    1320 cctaccctatg acctgctctt tctgggcaca gctgatggct ggatccacaa ggccgtagtc    1380
ctgggctctg gatgcacat tattgaagag acacaagtgt tcaggagtc ccagtctgtg     1440 gaaaatctag tcatctctct attgcagcac agcctctatg tggggctcc tagcggagtc    1500
```

-continued

```
atccagctac cactctccag ctgctcccgc taccgatcct gctatgactg catcttggcc    1560
cgagacccct actgtggctg ggaccctggc acccatgcct gcgcagcagc caccaccata    1620
gccaacaggt cccagggaag caggacagca ctgatacagg acatagagag aggaaatcga    1680
ggctgtgaga gcagcaggga tacaggcagg gctctgcagg tccatatggg ctcaatgtca    1740
ccaccctctg catggccctg tgtgctggat ggtcctgaaa ccagacaagt cctctgccag    1800
ccacctaagc cctgcgtaca ttcacatgca cacatggaag aatgtttatc ggctgggctg    1860
cagtgccccc accctcacct tctcctggtg cattcttgtt tcatccctgc ttctggactt    1920
ggggtaccct cccaattgcc acatcctatc tggtcctctt ccccagcccc atgtggtgac    1980
ctctttgtca agagcttggg aacgggccag cctggggagg taagactgca tcactcccct    2040 cctctcccctt cctgtgtggc ccttgtgaat cagcctcccc actctccttg gtcattctca    2100
agagtatga                                                            2109
```

<210> SEQ ID NO 23
<211> LENGTH: 702
<212> TYPE: PRT
<213> ORGANISM: homo sapiens

<400> SEQUENCE: 23

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
                20                  25                  30

Thr Pro Arg Met Thr Ile Pro Tyr Glu Glu Leu Ser Gly Thr Arg His
            35                  40                  45

Phe Lys Gly Gln Ala Gln Asn Tyr Ser Thr Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255
```

-continued

```
Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
            275                 280                 285

Lys Ala Arg Leu Ile Cys His Ile Pro Leu Tyr Glu Thr Leu Arg Gly
            290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
                340                 345                 350

Met Glu Tyr Gln Asp Gly Ser Arg Arg Trp Gly Arg Tyr Glu Gly Gly
            355                 360                 365

Val Pro Glu Pro Arg Pro Gly Ser Cys Ile Thr Asp Ser Leu Arg Ser
370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
                405                 410                 415

Arg Pro Leu Leu Leu Lys Arg Asn Ile Arg Tyr Thr His Leu Thr Gly
                420                 425                 430

Thr Pro Val Thr Thr Pro Ala Gly Pro Thr Tyr Asp Leu Leu Phe Leu
                435                 440                 445

Gly Thr Ala Asp Gly Trp Ile His Lys Ala Val Val Leu Gly Ser Gly
            450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
            515                 520                 525

Pro Gly Thr His Ala Cys Ala Ala Thr Thr Ile Ala Asn Arg Ser
            530                 535                 540

Gln Gly Ser Arg Thr Ala Leu Ile Gln Asp Ile Glu Arg Gly Asn Arg
545                 550                 555                 560

Gly Cys Glu Ser Ser Arg Asp Thr Gly Arg Ala Leu Gln Val His Met
                565                 570                 575

Gly Ser Met Ser Pro Pro Ser Ala Trp Pro Cys Val Leu Asp Gly Pro
            580                 585                 590

Glu Thr Arg Gln Val Leu Cys Gln Pro Pro Lys Pro Cys Val His Ser
            595                 600                 605

His Ala His Met Glu Glu Cys Leu Ser Ala Gly Leu Gln Cys Pro His
            610                 615                 620

Pro His Leu Leu Leu Val His Ser Cys Phe Ile Pro Ala Ser Gly Leu
625                 630                 635                 640

Gly Val Pro Ser Gln Leu Pro His Pro Ile Trp Ser Ser Pro Ala
                645                 650                 655

Pro Cys Gly Asp Leu Phe Val Lys Ser Leu Gly Thr Gly Gln Pro Gly
            660                 665                 670
```

```
Glu Val Arg Leu His His Ser Pro Pro Leu Pro Ser Cys Val Ala Leu
        675                 680                 685

Val Asn Gln Pro Pro His Ser Pro Trp Ser Phe Ser Arg Val
        690                 695                 700

<210> SEQ ID NO 24
<211> LENGTH: 2094
<212> TYPE: DNA
<213> ORGANISM: homo sapiens

<400> SEQUENCE: 24
atgtggggga ggctctggcc cctcctcctc agcatcctca cagcaactgc agtcccagga      60
ccctcactgc ggagaccgtc tagagaacta gatgccaccc ctcggatgac atacccctat    120
gaagagctct ctgggacccg cacttcaag  ggccaagccc agaactactc aacactgctg    180
ctggaggagg cctcagcaag gctgctggtg ggagcccgag gtgccctgtt ctctctcagt    240
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccacctc tatgcatgtg ggactcacgc cttccagccc    420
ctctgtgcag ccattgatgc tgaggccttc accttgccaa ccagcttcga ggaggggaag    480
gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga aactgaggga cacccaatg cattggctca atgatgcgga gtttgtgttc    660
tccgtcctcg tgcgggagag caaggccagt gcagtgggtg atgatgacaa ggtgtactac    720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac   1020
ctggcagaga tccaggctgt ctttgcagga ccctatatgg aataccagga tggttcccgg   1080
cgctggggtc gctatgaggg tggggtgcct gagccccggc ctggctcgtg tatcacagat   1140
tcattgcgca gccaaggcta caattcatcc aagacttgc atccctggt cctggacttt   1200 gtaaagttgc acccactgat ggctcggccc gttgtgccca cacgtggacg gcccctgctg   1260
ctcaagcgca acatacgcta cacacacctt acagggacac ctgtcaccac gcctgctgga   1320
cctacctatg acctgctctt tctgggcaca gctgatggct ggatccacaa ggccgtagtc   1380
ctgggctctg ggatgcacat tattgaagag acacaagtgt tcaggagtc ccagtctgtg   1440 gaaaatctag tcatctctct attgcagcac agcctctatg tggggctcc tagcggagtc   1500 atccagctac cactctccag ctgctcccgc taccgatcct gctatgactg catcttggcc   1560
cgagacccct actgtggctg ggaccctggc acccatgcct gcgcagcagc caccaccata   1620
gccaacagga cagcactgat acaggacata gagagaggaa atcgaggctg tgagagcagc   1680
agggatacag gcagggctct gcaggtccat atgggctcaa tgtcaccacc ctctgcatgg   1740
ccctgtgtgc tggatggtcc tgaaaccaga caagtcctct gccagccacc taagccctgc   1800
gtacattcac atgcacacat ggaagaatgt ttatcggctg ggctgcagtg ccccacccct   1860
caccttctcc tggtgcattc ttgtttcatc cctgcttctg gacttgggt accctcccaa   1920 ttgccacatc ctatctggtc ctcttcccca gccccatgtg gtgacctctt tgtcaagagc   1980
```

-continued ttgggaacgg gccagcctgg ggaggtaaga ctgcatcact cccctcctct cccttcctgt 2040
gtggcccttg tgaatcagcc tccccactct ccttggtcat tctcaagagt atga 2094

<210> SEQ ID NO 25
<211> LENGTH: 697
<212> TYPE: PRT
<213> ORGANISM: homo sapiens

<400> SEQUENCE: 25

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350
```

```
Met Glu Tyr Gln Asp Gly Ser Arg Arg Trp Gly Arg Tyr Glu Gly Gly
            355                 360                 365

Val Pro Glu Pro Arg Pro Gly Ser Cys Ile Thr Asp Ser Leu Arg Ser
        370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
            405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
        435                 440                 445

Gly Thr Ala Asp Gly Trp Ile His Lys Ala Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
        515                 520                 525

Pro Gly Thr His Ala Cys Ala Ala Thr Thr Ile Ala Asn Arg Thr
    530                 535                 540

Ala Leu Ile Gln Asp Ile Glu Arg Gly Asn Arg Gly Cys Glu Ser Ser
545                 550                 555                 560

Arg Asp Thr Gly Arg Ala Leu Gln Val His Met Gly Ser Met Ser Pro
                565                 570                 575

Pro Ser Ala Trp Pro Cys Val Leu Asp Gly Pro Glu Thr Arg Gln Val
            580                 585                 590

Leu Cys Gln Pro Pro Lys Pro Cys Val His Ser His Ala His Met Glu
        595                 600                 605

Glu Cys Leu Ser Ala Gly Leu Gln Cys Pro His Pro His Leu Leu Leu
    610                 615                 620

Val His Ser Cys Phe Ile Pro Ala Ser Gly Leu Gly Val Pro Ser Gln
625                 630                 635                 640

Leu Pro His Pro Ile Trp Ser Ser Pro Ala Pro Cys Gly Asp Leu
                645                 650                 655

Phe Val Lys Ser Leu Gly Thr Gly Gln Pro Gly Glu Val Arg Leu His
            660                 665                 670

His Ser Pro Pro Leu Pro Ser Cys Val Ala Leu Val Asn Gln Pro Pro
        675                 680                 685

His Ser Pro Trp Ser Phe Ser Arg Val
    690                 695

<210> SEQ ID NO 26
<211> LENGTH: 2532
<212> TYPE: DNA
<213> ORGANISM: homo sapiens

<400> SEQUENCE: 26
atgtggggga ggctctggcc cctcctcctc agcatcctca cagcaactgc agtcccagga      60
ccctcactgc ggagaccgtc tagagaacta gatgccaccc ctcggatgac catacccta    120 gaagagctct ctgggacccg gcacttcaag ggccaagccc agaactactc aacactgctg     180
```

-continued

```
ctggaggagg cctcagcaag gctgctggtg ggagcccgag gtgccctgtt ctctctcagt    240
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccacctc tatgcatgtg ggactcacgc cttccagccc    420
ctctgtgcag ccattgatgc tgaggccttc accttgccaa ccagcttcga ggagggaag    480
gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga gaactgagga gacaccaatg cattggctca atgatgcgga gtttgtgttc    660
tccgtcctcg tgcgggagag caaggccagt gcagtgggtg atgatgacaa ggtgtactac    720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac   1020
ctggcagaga tccaggctgt cttttgcagga ccctatatgg aataccagga tggttcccgg   1080
cgctggggtc gctatgaggg tggggtgcct gagccccggc ctggctcgtg tatcacagat   1140
tcattgcgca gccaaggcta caattcatcc caagacttgc catccctggt cctggacttt   1200
gtaaagttgc acccactgat ggctcggccc gttgtgccca cacgtggacg gccctgctg    1260
ctcaagcgca acatacgcta cacacacctt acagggacac ctgtcaccac gcctgctgga   1320
cctacctatg acctgctctt tctgggcaca gctgatggct ggatccacaa ggccgtagtc   1380
ctgggctctg ggatgcacat tattgaagag acacaagtgt tcagggagtc ccagtctgtg   1440
gaaaatctag tcatctctct attgcagcac agcctctatg tgggggctcc tagcggagtc   1500
atccagctac cactctccag ctgctcccgc taccgatcct gctatgactg catcttggcc   1560
cgagacccct actgtggctg ggaccctggc acccatgcct cgcgcagcag caccaccata   1620
gccaacaggt cccagggaag caggacagca ctgatacagg acatagagag aggaaatcga   1680
ggctgtgaga gcagcaggga tacagggcca ccaccaccac tgaagacccg ctctgtgctc   1740
cggggtgatg atgtcctcct gccctgtgac cagccatcca acctggcccg ggccttgtgg   1800
ctactcaatg ggagcatggg cctgagcgat gggcagggtg gctaccgtgt gggcgtggac   1860
gggctgctgg ttacagatgc acagcctgag cacagtggca actatggctg ctatgccgag   1920
gaaaatggcc tccgcaccct gctggcctcc tatagtctca cagtccggcc agccactcct   1980
gccccagctc caaaagcccc tgccacacct ggggcacagc tggcacctga tgtgagactg   2040
ctctatgtgc tagccattgc cgcgcttggt ggccyctgcc tcatcctggc ctcctccctc   2100
ctctatgtgg cctgtctgcg ggaaggcaga cgagggcgcc gacggaaata ctcactgggt   2160
cgggccagcc gggcaggagg atctgcggtg caactgcaga cagtctcagg ccagtgtcct   2220
ggagaggaag atgagggtga tgatgagggg gctggggcc tggagggcag ctgtctccag   2280
atcatccctg ggagggagc cccagcccca ccacccccac cgcccccacc gccaccggct   2340
gagctgacca atggcttggt ggcactgccc agccggctgc ggaggatgaa tggcaatagc   2400
tatgtgcttc tgaggcagag caacaatgga gtaccagcag ggccctgctc cttcgccgag   2460
gaactcagcc gcatcctgga aaaaggaag cacacgcagc tcgtggagca gctagatgag   2520
agctctgtct ga                                                       2532
```

<210> SEQ ID NO 27
<211> LENGTH: 843
<212> TYPE: PRT
<213> ORGANISM: homo sapiens

<400> SEQUENCE: 27

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

Met Glu Tyr Gln Asp Gly Ser Arg Arg Trp Gly Arg Tyr Glu Gly Gly
        355                 360                 365

Val Pro Glu Pro Arg Pro Gly Ser Cys Ile Thr Asp Ser Leu Arg Ser
    370                 375                 380
```

```
Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
            405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
            435                 440                 445

Gly Thr Ala Asp Gly Trp Ile His Lys Ala Val Val Leu Gly Ser Gly
450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
            485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
            515                 520                 525

Pro Gly Thr His Ala Cys Ala Ala Ala Thr Thr Ile Ala Asn Arg Ser
530                 535                 540

Gln Gly Ser Arg Thr Ala Leu Ile Gln Asp Ile Glu Arg Gly Asn Arg
545                 550                 555                 560

Gly Cys Glu Ser Ser Arg Asp Thr Gly Pro Pro Pro Leu Lys Thr
            565                 570                 575

Arg Ser Val Leu Arg Gly Asp Val Leu Leu Pro Cys Asp Gln Pro
            580                 585                 590

Ser Asn Leu Ala Arg Ala Leu Trp Leu Leu Asn Gly Ser Met Gly Leu
            595                 600                 605

Ser Asp Gly Gln Gly Gly Tyr Arg Val Gly Val Asp Gly Leu Leu Val
            610                 615                 620

Thr Asp Ala Gln Pro Glu His Ser Gly Asn Tyr Gly Cys Tyr Ala Glu
625                 630                 635                 640

Glu Asn Gly Leu Arg Thr Leu Leu Ala Ser Tyr Ser Leu Thr Val Arg
            645                 650                 655

Pro Ala Thr Pro Ala Pro Ala Pro Lys Ala Pro Ala Thr Pro Gly Ala
            660                 665                 670

Gln Leu Ala Pro Asp Val Arg Leu Leu Tyr Val Leu Ala Ile Ala Ala
            675                 680                 685

Leu Gly Gly Leu Cys Leu Ile Leu Ala Ser Ser Leu Leu Tyr Val Ala
690                 695                 700

Cys Leu Arg Glu Gly Arg Gly Arg Arg Lys Tyr Ser Leu Gly
705                 710                 715                 720

Arg Ala Ser Arg Ala Gly Gly Ser Ala Val Gln Leu Gln Thr Val Ser
            725                 730                 735

Gly Gln Cys Pro Gly Glu Glu Asp Glu Gly Asp Asp Glu Gly Ala Gly
            740                 745                 750

Gly Leu Glu Gly Ser Cys Leu Gln Ile Ile Pro Gly Glu Gly Ala Pro
            755                 760                 765

Ala Pro Pro Pro Pro Pro Pro Pro Pro Ala Glu Leu Thr Asn
            770                 775                 780

Gly Leu Val Ala Leu Pro Ser Arg Leu Arg Arg Met Asn Gly Asn Ser
785                 790                 795                 800
```

| Tyr | Val | Leu | Leu | Arg | Gln | Ser | Asn | Asn | Gly | Val | Pro | Ala | Gly | Pro | Cys |
|---|---|---|---|---|---|---|---|---|---|---|---|---|---|---|---|
| | | | | 805 | | | | | 810 | | | | | 815 | |

| Ser | Phe | Ala | Glu | Glu | Leu | Ser | Arg | Ile | Leu | Glu | Lys | Arg | Lys | His | Thr |
|---|---|---|---|---|---|---|---|---|---|---|---|---|---|---|---|
| | | | 820 | | | | | 825 | | | | | 830 | | |

| Gln | Leu | Val | Glu | Gln | Leu | Asp | Glu | Ser | Ser | Val |
|---|---|---|---|---|---|---|---|---|---|---|
| | | | 835 | | | | 840 | | | |

<210> SEQ ID NO 28
<211> LENGTH: 2517
<212> TYPE: DNA
<213> ORGANISM: homo sapiens

<400> SEQUENCE: 28

| | | | | | |
|---|---|---|---|---|---|
| atgtggggga | ggctctggcc | cctcctcctc | agcatcctca | cagcaactgc | agtcccagga | 60 |
| ccctcactgc | ggagaccgtc | tagagaacta | gatgccaccc | ctcggatgac | catacccctat | 120 |
| gaagagctct | ctgggacccg | gcacttcaag | ggccaagccc | agaactactc | aacactgctg | 180 |
| ctggaggagg | cctcagcaag | gctgctggtg | ggagcccgag | gtgccctgtt | ctctctcagt | 240 |
| gccaacgaca | taggagatgg | ggctcacaaa | gagatccact | gggaagcctc | cccagagatg | 300 |
| caaagcaaat | gtcatcaaaa | agggaaaaac | aaccagacgg | agtgctttaa | ccatgtgcgg | 360 |
| ttcctgcagc | ggctcaattc | tacccaccctc | tatgcatgtg | ggactcacgc | cttccagccc | 420 |
| ctctgtgcag | ccattgatgc | tgaggccttc | accttgccaa | ccagcttcga | ggaggggaag | 480 |
| gagaagtgtc | cttatgaccc | agcccgtggc | ttcacaggcc | tcatcattga | tggaggcctc | 540 |
| tacacagcca | ctaggtatga | attccggagc | attcctgaca | tccgccggag | ccgccaccca | 600 |
| cactccctga | aactgagga | gacaccaatg | cattggctca | atgatgcgga | gtttgtgttc | 660 |
| tccgtcctcg | tgcgggagag | caaggccagt | gcagtgggtg | atgatgacaa | ggtgtactac | 720 |
| ttcttcacgg | agcgtgccac | tgaggagggc | tctggcagct | tcactcagag | ccgcagcagt | 780 |
| caccgtgtgg | cccgtgtggc | tcgygtctgc | aagggagacc | tgggagggaa | gaagatcctg | 840 |
| cagaagaagt | ggacttcctt | cctgaaagcc | cgtctcatct | gccacattcc | actgtatgag | 900 |
| acactgcgtg | gggtctgcag | cctggatgct | gaaacctcaa | gccgtacaca | cttctatgca | 960 |
| gccttcacgc | tgagcacaca | gtggaagacc | ctggaggcct | cagccatctg | ccgctatgac | 1020 |
| ctggcagaga | tccaggctgt | ctttgcagga | ccctatatgg | aataccagga | tggttcccgg | 1080 |
| cgctggggtc | gctatgaggg | tggggtgcct | gagccccggc | ctggctcgtg | tatcacagat | 1140 |
| tcattgcgca | gccaaggcta | caattcatcc | caagacttgc | catccctggt | cctggacttt | 1200 |
| gtaaagttgc | acccactgat | ggctcggccc | gttgtgccca | cacgtggacg | gcccctgctg | 1260 |
| ctcaagcgca | acatacgcta | cacacacctt | acagggacac | ctgtcaccac | gcctgctgga | 1320 |
| cctacctatg | acctgctctt | tctgggcaca | gctgatggct | ggatccacaa | ggccgtagtc | 1380 |
| ctgggctctg | ggatgcacat | tattgaagag | acacaagtgt | tcaggagtc | ccagtctgtg | 1440 |
| gaaaatctag | tcatctctct | attgcagcac | agcctctatg | tggggctcc | tagcggagtc | 1500 |
| atccagctac | cactctccag | ctgctcccgc | taccgatcct | gctatgactg | catcttggcc | 1560 |
| cgagacccct | actgtggctg | ggaccctggc | acccatgcct | cgcagcagc | caccaccata | 1620 |
| gccaacagga | cagcactgat | acaggacata | gagagaggaa | atcgaggctg | tgagagcagc | 1680 |
| agggatacag | ggccaccacc | accactgaag | acccgctctg | tgctccgggg | tgatgatgtc | 1740 |
| ctcctgccct | gtgaccagcc | atccaacctg | gcccgggcct | tgtggctact | caatgggagc | 1800 |
| atgggcctga | gcgatgggca | gggtggctac | cgtgtgggcg | tggacgggct | gctggttaca | 1860 |

```
gatgcacagc tgagcacag tggcaactat ggctgctatg ccgaggaaaa tggcctccgc    1920
accctgctgg cctcctatag tctcacagtc cggccagccc ctcctgcccc agctccaaaa    1980
gcccctgcca cacctggggc acagctggca cctgatgtga gactgctcta tgtgctagcc    2040
attgccgcgc ttggtggccy ctgcctcatc ctggcctcct ccctcctcta tgtggcctgt    2100
ctgcgggaag cagacgagg cgccgacgg aaatactcac tgggtcgggc cagccgggca    2160
ggaggatctg cggtgcaact gcagacagtc tcaggccagt gtcctggaga ggaagatgag    2220
ggtgatgatg aggggctggg gggcctggag ggcagctgtc tccagatcat ccctggggag    2280
ggagccccag ccccaccacc cccaccgccc ccaccgccac cggctgagct gaccaatggc    2340
ttggtggcac tgcccagccg gctgcggagg atgaatggca atagctatgt gcttctgagg    2400
cagagcaaca atggagtacc agcagggccc tgctccttcg ccgaggaact cagccgcatc    2460
ctggaaaaaa ggaagcacac gcagctcgtg gagcagctag atgagagctc tgtctga      2517
```

<210> SEQ ID NO 29
<211> LENGTH: 838
<212> TYPE: PRT
<213> ORGANISM: homo sapiens

<400> SEQUENCE: 29

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255
```

-continued

```
Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

Met Glu Tyr Gln Asp Gly Ser Arg Arg Trp Gly Arg Tyr Glu Gly Gly
        355                 360                 365

Val Pro Glu Pro Arg Pro Gly Ser Cys Ile Thr Asp Ser Leu Arg Ser
    370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
                405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
        435                 440                 445

Gly Thr Ala Asp Gly Trp Ile His Lys Ala Val Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
        515                 520                 525

Pro Gly Thr His Ala Cys Ala Ala Thr Thr Ile Ala Asn Arg Thr
    530                 535                 540

Ala Leu Ile Gln Asp Ile Glu Arg Gly Asn Arg Gly Cys Glu Ser Ser
545                 550                 555                 560

Arg Asp Thr Gly Pro Pro Pro Leu Lys Thr Arg Ser Val Leu Arg
                565                 570                 575

Gly Asp Asp Val Leu Leu Pro Cys Asp Gln Pro Ser Asn Leu Ala Arg
            580                 585                 590

Ala Leu Trp Leu Leu Asn Gly Ser Met Gly Leu Ser Asp Gly Gln Gly
        595                 600                 605

Gly Tyr Arg Val Gly Val Asp Gly Leu Leu Val Thr Asp Ala Gln Pro
    610                 615                 620

Glu His Ser Gly Asn Tyr Gly Cys Tyr Ala Glu Glu Asn Gly Leu Arg
625                 630                 635                 640

Thr Leu Leu Ala Ser Tyr Ser Leu Thr Val Arg Pro Ala Thr Pro Ala
                645                 650                 655

Pro Ala Pro Lys Ala Pro Ala Thr Pro Gly Ala Gln Leu Ala Pro Asp
            660                 665                 670
```

-continued

```
Val Arg Leu Leu Tyr Val Leu Ala Ile Ala Ala Leu Gly Gly Leu Cys
        675                 680                 685
Leu Ile Leu Ala Ser Ser Leu Leu Tyr Val Ala Cys Leu Arg Glu Gly
    690                 695                 700
Arg Arg Gly Arg Arg Lys Tyr Ser Leu Gly Arg Ala Ser Arg Ala
705                 710                 715                 720
Gly Gly Ser Ala Val Gln Leu Gln Thr Val Ser Gly Gln Cys Pro Gly
                725                 730                 735
Glu Glu Asp Glu Gly Asp Asp Glu Gly Ala Gly Leu Glu Gly Ser
            740                 745                 750
Cys Leu Gln Ile Ile Pro Gly Glu Gly Ala Pro Ala Pro Pro Pro
        755                 760                 765
Pro Pro Pro Pro Pro Ala Glu Leu Thr Asn Gly Leu Val Ala Leu
    770                 775                 780
Pro Ser Arg Leu Arg Arg Met Asn Gly Asn Ser Tyr Val Leu Leu Arg
785                 790                 795                 800
Gln Ser Asn Asn Gly Val Pro Ala Gly Pro Cys Ser Phe Ala Glu Glu
                805                 810                 815
Leu Ser Arg Ile Leu Glu Lys Arg Lys His Thr Gln Leu Val Glu Gln
            820                 825                 830
Leu Asp Glu Ser Ser Val
        835
```

<210> SEQ ID NO 30
<211> LENGTH: 2613
<212> TYPE: DNA
<213> ORGANISM: homo sapiens

<400> SEQUENCE: 30

```
atgtggggga ggctctggcc cctcctcctc agcatcctca cagcaactgc agtcccagga      60
ccctcactgc ggagaccgtc tagagaacta gatgccaccc tcggatgaca catacccctat   120
gaagagctct ctgggacccg gcacttcaag ggccaagccc agaactactc aacactgctg    180
ctggaggagg cctcagcaag gctgctggtg ggagcccgag gtgccctgtt ctctctcagt    240
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccacctc tatgcatgtg ggactcacgc cttccagccc    420
ctctgtgcag ccattgatgc tgaggccttc accttgccaa ccagcttcga ggaggggaag    480
gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga aactgaggga gacaccaatg cattggctca tgatgcggga gtttgtgttc    660
tccgtcctcg tgcgggagag caaggccagt gcagtgggtg atgatgacaa ggtgtactac    720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac   1020
ctggcagaga tccaggctgt cttttgcagga ccctatatgg aataccagga tggttcccgg   1080
cgctggggtc gctatgaggg tgggggtgcct gagccccggc ctggctcgtg tatcacagat   1140
```

```
tcattgcgca gccaaggcta caattcatcc caagacttgc catccctggt cctggacttt    1200
gtaaagttgc acccactgat ggctcggccc gttgtgccca cacgtggacg gcccctgctg    1260
ctcaagcgca acatacgcta cacacacctt acagggacac ctgtcaccac gcctgctgga    1320
cctacctatg acctgctctt tctgggcaca gctgatggct ggatccacaa ggccgtagtc    1380
ctgggctctg ggatgcacat tattgaagag acacaagtgt tcagggagtc ccagtctgtg    1440
gaaaatctag tcatctctct attgcagcac agcctctatg tgggggctcc tagcggagtc    1500
atccagctac cactctccag ctgctcccgc taccgatcct gctatgactg catcttggcc    1560
cgagacccct actgtggctg ggaccctggc acccatgcct cgcagcagc caccaccata    1620
gccaacaggt cccagggaag caggacagca ctgatacagg acatagagag aggaaatcga    1680
ggctgtgaga gcagcaggga tacagggcca ccaccaccac tgaagacccg ctctgtgctc    1740
cggggtgatg atgtcctcct gccctgtgac cagccatcca acctggcccg ggccttgtgg    1800
ctactcaatg ggagcatggg cctgagcgat gggcagggtg gctaccgtgt gggcgtggac    1860
gggctgctgg ttacagatgc acagcctgag cacagtggca actatggctg ctatgccgag    1920
gaaaatggcc tccgcaccct gctggcctcc tatagtctca cagtccggcc agccactcct    1980
gccccagctc aaaagcccc tgccacacct ggggcacagc tggcacctga tgtgagactg    2040
ctctatgtgc tagccattgc cgcgcttggt ggccyctgcc tcatcctggc ctcctccctc    2100
ctctatgtgg cctgtctgcg ggaaggcaga cgagggcgcc gacggaaata ctcactgggt    2160
cgggccagcc gggcaggagg atctgcggtg caactgcaga cagtctcagg cagggctctg    2220
caggtccata tgggctcaat gtcaccaccc tctgcatggc cctgtgtgct ggatggtcct    2280
gaaaccagac aagtcctctg ccagccacct aagccctgcg tacattcaca tgcacacatg    2340
gaagaatgtt tatcggctgg gctgcagtgc ccccacccctc accttctcct ggtgcattct    2400
tgtttcatcc ctgcttctgg acttggggta ccctcccaat tgccacatcc tatctggtcc    2460
tcttccccag ccccatgtgg tgacctcttt gtcaagagct tgggaacggg ccagcctggg    2520
gaggtaagac tgcatcactc ccctcctctc ccttcctgtg tggcccttgt gaatcagcct    2580
ccccactctc cttggtcatt ctcaagagta tga                                 2613

<210> SEQ ID NO 31
<211> LENGTH: 870
<212> TYPE: PRT
<213> ORGANISM: homo sapiens

<400> SEQUENCE: 31
```

Met Trp Gly Arg Leu Trp Pro Leu Leu Leu Ser Ile Leu Thr Ala Thr
1               5                   10                  15

Ala Val Pro Gly Pro Ser Leu Arg Arg Pro Ser Arg Glu Leu Asp Ala
                20                  25                  30

Thr Pro Arg Met Thr Ile Pro Tyr Glu Glu Leu Ser Gly Thr Arg His
            35                  40                  45

Phe Lys Gly Gln Ala Gln Asn Tyr Ser Thr Leu Leu Leu Glu Glu Ala
        50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
                100                 105                 110

```
Thr Glu Cys Phe Asn His Val Arg Phe Leu Gln Arg Leu Asn Ser Thr
    115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
                180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser His Arg Val Ala Arg Val Ala Arg Val Cys Lys Gly
                260                 265                 270

Asp Leu Gly Gly Lys Lys Ile Leu Gln Lys Lys Trp Thr Ser Phe Leu
    275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
                340                 345                 350

Met Glu Tyr Gln Asp Gly Ser Arg Arg Trp Gly Arg Tyr Glu Gly Gly
        355                 360                 365

Val Pro Glu Pro Arg Pro Gly Ser Cys Ile Thr Asp Ser Leu Arg Ser
    370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
                405                 410                 415

Arg Pro Leu Leu Leu Lys Arg Asn Ile Arg Tyr Thr His Leu Thr Gly
                420                 425                 430

Thr Pro Val Thr Thr Pro Ala Gly Pro Thr Tyr Asp Leu Leu Phe Leu
        435                 440                 445

Gly Thr Ala Asp Gly Trp Ile His Lys Ala Val Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
                500                 505                 510

Ser Cys Tyr Asp Cys Ile Leu Ala Arg Asp Pro Tyr Cys Gly Trp Asp
        515                 520                 525
```

```
Pro Gly Thr His Ala Cys Ala Ala Thr Thr Ile Ala Asn Arg Ser
    530             535             540
Gln Gly Ser Arg Thr Ala Leu Ile Gln Asp Ile Glu Arg Gly Asn Arg
545                 550                 555                 560
Gly Cys Glu Ser Ser Arg Asp Thr Gly Pro Pro Pro Leu Lys Thr
                565             570             575
Arg Ser Val Leu Arg Gly Asp Val Leu Pro Cys Asp Gln Pro
            580             585             590
Ser Asn Leu Ala Arg Ala Leu Trp Leu Leu Asn Gly Ser Met Gly Leu
            595             600             605
Ser Asp Gly Gln Gly Gly Tyr Arg Val Gly Val Asp Gly Leu Leu Val
    610             615             620
Thr Asp Ala Gln Pro Glu His Ser Gly Asn Tyr Gly Cys Tyr Ala Glu
625             630             635             640
Glu Asn Gly Leu Arg Thr Leu Leu Ala Ser Tyr Ser Leu Thr Val Arg
                645             650             655
Pro Ala Thr Pro Ala Pro Ala Pro Lys Ala Pro Ala Thr Pro Gly Ala
                660             665             670
Gln Leu Ala Pro Asp Val Arg Leu Leu Tyr Val Leu Ala Ile Ala Ala
            675             680             685
Leu Gly Gly Leu Cys Leu Ile Leu Ala Ser Ser Leu Leu Tyr Val Ala
    690             695             700
Cys Leu Arg Glu Gly Arg Arg Gly Arg Arg Arg Lys Tyr Ser Leu Gly
705             710             715             720
Arg Ala Ser Arg Ala Gly Gly Ser Ala Val Gln Leu Gln Thr Val Ser
                725             730             735
Gly Arg Ala Leu Gln Val His Met Gly Ser Met Ser Pro Pro Ser Ala
            740             745             750
Trp Pro Cys Val Leu Asp Gly Pro Glu Thr Arg Gln Val Leu Cys Gln
    755             760             765
Pro Pro Lys Pro Cys Val His Ser His Ala His Met Glu Glu Cys Leu
770             775             780
Ser Ala Gly Leu Gln Cys Pro His Pro His Leu Leu Val His Ser
785             790             795             800
Cys Phe Ile Pro Ala Ser Gly Leu Gly Val Pro Ser Gln Leu Pro His
                805             810             815
Pro Ile Trp Ser Ser Pro Ala Pro Cys Gly Asp Leu Phe Val Lys
            820             825             830
Ser Leu Gly Thr Gly Gln Pro Gly Glu Val Arg Leu His His Ser Pro
    835             840             845
Pro Leu Pro Ser Cys Val Ala Leu Val Asn Gln Pro Pro His Ser Pro
850             855             860
Trp Ser Phe Ser Arg Val
865             870
```

<210> SEQ ID NO 32
<211> LENGTH: 2598
<212> TYPE: DNA
<213> ORGANISM: homo sapiens

<400> SEQUENCE: 32
atgtggggga ggctctggcc cctcctcctc agcatcctca cagcaactgc agtcccagga    60
ccctcactgc ggagaccgtc tagagaacta gatgccaccc tcggatgac catacccctat  120 gaagagctct ctgggaccog gcacttcaag ggccaagccc agaactactc aacactgctg    180

```
ctggaggagg cctcagcaag gctgctggtg ggagcccgag gtgccctgtt ctctctcagt    240
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccacctc tatgcatgtg ggactcacgc cttccagccc    420
ctctgtgcag ccattgatgc tgaggccttc accttgccaa ccagcttcga ggagggaag    480 gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga gaactgagga gacaccaatg cattggctca atgatgcgga gtttgtgttc    660
tccgtcctcg tgcgggagag caaggccagt gcagtgggtg atgatgacaa ggtgtactac    720
ttcttcacga gcgtgccac tgaggagggc tctggcagct tcactcagag ccgcagcagt    780
caccgtgtgg cccgtgtggc tcgygtctgc aagggagacc tgggagggaa aagatcctg    840 cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac    1020
ctggcagaga tccaggctgt cttttgcagga ccctatatgg aataccagga tggttcccgg    1080
cgctggggtc gctatgaggg tggggtgcct gagccccggc ctggctcgtg tatcacagat    1140
tcattgcgca gccaaggcta caattcatcc caagacttgc catccctggt cctggacttt    1200
gtaaagttgc acccactgat ggctcggccc gttgtgccca cacgtggacg gccccctgctg    1260 ctcaagcgca acatacgcta cacacacctt acagggacac ctgtcaccac gcctgctgga    1320
cctacctatg acctgctctt tctgggcaca gctgatggct ggatccacaa ggccgtagtc    1380
ctgggctctg ggatgcacat tattgaagag acacaagtgt tcagggagtc ccagtctgtg    1440
gaaaatctag tcatctctct attgcagcac agcctctatg tggggctcc tagcggagtc    1500 atccagctac cactctccag ctgctcccgc taccgatcct gctatgactg catcttggcc    1560
cgagacccct actgtggctg ggaccctggc acccatgcct gcgcagcagc caccaccata    1620
gccaacagga cagcactgat acaggacata gagagaggaa atcgaggctg tgagagcagc    1680
agggatacag ggccaccacc accactgaag acccgctctg tgctccgggg tgatgatgtc    1740
ctcctgccct gtgaccagcc atccaacctg gcccgggcct gtggctact caatgggagc    1800 atgggcctga gcgatgggca gggtggctac cgtgtgggcg tggacgggct gctggttaca    1860
gatgcacagc ctgagcacag tggcaactat ggctgctatg ccgaggaaaa tggcctccgc    1920
accctgctgg cctcctatag tctcacagtc cggccagcca ctcctgcccc agctccaaaa    1980
gcccctgcca cacctggggc acagctggca cctgatgtga gactgctcta tgtgctagcc    2040
attgccgcgc ttggtggccy ctgcctcatc ctggcctcct ccctcctcta tgtggcctgt    2100
ctgcgggaag gcagacgagg gcgccgacgg aaatactcac tgggtcggc cagccgggca    2160 ggaggatctg cggtgcaact gcagacagtc tcaggcaggg ctctgcaggt ccatatgggc    2220
tcaatgtcac caccctctgc atggccctgt gtgctggatg gtcctgaaac cagacaagtc    2280
ctctgccagc cacctaagcc ctgcgtacat tcacatgcac acatggaaga atgtttatcg    2340
gctgggctga agtgcccca ccctcacctt ctcctggtgc attcttgttt catccctgct    2400 tctgacttg gggtacccctc ccaattgcca catcctatct ggtcctcttc cccagcccca    2460
tgtggtgacc tctttgtcaa gagcttggga acgggccagc ctggggaggt aagactgcat    2520
```
cactcccctc ctctcccttc ctgtgtggcc cttgtgaatc agcctcccca ctctccttgg    2580
tcattctcaa gagtatga                                                   2598

<210> SEQ ID NO 33
<211> LENGTH: 865
<212> TYPE: PRT
<213> ORGANISM: homo sapiens

<400> SEQUENCE: 33

Met Trp Gly Arg Leu Trp Pro Leu Leu Ser Ile Leu Thr Ala Thr
 1               5                  10                  15

Ala Val Pro Gly Pro Ser Leu Arg Arg Pro Ser Arg Glu Leu Asp Ala
                20                  25                  30

Thr Pro Arg Met Thr Ile Pro Tyr Glu Glu Leu Ser Gly Thr Arg His
            35                  40                  45

Phe Lys Gly Gln Ala Gln Asn Tyr Ser Thr Leu Leu Leu Glu Glu Ala
        50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
               100                 105                 110

Thr Glu Cys Phe Asn His Val Arg Phe Leu Gln Arg Leu Asn Ser Thr
            115                 120                 125

His Leu Tyr Ala Cys Gly Thr His Ala Phe Gln Pro Leu Cys Ala Ala
       130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

```
Met Glu Tyr Gln Asp Gly Ser Arg Arg Trp Gly Arg Tyr Glu Gly Gly
        355                 360                 365

Val Pro Glu Pro Arg Pro Gly Ser Cys Ile Thr Asp Ser Leu Arg Ser
    370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
                405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
        435                 440                 445

Gly Thr Ala Asp Gly Trp Ile His Lys Ala Val Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
        515                 520                 525

Pro Gly Thr His Ala Cys Ala Ala Thr Thr Ile Ala Asn Arg Thr
    530                 535                 540

Ala Leu Ile Gln Asp Ile Glu Arg Gly Asn Arg Gly Cys Glu Ser Ser
545                 550                 555                 560

Arg Asp Thr Gly Pro Pro Pro Leu Lys Thr Arg Ser Val Leu Arg
                565                 570                 575

Gly Asp Asp Val Leu Leu Pro Cys Asp Gln Pro Ser Asn Leu Ala Arg
            580                 585                 590

Ala Leu Trp Leu Leu Asn Gly Ser Met Gly Leu Ser Asp Gly Gln Gly
        595                 600                 605

Gly Tyr Arg Val Gly Val Asp Gly Leu Leu Val Thr Asp Ala Gln Pro
    610                 615                 620

Glu His Ser Gly Asn Tyr Gly Cys Tyr Ala Glu Glu Asn Gly Leu Arg
625                 630                 635                 640

Thr Leu Leu Ala Ser Tyr Ser Leu Thr Val Arg Pro Ala Thr Pro Ala
                645                 650                 655

Pro Ala Pro Lys Ala Pro Ala Thr Pro Gly Ala Gln Leu Ala Pro Asp
            660                 665                 670

Val Arg Leu Leu Tyr Val Leu Ala Ile Ala Ala Leu Gly Gly Leu Cys
        675                 680                 685

Leu Ile Leu Ala Ser Ser Leu Leu Tyr Val Ala Cys Leu Arg Glu Gly
    690                 695                 700

Arg Arg Gly Arg Arg Arg Lys Tyr Ser Leu Gly Arg Ala Ser Arg Ala
705                 710                 715                 720

Gly Gly Ser Ala Val Gln Leu Gln Thr Val Ser Gly Arg Ala Leu Gln
                725                 730                 735

Val His Met Gly Ser Met Ser Pro Ser Ala Trp Pro Cys Val Leu
            740                 745                 750

Asp Gly Pro Glu Thr Arg Gln Val Leu Cys Gln Pro Pro Lys Pro Cys
        755                 760                 765
```

```
Val His Ser His Ala His Met Glu Glu Cys Leu Ser Ala Gly Leu Gln
    770                 775                 780

Cys Pro His Pro His Leu Leu Val His Ser Cys Phe Ile Pro Ala
785                 790                 795                 800

Ser Gly Leu Gly Val Pro Ser Gln Leu Pro His Pro Ile Trp Ser Ser
                805                 810                 815

Ser Pro Ala Pro Cys Gly Asp Leu Phe Val Lys Ser Leu Gly Thr Gly
                820                 825                 830

Gln Pro Gly Glu Val Arg Leu His His Ser Pro Pro Leu Pro Ser Cys
                835                 840                 845

Val Ala Leu Val Asn Gln Pro Pro His Ser Pro Trp Ser Phe Ser Arg
    850                 855                 860

Val
865

<210> SEQ ID NO 34
<211> LENGTH: 351
<212> TYPE: DNA
<213> ORGANISM: homo sapiens

<400> SEQUENCE: 34
atgcaaagca aatgtcatca aaagggaaa aacaaccaga cggagtgctt taaccatgtg    60
cggttcctgc agcggctcaa ttctacccac ctctatgcat gtgggactca cgccttccag   120
cccctctgtg cagccattga tgctgaggcc ttcaccttgc caaccagctt cgaggagggg   180
aaggagaagt gtccttatga cccagcccgt ggcttcacag gcctcatcat tgatggaggc   240
ctctacacag ccactaggta tgaattccgg agcattcctg acatccgccg agccgccac    300 ccacactccc tgagaactga ggagacacca atgcattggc tcaatggtta g           351

<210> SEQ ID NO 35
<211> LENGTH: 116
<212> TYPE: PRT
<213> ORGANISM: homo sapiens

<400> SEQUENCE: 35

Met Gln Ser Lys Cys His Gln Lys Gly Lys Asn Asn Gln Thr Glu Cys
1               5                   10                  15

Phe Asn His Val Arg Phe Leu Gln Arg Leu Asn Ser Thr His Leu Tyr
                20                  25                  30

Ala Cys Gly Thr His Ala Phe Gln Pro Leu Cys Ala Ala Ile Asp Ala
            35                  40                  45

Glu Ala Phe Thr Leu Pro Thr Ser Phe Glu Glu Gly Lys Glu Lys Cys
    50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Glu Thr Pro Met His
                100                 105                 110

Trp Leu Asn Gly
        115

<210> SEQ ID NO 36
<211> LENGTH: 1194
<212> TYPE: DNA
<213> ORGANISM: homo sapiens
```

<400> SEQUENCE: 36

```
atgcaaagca aatgtcatca aaaagggaaa acaaccaga cggagtgctt taaccatgtg       60
cggttcctgc agcggctcaa ttctacccac ctctatgcat gtgggactca cgccttccag      120
cccctctgtg cagccattga tgctgaggcc ttcaccttgc caaccagctt cgaggagggg      180
aaggagaagt gtccttatga cccagcccgt ggcttcacag gcctcatcat tgatggaggc      240
ctctacacag ccactaggta tgaattccgg agcattcctg acatccgccg gagccgccac      300
ccacactccc tgagaactga ggagacacca atgcattggc tcaatgatgc ggagtttgtg      360
ttctccgtcc tcgtgcggga gagcaaggcc agtgcagtgg gtgatgatga caaggtgtac      420
tacttcttca cggagcgtgc cactgaggag ggctctggca gcttcactca gagccgcagc      480
agtcaccgtg tggcccgtgt ggctcgygtc tgcaagggag acctgggagg aagaagatc       540
ctgcagaaga agtggacttc cttcctgaaa gcccgtctca tctgccacat tccactgtat      600
gagacactgc gtgggtctg cagcctggat gctgaaacct caagccgtac acacttctat       660
gcagccttca cgctgagcac acagtggaag accctggagg cctcagccat ctgccgctat      720
gacctggcag agatccaggc tgtctttgca ggaccctata tggaatacca ggatggttcc      780
cggcgctggg gtcgctatga gggtggggtg cctgagcccc ggcctggctc gtgtatcaca      840
gattcattgc gcagccaagg ctacaattca tcccaagact tgccatccct ggtcctggac      900
tttgtaaagt tgcacccact gatggctcgg cccgttgtgc ccacacgtgg acggcccctg      960
ctgctcaagc gcaacatacg ctacacacac cttacaggga cacctgtcac cacgcctgct     1020
ggacctacct atgacctgct ctttctgggc acagctgatg gctggatcca aaggccgta      1080
gtcctgggct ctgggatgca cattattgaa gagacacaag tgttcaggga gtcccagtct     1140
gtggaaaatc tagtcatctc tctattgcag gtagcccttc tctgtgaccc ttaa           1194
```

<210> SEQ ID NO 37
<211> LENGTH: 397
<212> TYPE: PRT
<213> ORGANISM: homo sapiens

<400> SEQUENCE: 37

```
Met Gln Ser Lys Cys His Gln Lys Gly Lys Asn Asn Gln Thr Glu Cys
1               5                   10                  15
Phe Asn His Val Arg Phe Leu Gln Arg Leu Asn Ser Thr His Leu Tyr
            20                  25                  30
Ala Cys Gly Thr His Ala Phe Gln Pro Leu Cys Ala Ala Ile Asp Ala
        35                  40                  45
Glu Ala Phe Thr Leu Pro Thr Ser Phe Glu Glu Gly Lys Glu Lys Cys
    50                  55                  60
Pro Tyr Asp Pro Ala Arg Gly Phe Thr Gly Leu Ile Ile Asp Gly Gly
65                  70                  75                  80
Leu Tyr Thr Ala Thr Arg Tyr Glu Phe Arg Ser Ile Pro Asp Ile Arg
                85                  90                  95
Arg Ser Arg His Pro His Ser Leu Arg Thr Glu Glu Thr Pro Met His
            100                 105                 110
Trp Leu Asn Asp Ala Glu Phe Val Phe Ser Val Leu Arg Glu Ser
        115                 120                 125
Lys Ala Ser Ala Val Gly Asp Asp Asp Lys Val Tyr Tyr Phe Phe Thr
    130                 135                 140
Glu Arg Ala Thr Glu Glu Gly Ser Gly Ser Phe Thr Gln Ser Arg Ser
145                 150                 155                 160
```

```
Ser His Arg Val Ala Arg Val Ala Arg Val Cys Lys Gly Asp Leu Gly
            165                 170                 175
Gly Lys Lys Ile Leu Gln Lys Lys Trp Thr Ser Phe Leu Lys Ala Arg
        180                 185                 190
Leu Ile Cys His Ile Pro Leu Tyr Glu Thr Leu Arg Gly Val Cys Ser
            195                 200                 205
Leu Asp Ala Glu Thr Ser Ser Arg Thr His Phe Tyr Ala Ala Phe Thr
210                 215                 220
Leu Ser Thr Gln Trp Lys Thr Leu Glu Ala Ser Ala Ile Cys Arg Tyr
225                 230                 235                 240
Asp Leu Ala Glu Ile Gln Ala Val Phe Ala Gly Pro Tyr Met Glu Tyr
            245                 250                 255
Gln Asp Gly Ser Arg Arg Trp Gly Arg Tyr Glu Gly Gly Val Pro Glu
            260                 265                 270
Pro Arg Pro Gly Ser Cys Ile Thr Asp Ser Leu Arg Ser Gln Gly Tyr
            275                 280                 285
Asn Ser Ser Gln Asp Leu Pro Ser Leu Val Leu Asp Phe Val Lys Leu
290                 295                 300
His Pro Leu Met Ala Arg Pro Val Pro Thr Arg Gly Arg Pro Leu
305                 310                 315                 320
Leu Leu Lys Arg Asn Ile Arg Tyr Thr His Leu Thr Gly Thr Pro Val
            325                 330                 335
Thr Thr Pro Ala Gly Pro Thr Tyr Asp Leu Leu Phe Leu Gly Thr Ala
            340                 345                 350
Asp Gly Trp Ile His Lys Ala Val Leu Gly Ser Gly Met His Ile
            355                 360                 365
Ile Glu Glu Thr Gln Val Phe Arg Glu Ser Gln Ser Val Glu Asn Leu
    370                 375                 380
Val Ile Ser Leu Leu Gln Val Ala Leu Leu Cys Asp Pro
385                 390                 395

<210> SEQ ID NO 38
<211> LENGTH: 1812
<212> TYPE: DNA
<213> ORGANISM: homo sapiens

<400> SEQUENCE: 38
atgcaaagca atgtcatca aaagggaaa acaaccaga cggagtgctt taaccatgtg        60
cggttcctgc agcggctcaa ttctacccac ctctatgcat gtgggactca cgccttccag    120
cccctctgtg cagccattga tgctgaggcc ttcaccttgc aaccagctt cgaggagggg     180 aaggagaagt gtccttatga cccagcccgt ggcttcacag gcctcatcat tgatggaggc    240
ctctacacag ccactaggta tgaattccgg agcattcctg acatccgccg agccgccac    300 ccacactccc tgagaactga ggagacacca atgcattggc tcaatgatgc ggagtttgtg    360
ttctccgtcc tcgtgcggga gagcaaggcc agtgcagtgg gtgatgatga caaggtgtac    420
tacttcttca cggagcgtgc cactgaggag ggctctggca gcttcactca gagccgcagc    480
agtcaccgtg tggcccgtgt ggctcgygtc tgcaagggag acctggggag gaagaagatc    540
ctgcagaaga gtggacttc cttcctgaaa gcccgtctca tctgccacat tccactgtat    600
gagacactgc gtgggtctg cagcctggat gctgaaacct caagccgtac acacttctat    660
gcagccttca cgctgagcac acagtggaag accctgagg cctcagccat ctgccgctat    720
gacctggcag agatccaggc tgtctttgca ggaccctata tggaatacca ggatggttcc    780
```

-continued

```
cggcgctggg gtcgctatga gggtggggtg cctgagcccc ggcctggctc gtgtatcaca    840
gattcattgc gcagccaagg ctacaattca tcccaagact tgccatccct ggtcctggac    900
tttgtaaagt tgcacccact gatggctcgg cccgttgtgc ccacacgtgg acggcccctg    960
ctgctcaagc gcaacatacg ctacacacac cttacaggga cacctgtcac cacgcctgct   1020
ggacctacct atgacctgct ctttctgggc acagctgatg gctggatcca caaggccgta   1080
gtcctgggct ctgggatgca cattattgaa gagacacaag tgttcaggga gtcccagtct   1140
gtggaaaatc tagtcatctc tctattgcag cacagcctct atgtgggggc tcctagcgga   1200
gtcatccagc taccactctc cagctgctcc cgctaccgat cctgctatga ctgcatcttg   1260
gcccgagacc cctactgtgg ctgggaccct ggcacccatg cctgcgcagc agccaccacc   1320
atagccaaca ggtcccaggg aagcaggaca gcactgatac aggacataga gagggaaat    1380
cgaggctgtg agagcagcag ggatacaggc agggctctgc aggtccatat gggctcaatg   1440
tcaccaccct ctgcatggcc ctgtgtgctg gatggtcctg aaaccagaca gtcctctgc    1500
cagccaccta gccctgcgt acattcacat gcacacatgg aagaatgttt atcggctggg    1560
ctgcagtgcc cccacccctca ccttctcctg gtgcattctt gtttcatccc tgcttctgga  1620
cttggggtac cctcccaatt gccacatcct atctggtcct cttccccagc ccatgtggt    1680
gacctctttg tcaagagctt gggaacgggc cagcctgggg aggtaagact gcatcactcc   1740
cctcctctcc cttcctgtgt ggcccttgtg aatcagcctc cccactctcc ttggtcattc   1800
tcaagagtat ga                                                       1812
```

<210> SEQ ID NO 39
<211> LENGTH: 603
<212> TYPE: PRT
<213> ORGANISM: homo sapiens

<400> SEQUENCE: 39

```
Met Gln Ser Lys Cys His Gln Lys Gly Lys Asn Asn Gln Thr Glu Cys
  1               5                  10                  15

Phe Asn His Val Arg Phe Leu Gln Arg Leu Asn Ser Thr His Leu Tyr
             20                  25                  30

Ala Cys Gly Thr His Ala Phe Gln Pro Leu Cys Ala Ala Ile Asp Ala
         35                  40                  45

Glu Ala Phe Thr Leu Pro Thr Ser Phe Glu Glu Gly Lys Glu Lys Cys
     50                  55                  60

Pro Tyr Asp Pro Ala Arg Gly Phe Thr Gly Leu Ile Ile Asp Gly Gly
 65                  70                  75                  80

Leu Tyr Thr Ala Thr Arg Tyr Glu Phe Arg Ser Ile Pro Asp Ile Arg
                 85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Val Arg Glu Ser
        115                 120                 125

Lys Ala Ser Ala Val Gly Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190
```

-continued

```
Leu Ile Cys His Ile Pro Leu Tyr Glu Thr Leu Arg Gly Val Cys Ser
            195                 200                 205

Leu Asp Ala Glu Thr Ser Ser Arg Thr His Phe Tyr Ala Ala Phe Thr
    210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
                245                 250                 255

Gln Asp Gly Ser Arg Arg Trp Gly Arg Tyr Glu Gly Gly Val Pro Glu
            260                 265                 270

Pro Arg Pro Gly Ser Cys Ile Thr Asp Ser Leu Arg Ser Gln Gly Tyr
        275                 280                 285

Asn Ser Ser Gln Asp Leu Pro Ser Leu Val Leu Asp Phe Val Lys Leu
290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                325                 330                 335

Thr Thr Pro Ala Gly Pro Thr Tyr Asp Leu Leu Phe Leu Gly Thr Ala
            340                 345                 350

Asp Gly Trp Ile His Lys Ala Val Val Leu Gly Ser Gly Met His Ile
        355                 360                 365

Ile Glu Glu Thr Gln Val Phe Arg Glu Ser Gln Ser Val Glu Asn Leu
370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                405                 410                 415

Asp Cys Ile Leu Ala Arg Asp Pro Tyr Cys Gly Trp Asp Pro Gly Thr
            420                 425                 430

His Ala Cys Ala Ala Thr Thr Ile Ala Asn Arg Ser Gln Gly Ser
        435                 440                 445

Arg Thr Ala Leu Ile Gln Asp Ile Glu Arg Gly Asn Arg Gly Cys Glu
450                 455                 460

Ser Ser Arg Asp Thr Gly Arg Ala Leu Gln Val His Met Gly Ser Met
465                 470                 475                 480

Ser Pro Pro Ser Ala Trp Pro Cys Val Leu Asp Gly Pro Glu Thr Arg
                485                 490                 495

Gln Val Leu Cys Gln Pro Pro Lys Pro Cys Val His Ser His Ala His
            500                 505                 510

Met Glu Glu Cys Leu Ser Ala Gly Leu Gln Cys Pro His Pro His Leu
        515                 520                 525

Leu Leu Val His Ser Cys Phe Ile Pro Ala Ser Gly Leu Gly Val Pro
530                 535                 540

Ser Gln Leu Pro His Pro Ile Trp Ser Ser Pro Ala Pro Cys Gly
545                 550                 555                 560

Asp Leu Phe Val Lys Ser Leu Gly Thr Gly Gln Pro Gly Glu Val Arg
                565                 570                 575

Leu His His Ser Pro Pro Leu Pro Ser Cys Val Ala Leu Val Asn Gln
            580                 585                 590

Pro Pro His Ser Pro Trp Ser Phe Ser Arg Val
        595                 600
```

<210> SEQ ID NO 40
<211> LENGTH: 1797
<212> TYPE: DNA
<213> ORGANISM: homo sapiens

<400> SEQUENCE: 40

| | | | | | | |
|---|---|---|---|---|---|---|
| atgcaaagca | aatgtcatca | aaaagggaaa | aacaaccaga | cggagtgctt | taaccatgtg | 60 |
| cggttcctgc | agcggctcaa | ttctacccac | ctctatgcat | gtgggactca | cgccttccag | 120 |
| cccctctgtg | cagccattga | tgctgaggcc | ttcaccttgc | caaccagctt | cgaggagggg | 180 |
| aaggagaagt | gtccttatga | cccagcccgt | ggcttcacag | gcctcatcat | tgatggaggc | 240 |
| ctctacacag | ccactaggta | tgaattccgg | agcattcctg | acatccgccg | gagccgccac | 300 |
| ccacactccc | tgagaactga | ggagacacca | atgcattggc | tcaatgatgc | ggagtttgtg | 360 |
| ttctccgtcc | tcgtgcggga | gagcaaggcc | agtgcagtgg | gtgatgatga | caaggtgtac | 420 |
| tacttcttca | cggagcgtgc | cactgaggag | ggctctggca | gcttcactca | gagccgcagc | 480 |
| agtcaccgtg | tggcccgtgt | ggctcgygtc | tgcaagggga | acctgggagg | gaagaagatc | 540 |
| ctgcagaaga | agtggacttc | cttcctgaaa | gcccgtctca | tctgccacat | tccactgtat | 600 |
| gagacactgc | gtgggtctg | cagcctggat | gctgaaacct | caagccgtac | acacttctat | 660 |
| gcagccttca | cgctgagcac | acagtggaag | accctggagg | cctcagccat | ctgccgctat | 720 |
| gacctggcag | agatccaggc | tgtctttgca | ggaccctata | tggaatacca | ggatggttcc | 780 |
| cggcgctggg | gtcgctatga | gggtggggtg | cctgagcccc | ggcctggctc | gtgtatcaca | 840 |
| gattcattgc | gcagccaagg | ctacaattca | tcccaagact | tgccatccct | ggtcctggac | 900 |
| tttgtaaagt | tgcacccact | gatggctcgg | cccgttgtgc | ccacacgtgg | acggcccctg | 960 |
| ctgctcaagc | gcaacatacg | ctacacacac | cttacaggga | cacctgtcac | cacgcctgct | 1020 |
| ggacctacct | atgacctgct | ctttctgggc | acagctgatg | gctggatcca | caggccgta | 1080 |
| gtcctgggct | ctgggatgca | cattattgaa | gagacacaag | tgttcaggga | gtcccagtct | 1140 |
| gtggaaaatc | tagtcatctc | tctattgcag | cacagcctct | atgtggggc | tcctagcgga | 1200 |
| gtcatccagc | taccactctc | cagctgctcc | cgctaccgat | cctgctatga | ctgcatcttg | 1260 |
| gcccgagacc | cctactgtgg | ctgggaccct | ggcacccatg | cctgcgcagc | agccaccacc | 1320 |
| atagccaaca | ggacagcact | gatacaggac | atagagagag | gaaatcgagg | ctgtgagagc | 1380 |
| agcagggata | caggcaggc | tctgcaggtc | catatgggct | caatgtcacc | accctctgca | 1440 |
| tggccctgtg | tgctggatgg | tcctgaaacc | agacaagtcc | tctgccagcc | acctaagccc | 1500 |
| tgcgtacatt | cacatgcaca | catggaagaa | tgtttatcgg | ctgggctgca | gtgccccac | 1560 |
| cctcaccttc | tcctggtgca | ttcttgtttc | atccctgctt | ctggacttgg | ggtaccctcc | 1620 |
| caattgccac | atcctatctg | gtcctcttcc | ccagccccat | gtggtgacct | ctttgtcaag | 1680 |
| agcttgggaa | cgggccagcc | tggggaggta | agactgcatc | actcccctcc | tctcccttcc | 1740 |
| tgtgtggccc | ttgtgaatca | gcctccccac | tctccttggt | cattctcaag | agtatga | 1797 |

<210> SEQ ID NO 41
<211> LENGTH: 598
<212> TYPE: PRT
<213> ORGANISM: homo sapiens -continued

<400> SEQUENCE: 41

| | | | | | | | | | | | | | | | |
|---|---|---|---|---|---|---|---|---|---|---|---|---|---|---|---|

Met Gln Ser Lys Cys His Gln Lys Gly Lys Asn Asn Gln Thr Glu Cys
1               5                       10                      15

Phe Asn His Val Arg Phe Leu Gln Arg Leu Asn Ser Thr His Leu Tyr
            20                      25                  30

Ala Cys Gly Thr His Ala Phe Gln Pro Leu Cys Ala Ala Ile Asp Ala
        35                      40                  45

Glu Ala Phe Thr Leu Pro Thr Ser Phe Glu Gly Lys Glu Lys Cys
50                      55                  60

Pro Tyr Asp Pro Ala Arg Gly Phe Thr Gly Leu Ile Ile Asp Gly Gly
65                  70                      75                      80

Leu Tyr Thr Ala Thr Arg Tyr Glu Phe Arg Ser Ile Pro Asp Ile Arg
                85                      90                      95

Arg Ser Arg His Pro His Ser Leu Arg Thr Glu Glu Thr Pro Met His
                100                     105                 110

Trp Leu Asn Asp Ala Glu Phe Val Phe Ser Val Leu Val Arg Glu Ser
                115                     120                 125

Lys Ala Ser Ala Val Gly Asp Asp Lys Val Tyr Tyr Phe Phe Thr
130                     135                 140

Glu Arg Ala Thr Glu Glu Gly Ser Gly Ser Phe Thr Gln Ser Arg Ser
145                     150                 155                 160

Ser His Arg Val Ala Arg Val Ala Arg Val Cys Lys Gly Asp Leu Gly
                165                     170                 175

Gly Lys Lys Ile Leu Gln Lys Lys Trp Thr Ser Phe Leu Lys Ala Arg
                180                     185                 190

Leu Ile Cys His Ile Pro Leu Tyr Glu Thr Leu Arg Gly Val Cys Ser
                195                     200                 205

Leu Asp Ala Glu Thr Ser Ser Arg Thr His Phe Tyr Ala Ala Phe Thr
                210                     215                 220

Leu Ser Thr Gln Trp Lys Thr Leu Glu Ala Ser Ala Ile Cys Arg Tyr
225                     230                     235                 240

Asp Leu Ala Glu Ile Gln Ala Val Phe Ala Gly Pro Tyr Met Glu Tyr
                245                     250                 255

Gln Asp Gly Ser Arg Arg Trp Gly Arg Tyr Glu Gly Gly Val Pro Glu
                260                     265                 270

Pro Arg Pro Gly Ser Cys Ile Thr Asp Ser Leu Arg Ser Gln Gly Tyr
                275                     280                 285

Asn Ser Ser Gln Asp Leu Pro Ser Leu Val Leu Asp Phe Val Lys Leu
                290                     295                 300

His Pro Leu Met Ala Arg Pro Val Val Pro Thr Arg Gly Arg Pro Leu
305                     310                     315                 320

Leu Leu Lys Arg Asn Ile Arg Tyr Thr His Leu Thr Gly Thr Pro Val
                325                     330                 335

Thr Thr Pro Ala Gly Pro Thr Tyr Asp Leu Leu Phe Leu Gly Thr Ala
                340                     345                 350

Asp Gly Trp Ile His Lys Ala Val Val Leu Gly Ser Gly Met His Ile
                355                     360                 365

Ile Glu Glu Thr Gln Val Phe Arg Glu Ser Gln Ser Val Glu Asn Leu
                370                     375                 380

Val Ile Ser Leu Leu Gln His Ser Leu Tyr Val Gly Ala Pro Ser Gly
385                     390                     395                 400

Val Ile Gln Leu Pro Leu Ser Ser Cys Ser Arg Tyr Arg Ser Cys Tyr
                405                     410                 415

```
Asp Cys Ile Leu Ala Arg Asp Pro Tyr Cys Gly Trp Asp Pro Gly Thr
            420                 425                 430
His Ala Cys Ala Ala Thr Thr Ile Ala Asn Arg Thr Ala Leu Ile
        435                 440                 445
Gln Asp Ile Glu Arg Gly Asn Arg Gly Cys Glu Ser Ser Arg Asp Thr
    450                 455                 460
Gly Arg Ala Leu Gln Val His Met Gly Ser Met Ser Pro Pro Ser Ala
465                 470                 475                 480
Trp Pro Cys Val Leu Asp Gly Pro Glu Thr Arg Gln Val Leu Cys Gln
                485                 490                 495
Pro Pro Lys Pro Cys Val His Ser His Ala His Met Glu Glu Cys Leu
            500                 505                 510
Ser Ala Gly Leu Gln Cys Pro His Pro His Leu Leu Leu Val His Ser
        515                 520                 525
Cys Phe Ile Pro Ala Ser Gly Leu Gly Val Pro Ser Gln Leu Pro His
    530                 535                 540
Pro Ile Trp Ser Ser Pro Ala Pro Cys Gly Asp Leu Phe Val Lys
545                 550                 555                 560
Ser Leu Gly Thr Gly Gln Pro Gly Glu Val Arg Leu His His Ser Pro
                565                 570                 575
Pro Leu Pro Ser Cys Val Ala Leu Val Asn Gln Pro Pro His Ser Pro
            580                 585                 590
Trp Ser Phe Ser Arg Val
        595

<210> SEQ ID NO 42
<211> LENGTH: 2235
<212> TYPE: DNA
<213> ORGANISM: homo sapiens

<400> SEQUENCE: 42
atgcaaagca aatgtcatca aaagggaaa acaaccaga cggagtgctt taaccatgtg      60
cggttcctgc agcggctcaa ttctacccac tctctatgcat gtgggactca cgccttccag   120
cccctctgtg cagccattga tgctgaggcc ttcaccttgc caaccagctt cgaggagggg   180
aaggagaagt gtccttatga cccagcccgt ggcttcacag gcctcatcat tgatggaggc   240
ctctacacag ccactaggta tgaattccgg agcattcctg acatccgccg gagccgccac   300
ccacactccc tgagaactga ggagacacca atgcattggc tcaatgatgc ggagtttgtg   360
ttctccgtcc tcgtgcggga gagcaaggcc agtgcagtgg gtgatgatga caaggtgtac   420
tacttcttca cggagcgtgc cactgaggag ggctctggca gcttcactca gagccgcagc   480
agtcaccgtg tggcccgtgt ggctcgygtc tgcaagggag acctgggagg aagaagatc    540 ctgcagaaga gtggacttc cttcctgaaa gcccgtctca tctgccacat tccactgtat    600
gagacactgc gtgggtctg cagcctggat gctgaaacct caagccgtac acacttctat   660
gcagccttca cgctgagcac acagtggaag accctggagg cctcagccat ctgccgctat   720
gacctggcag agatccaggc tgtctttgca ggaccctata tggaatacca ggatggttcc   780
cggcgctggg gtcgctatga gggtggggtg cctgagcccc ggcctggctc gtgtatcaca   840
gattcattgc gcagccaagg ctacaattca tcccaagact tgccatccct ggtcctggac   900
tttgtaaagt tgcacccact gatggctcgg cccgttgtgc ccacacgtgg acggcccctg   960
ctgctcaagc gcaacatacg ctacacacac cttacaggga cacctgtcac cacgcctgct  1020
ggacctacct atgacctgct ctttctgggc acagctgatg gctggatcca caaggccgta  1080
```

```
gtcctgggct ctgggatgca cattattgaa gagacacaag tgttcaggga gtcccagtct    1140
gtggaaaatc tagtcatctc tctattgcag cacagcctct atgtgggggc tcctagcgga    1200
gtcatccagc taccactctc cagctgctcc cgctaccgat cctgctatga ctgcatcttg    1260
gcccgagacc cctactgtgg ctgggaccct ggcacccatg cctgcgcagc agccaccacc    1320
atagccaaca ggtcccaggg aagcaggaca gcactgatac aggacataga gagaggaaat    1380
cgaggctgtg agagcagcag ggatacaggg ccaccaccac cactgaagac ccgctctgtg    1440
ctccggggtg atgatgtcct cctgccctgt gaccagccat ccaacctggc ccgggccttg    1500
tggctactca atgggagcat gggcctgagc gatgggcagg gtggctaccg tgtgggcgtg    1560
gacgggctgc tggttacaga tgcacagcct gagcacagtg gcaactatgg ctgctatgcc    1620
gaggaaaatg gcctccgcac cctgctggcc tcctatagtc tcacagtccg gccagccact    1680
cctgccccag ctccaaaagc ccctgccaca cctggggcac agctggcacc tgatgtgaga    1740
ctgctctatg tgctagccat tgccgcgctt ggtggccyct gcctcatcct ggcctcctcc    1800
ctcctctatg tggcctgtct gcgggaaggc agacgagggc gccgacggaa atactcactg    1860
ggtcgggcca gccgggcagg aggatctgcg gtgcaactgc agacagtctc aggccagtgt    1920
cctggagagg aagatgaggg tgatgatgag ggggctgggg gcctggaggg cagctgtctc    1980
cagatcatcc ctggggaggg agccccagcc ccaccacccc caccgccccc accgccaccg    2040
gctgagctga ccaatggctt ggtggcactg cccagccggc tgcggaggat gaatggcaat    2100
agctatgtgc ttctgaggca gagcaacaat ggagtaccag cagggccctg ctccttcgcc    2160
gaggaactca gccgcatcct ggaaaaaagg aagcacacgc agctcgtgga gcagctagat    2220
gagagctctg tctga                                                    2235

<210> SEQ ID NO 43
<211> LENGTH: 744
<212> TYPE: PRT
<213> ORGANISM: homo sapiens

<400> SEQUENCE: 43

Met Gln Ser Lys Cys His Gln Lys Gly Lys Asn Asn Gln Thr Glu Cys
 1               5                  10                  15

Phe Asn His Val Arg Phe Leu Gln Arg Leu Asn Ser Thr His Leu Tyr
            20                  25                  30

Ala Cys Gly Thr His Ala Phe Gln Pro Leu Cys Ala Ala Ile Asp Ala
        35                  40                  45

Glu Ala Phe Thr Leu Pro Thr Ser Phe Glu Glu Gly Lys Glu Lys Cys
    50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Arg Glu Ser
            115                 120                 125

Lys Ala Ser Ala Val Gly Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160
```

-continued

```
Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
        195                 200                 205

Leu Asp Ala Glu Thr Ser Ser Arg Thr His Phe Tyr Ala Ala Phe Thr
    210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
                245                 250                 255

Gln Asp Gly Ser Arg Arg Trp Gly Arg Tyr Glu Gly Gly Val Pro Glu
            260                 265                 270

Pro Arg Pro Gly Ser Cys Ile Thr Asp Ser Leu Arg Ser Gln Gly Tyr
        275                 280                 285

Asn Ser Ser Gln Asp Leu Pro Ser Leu Val Leu Asp Phe Val Lys Leu
    290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                325                 330                 335

Thr Thr Pro Ala Gly Pro Thr Tyr Asp Leu Leu Phe Leu Gly Thr Ala
            340                 345                 350

Asp Gly Trp Ile His Lys Ala Val Leu Gly Ser Gly Met His Ile
        355                 360                 365

Ile Glu Glu Thr Gln Val Phe Arg Glu Ser Gln Ser Val Glu Asn Leu
    370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                405                 410                 415

Asp Cys Ile Leu Ala Arg Asp Pro Tyr Cys Gly Trp Asp Pro Gly Thr
            420                 425                 430

His Ala Cys Ala Ala Ala Thr Thr Ile Ala Asn Arg Ser Gln Gly Ser
        435                 440                 445

Arg Thr Ala Leu Ile Gln Asp Ile Glu Arg Gly Asn Arg Gly Cys Glu
    450                 455                 460

Ser Ser Arg Asp Thr Gly Pro Pro Pro Leu Lys Thr Arg Ser Val
465                 470                 475                 480

Leu Arg Gly Asp Asp Val Leu Leu Pro Cys Asp Gln Pro Ser Asn Leu
                485                 490                 495

Ala Arg Ala Leu Trp Leu Leu Asn Gly Ser Met Gly Leu Ser Asp Gly
            500                 505                 510

Gln Gly Gly Tyr Arg Val Gly Val Asp Gly Leu Leu Val Thr Asp Ala
        515                 520                 525

Gln Pro Glu His Ser Gly Asn Tyr Gly Cys Tyr Ala Glu Glu Asn Gly
    530                 535                 540

Leu Arg Thr Leu Leu Ala Ser Tyr Ser Leu Thr Val Arg Pro Ala Thr
545                 550                 555                 560

Pro Ala Pro Ala Pro Lys Ala Pro Ala Thr Pro Gly Ala Gln Leu Ala
                565                 570                 575
```

-continued

```
Pro Asp Val Arg Leu Leu Tyr Val Leu Ala Ile Ala Ala Leu Gly Gly
            580                 585                 590
Leu Cys Leu Ile Leu Ala Ser Ser Leu Leu Tyr Val Ala Cys Leu Arg
        595                 600                 605
Glu Gly Arg Arg Gly Arg Arg Lys Tyr Ser Leu Gly Arg Ala Ser
    610                 615                 620
Arg Ala Gly Gly Ser Ala Val Gln Leu Gln Thr Val Ser Gly Gln Cys
625                 630                 635                 640
Pro Gly Glu Glu Asp Glu Gly Asp Asp Glu Gly Ala Gly Gly Leu Glu
                645                 650                 655
Gly Ser Cys Leu Gln Ile Ile Pro Gly Gly Ala Pro Ala Pro Pro
            660                 665                 670
Pro Pro Pro Pro Pro Pro Pro Ala Glu Leu Thr Asn Gly Leu Val
        675                 680                 685
Ala Leu Pro Ser Arg Leu Arg Arg Met Asn Gly Asn Ser Tyr Val Leu
    690                 695                 700
Leu Arg Gln Ser Asn Asn Gly Val Pro Ala Gly Pro Cys Ser Phe Ala
705                 710                 715                 720
Glu Glu Leu Ser Arg Ile Leu Glu Lys Arg Lys His Thr Gln Leu Val
                725                 730                 735
Glu Gln Leu Asp Glu Ser Ser Val
            740
```

<210> SEQ ID NO 44
<211> LENGTH: 2220
<212> TYPE: DNA
<213> ORGANISM: homo sapiens

<400> SEQUENCE: 44

| | | |
|---|---|---|
| atgcaaagca aatgtcatca aaaagggaaa acaaccaga cggagtgctt taaccatgtg | 60 |
| cggttcctgc agcggctcaa ttctacccac ctctatgcat gtgggactca cgccttccag | 120 |
| cccctctgtg cagccattga tgctgaggcc ttcaccttgc aaccagctt cgaggagggg | 180 |
| aaggagaagt gtccttatga cccagcccgt ggcttacag gcctcatcat tgatggaggc | 240 |
| ctctacacag ccactaggta tgaattccgg agcattcctg acatccgccg agccgccac | 300 |
| ccacactccc tgagaactga ggagacacca atgcattggc tcaatgatgc ggagtttgtg | 360 |
| ttctccgtcc tcgtgcggga gagcaaggcc agtgcagtgg gtgatgatga caaggtgtac | 420 |
| tacttcttca cggagcgtgc cactgaggag ggctctggca gcttcactca gagccgcagc | 480 |
| agtcaccgtg tggcccgtgt ggctcgygtc tgcaagggag acctgggagg gaagaagatc | 540 |
| ctgcagaaga gtggacttc cttcctgaaa gcccgtctca tctgccacat tccactgtat | 600 |
| gagacactgc gtgggtctg cagcctggat gctgaaacct caagccgtac acacttctat | 660 |
| gcagccttca cgctgagcac acagtggaag accctggagg cctcagccat ctgccgctat | 720 |
| gacctggcag agatccaggc tgtctttgca ggaccctata tggaatacca ggatggttcc | 780 |
| cggcgctggg gtcgctatga gggtgggggtg cctgagcccc ggcctggctc gtgtatcaca | 840 |
| gattcattgc gcagccaagg ctacaattca tcccaagact tgccatccct ggtcctggac | 900 |
| tttgtaaagt tgcacccact gatggctcgg cccgttgtgc ccacacgtgg acggcccctg | 960 |
| ctgctcaagc gcaacatacg ctacacacac cttacaggga cacctgtcac cacgcctgct | 1020 |
| ggacctacct atgacctgct ctttctgggc acagctgatg gctggatcca aaggccgta | 1080 |
| gtcctgggct ctgggatgca cattattgaa gagacacaag tgttcaggga gtcccagtct | 1140 |

-continued

```
gtggaaaatc tagtcatctc tctattgcag cacagcctct atgtgggggc tcctagcgga   1200
gtcatccagc taccactctc cagctgctcc cgctaccgat cctgctatga ctgcatcttg   1260
gcccgagacc cctactgtgg ctgggaccct ggcacccatg cctgcgcagc agccaccacc   1320
atagccaaca ggacagcact gatacaggac atagagagag gaaatcgagg ctgtgagagc   1380
agcagggata cagggccacc accaccactg aagacccgct ctgtgctccg gggtgatgat   1440
gtcctcctgc cctgtgacca gccatccaac ctggcccggg ccttgtggct actcaatggg   1500
agcatgggcc tgagcgatgg gcagggtggc taccgtgtgg gcgtggacgg gctgctggtt   1560
acagatgcac agcctgagca cagtggcaac tatggctgct atgccgagga aaatggcctc   1620
cgcaccctgc tggcctccta tagtctcaca gtccggccag ccactcctgc cccagctcca   1680
aaagcccctg ccacacctgg ggcacagctg gcacctgatg tgagactgct ctatgtgcta   1740
gccattgccg cgcttggtgg ccyctgcctc atcctggcct cctccctcct ctatgtggcc   1800
tgtctgcggg aaggcagacg agggcgccga cggaaatact cactgggtcg ggccagccgg   1860
gcaggaggat ctgcggtgca actgcagaca gtctcaggcc agtgtcctgg agaggaagat   1920
gagggtgatg atgagggggc tgggggcctg gagggcagct gtctccagat catccctggg   1980
gagggagccc cagccccacc accccaccg ccccaccgc caccggctga gctgaccaat   2040
ggcttggtgg cactgcccag ccggctgcgg aggatgaatg caatagcta tgtgcttctg   2100
aggcagagca acaatggagt accagcaggg ccctgctcct tcgccgagga actcagccgc   2160
atcctggaaa aaaggaagca cacgcagctc gtggagcagc tagatgagag ctctgtctga   2220
```

<210> SEQ ID NO 45
<211> LENGTH: 739
<212> TYPE: PRT
<213> ORGANISM: homo sapiens

<400> SEQUENCE: 45

```
Met Gln Ser Lys Cys His Gln Lys Gly Lys Asn Asn Gln Thr Glu Cys
 1               5                  10                  15

Phe Asn His Val Arg Phe Leu Gln Arg Leu Asn Ser Thr His Leu Tyr
            20                  25                  30

Ala Cys Gly Thr His Ala Phe Gln Pro Leu Cys Ala Ala Ile Asp Ala
        35                  40                  45

Glu Ala Phe Thr Leu Pro Thr Ser Phe Glu Glu Gly Lys Glu Lys Cys
    50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Val Arg Glu Ser
        115                 120                 125

Lys Ala Ser Ala Val Gly Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190
```

-continued

Leu Ile Cys His Ile Pro Leu Tyr Glu Thr Leu Arg Gly Val Cys Ser
            195                 200                 205

Leu Asp Ala Glu Thr Ser Ser Arg Thr His Phe Tyr Ala Ala Phe Thr
    210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
                245                 250                 255

Gln Asp Gly Ser Arg Arg Trp Gly Arg Tyr Glu Gly Gly Val Pro Glu
            260                 265                 270

Pro Arg Pro Gly Ser Cys Ile Thr Asp Ser Leu Arg Ser Gln Gly Tyr
        275                 280                 285

Asn Ser Ser Gln Asp Leu Pro Ser Leu Val Leu Asp Phe Val Lys Leu
290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                325                 330                 335

Thr Thr Pro Ala Gly Pro Thr Tyr Asp Leu Leu Phe Leu Gly Thr Ala
            340                 345                 350

Asp Gly Trp Ile His Lys Ala Val Val Leu Gly Ser Gly Met His Ile
        355                 360                 365

Ile Glu Glu Thr Gln Val Phe Arg Glu Ser Gln Ser Val Glu Asn Leu
    370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                405                 410                 415

Asp Cys Ile Leu Ala Arg Asp Pro Tyr Cys Gly Trp Asp Pro Gly Thr
            420                 425                 430

His Ala Cys Ala Ala Ala Thr Thr Ile Ala Asn Arg Thr Ala Leu Ile
        435                 440                 445

Gln Asp Ile Glu Arg Gly Asn Arg Gly Cys Glu Ser Ser Arg Asp Thr
    450                 455                 460

Gly Pro Pro Pro Leu Lys Thr Arg Ser Val Leu Arg Gly Asp Asp
465                 470                 475                 480

Val Leu Leu Pro Cys Asp Gln Pro Ser Asn Leu Ala Arg Ala Leu Trp
                485                 490                 495

Leu Leu Asn Gly Ser Met Gly Leu Ser Asp Gly Gln Gly Gly Tyr Arg
            500                 505                 510

Val Gly Val Asp Gly Leu Leu Val Thr Asp Ala Gln Pro Glu His Ser
        515                 520                 525

Gly Asn Tyr Gly Cys Tyr Ala Glu Glu Asn Gly Leu Arg Thr Leu Leu
    530                 535                 540

Ala Ser Tyr Ser Leu Thr Val Arg Pro Ala Thr Pro Ala Pro Ala Pro
545                 550                 555                 560

Lys Ala Pro Ala Thr Pro Gly Ala Gln Leu Ala Pro Asp Val Arg Leu
                565                 570                 575

Leu Tyr Val Leu Ala Ile Ala Ala Leu Gly Gly Leu Cys Leu Ile Leu
            580                 585                 590

Ala Ser Ser Leu Leu Tyr Val Ala Cys Leu Arg Glu Gly Arg Arg Gly
        595                 600                 605

```
                  Arg Arg Arg Lys Tyr Ser Leu Gly Arg Ala Ser Arg Ala Gly Gly Ser
                      610                 615                 620

Ala Val Gln Leu Gln Thr Val Ser Gly Gln Cys Pro Gly Glu Glu Asp
                  625                 630                 635                 640

Glu Gly Asp Asp Glu Gly Ala Gly Gly Leu Glu Gly Ser Cys Leu Gln
                                  645                 650                 655

Ile Ile Pro Gly Glu Gly Ala Pro Ala Pro Pro Pro Pro Pro Pro Pro
                              660                 665                 670

Pro Pro Pro Ala Glu Leu Thr Asn Gly Leu Val Ala Leu Pro Ser Arg
                          675                 680                 685

Leu Arg Arg Met Asn Gly Asn Ser Tyr Val Leu Leu Arg Gln Ser Asn
                      690                 695                 700

Asn Gly Val Pro Ala Gly Pro Cys Ser Phe Ala Glu Glu Leu Ser Arg
                  705                 710                 715                 720

Ile Leu Glu Lys Arg Lys His Thr Gln Leu Val Glu Gln Leu Asp Glu
                                  725                 730                 735

Ser Ser Val
```

<210> SEQ ID NO 46
<211> LENGTH: 2316
<212> TYPE: DNA
<213> ORGANISM: homo sapiens

<400> SEQUENCE: 46

| | | | | | |
|---|---|---|---|---|---|
| atgcaaagca | aatgtcatca | aaaagggaaa | acaaccaga | cggagtgctt | taaccatgtg | 60 |
| cggttcctgc | agcggctcaa | ttctacccac | ctctatgcat | gtgggactca | cgccttccag | 120 |
| cccctctgtg | cagccattga | tgctgaggcc | ttcaccttgc | aaccagctt | cgaggagggg | 180 |
| aaggagaagt | gtccttatga | cccagcccgt | ggcttacag | gcctcatcat | tgatggaggc | 240 |
| ctctacacag | ccactaggta | tgaattccgg | agcattcctg | catccgccg | gagccgccac | 300 |
| ccacactccc | tgagaactga | ggagacacca | atgcattggc | tcaatgatgc | ggagtttgtg | 360 |
| ttctccgtcc | tcgtgcggga | gagcaaggcc | agtgcagtgg | gtgatgatga | caaggtgtac | 420 |
| tacttcttca | cggagcgtgc | cactgaggag | ggctctggca | gcttcactca | gagccgcagc | 480 |
| agtcaccgtg | tggcccgtgt | ggctcgygtc | tgcaagggag | acctgggagg | gaagaagatc | 540 |
| ctgcagaaga | agtggacttc | cttcctgaaa | gcccgtctca | tctgccacat | tccactgtat | 600 |
| gagacactgc | gtgggtctg | cagcctggat | gctgaaacct | caagccgtac | acacttctat | 660 |
| gcagccttca | cgctgagcac | acagtggaag | acctggagg | cctcagccat | ctgccgctat | 720 |
| gacctggcag | agatccaggc | tgtctttgca | ggaccctata | tggaatacca | ggatggttcc | 780 |
| cggcgctggg | gtcgctatga | gggtgggggtg | cctgagcccc | ggcctggctc | gtgtatcaca | 840 |
| gattcattgc | gcagccaagg | ctacaattca | tcccaagact | tgccatccct | ggtcctggac | 900 |
| tttgtaaagt | tgcacccact | gatggctcgg | cccgttgtgc | ccacacgtgg | acggcccctg | 960 |
| ctgctcaagc | gcaacatacg | ctacacacac | cttacaggga | cacctgtcac | cacgcctgct | 1020 |
| ggacctacct | atgacctgct | ctttctgggc | acagctgatg | ctggatcca | caaggccgta | 1080 |
| gtcctgggct | ctgggatgca | cattattgaa | gagacacaag | tgttcaggga | gtcccagtct | 1140 |
| gtggaaaatc | tagtcatctc | tctattgcag | cacagcctct | atgtgggggc | tcctagcgga | 1200 |
| gtcatccagc | taccactctc | cagctgctcc | cgctaccgat | cctgctatga | ctgcatcttg | 1260 |
| gcccgagacc | cctactgtgg | ctgggaccct | gcacccatg | cctgcgcagc | agccaccacc | 1320 |
| atagccaaca | ggtcccaggg | aagcaggaca | gcactgatac | aggacataga | gagaggaaat | 1380 |

-continued

```
cgaggctgtg agagcagcag ggatacaggg ccaccaccac cactgaagac ccgctctgtg    1440
ctccggggtg atgatgtcct cctgccctgt gaccagccat ccaacctggc ccgggccttg    1500
tggctactca atgggagcat gggcctgagc gatgggcagg gtggctaccg tgtgggcgtg    1560
gacgggctgc tggttacaga tgcacagcct gagcacagtg gcaactatgg ctgctatgcc    1620
gaggaaaatg gcctccgcac cctgctggcc tcctatagtc tcacagtccg gccagccact    1680
cctgccccag ctccaaaagc ccctgccaca cctgggcac agctggcacc tgatgtgaga     1740
ctgctctatg tgctagccat tgccgcgctt ggtggccyct gcctcatcct ggcctcctcc    1800
ctcctctatg tggcctgtct gcgggaaggc agacgagggc gccgacggaa atactcactg    1860
ggtcgggcca gccgggcagg aggatctgcg gtgcaactgc agacagtctc aggcagggct    1920
ctgcaggtcc atatgggctc aatgtcacca ccctctgcat ggccctgtgt gctggatggt    1980
cctgaaacca gacaagtcct ctgccagcca cctaagccct gcgtacattc acatgcacac    2040
atggaagaat gtttatcggc tgggctgcag tgcccccacc ctcaccttct cctggtgcat    2100
tcttgtttca tccctgcttc tggacttggg gtaccctccc aattgccaca tcctatctgg    2160
tcctcttccc cagccccatg tggtgacctc tttgtcaaga gcttgggaac gggccagcct    2220
ggggaggtaa gactgcatca ctcccctcct ctcccttcct gtgtggccct tgtgaatcag    2280
cctcccact ctccttggtc attctcaaga gtatga                              2316
```

<210> SEQ ID NO 47
<211> LENGTH: 771
<212> TYPE: PRT
<213> ORGANISM: homo sapiens

<400> SEQUENCE: 47

```
Met Gln Ser Lys Cys His Gln Lys Gly Lys Asn Asn Gln Thr Glu Cys
 1               5                  10                  15

Phe Asn His Val Arg Phe Leu Gln Arg Leu Asn Ser Thr His Leu Tyr
            20                  25                  30

Ala Cys Gly Thr His Ala Phe Gln Pro Leu Cys Ala Ala Ile Asp Ala
        35                  40                  45

Glu Ala Phe Thr Leu Pro Thr Ser Phe Glu Glu Gly Lys Glu Lys Cys
    50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Val Arg Glu Ser
        115                 120                 125

Lys Ala Ser Ala Val Gly Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
        195                 200                 205
```

-continued

```
Leu Asp Ala Glu Thr Ser Ser Arg Thr His Phe Tyr Ala Ala Phe Thr
210                 215                 220
Leu Ser Thr Gln Trp Lys Thr Leu Glu Ala Ser Ala Ile Cys Arg Tyr
225                 230                 235                 240
Asp Leu Ala Glu Ile Gln Ala Val Phe Ala Gly Pro Tyr Met Glu Tyr
                245                 250                 255
Gln Asp Gly Ser Arg Arg Trp Gly Arg Tyr Glu Gly Gly Val Pro Glu
            260                 265                 270
Pro Arg Pro Gly Ser Cys Ile Thr Asp Ser Leu Arg Ser Gln Gly Tyr
        275                 280                 285
Asn Ser Ser Gln Asp Leu Pro Ser Leu Val Leu Asp Phe Val Lys Leu
290                 295                 300
His Pro Leu Met Ala Arg Pro Val Val Pro Thr Arg Gly Arg Pro Leu
305                 310                 315                 320
Leu Leu Lys Arg Asn Ile Arg Tyr Thr His Leu Thr Gly Thr Pro Val
                325                 330                 335
Thr Thr Pro Ala Gly Pro Thr Tyr Asp Leu Leu Phe Leu Gly Thr Ala
            340                 345                 350
Asp Gly Trp Ile His Lys Ala Val Val Leu Gly Ser Gly Met His Ile
        355                 360                 365
Ile Glu Glu Thr Gln Val Phe Arg Glu Ser Gln Ser Val Glu Asn Leu
370                 375                 380
Val Ile Ser Leu Leu Gln His Ser Leu Tyr Val Gly Ala Pro Ser Gly
385                 390                 395                 400
Val Ile Gln Leu Pro Leu Ser Ser Cys Ser Arg Tyr Arg Ser Cys Tyr
                405                 410                 415
Asp Cys Ile Leu Ala Arg Asp Pro Tyr Cys Gly Trp Asp Pro Gly Thr
            420                 425                 430
His Ala Cys Ala Ala Ala Thr Thr Ile Ala Asn Arg Ser Gln Gly Ser
        435                 440                 445
Arg Thr Ala Leu Ile Gln Asp Ile Glu Arg Gly Asn Arg Gly Cys Glu
450                 455                 460
Ser Ser Arg Asp Thr Gly Pro Pro Pro Leu Lys Thr Arg Ser Val
465                 470                 475                 480
Leu Arg Gly Asp Asp Val Leu Leu Pro Cys Asp Gln Pro Ser Asn Leu
                485                 490                 495
Ala Arg Ala Leu Trp Leu Leu Asn Gly Ser Met Gly Leu Ser Asp Gly
            500                 505                 510
Gln Gly Gly Tyr Arg Val Gly Val Asp Gly Leu Leu Val Thr Asp Ala
        515                 520                 525
Gln Pro Glu His Ser Gly Asn Tyr Gly Cys Tyr Ala Glu Glu Asn Gly
530                 535                 540
Leu Arg Thr Leu Leu Ala Ser Tyr Ser Leu Thr Val Arg Pro Ala Thr
545                 550                 555                 560
Pro Ala Pro Ala Pro Lys Ala Pro Ala Thr Pro Gly Ala Gln Leu Ala
                565                 570                 575
Pro Asp Val Arg Leu Leu Tyr Val Leu Ala Ile Ala Ala Leu Gly Gly
            580                 585                 590
Leu Cys Leu Ile Leu Ala Ser Ser Leu Leu Tyr Val Ala Cys Leu Arg
        595                 600                 605
Glu Gly Arg Arg Gly Arg Arg Lys Tyr Ser Leu Gly Arg Ala Ser
610                 615                 620
```

```
Arg Ala Gly Gly Ser Ala Val Gln Leu Gln Thr Val Ser Gly Arg Ala
625                 630                 635                 640

Leu Gln Val His Met Gly Ser Met Ser Pro Pro Ser Ala Trp Pro Cys
            645                 650                 655

Val Leu Asp Gly Pro Glu Thr Arg Gln Val Leu Cys Gln Pro Pro Lys
        660                 665                 670

Pro Cys Val His Ser His Ala His Met Glu Glu Cys Leu Ser Ala Gly
            675                 680                 685

Leu Gln Cys Pro His Pro His Leu Leu Leu Val His Ser Cys Phe Ile
690                 695                 700

Pro Ala Ser Gly Leu Gly Val Pro Ser Gln Leu Pro His Pro Ile Trp
705                 710                 715                 720

Ser Ser Ser Pro Ala Pro Cys Gly Asp Leu Phe Val Lys Ser Leu Gly
                725                 730                 735

Thr Gly Gln Pro Gly Glu Val Arg Leu His His Ser Pro Pro Leu Pro
            740                 745                 750

Ser Cys Val Ala Leu Val Asn Gln Pro Pro His Ser Pro Trp Ser Phe
            755                 760                 765

Ser Arg Val
    770

<210> SEQ ID NO 48
<211> LENGTH: 2301
<212> TYPE: DNA
<213> ORGANISM: homo sapiens

<400> SEQUENCE: 48
atgcaaagca atgtcatca aaagggaaa acaaccaga cggagtgctt taaccatgtg      60
cggttcctgc agcggctcaa ttctacccac ctctatgcat gtgggactca cgccttccag    120
cccctctgtg cagccattga tgctgaggcc ttcaccttgc aaccagctt cgaggagggg     180 aaggagaagt gtccttatga cccagcccgt ggcttacag gcctcatcat tgatggaggc    240
ctctacacag ccactaggta tgaattccgg agcattcctg acatccgccg agccgccac    300 ccacactccc tgagaactga ggagacacca atgcattggc tcaatgatgc ggagtttgtg    360
ttctccgtcc tcgtgcggga gagcaaggcc agtgcagtgg gtgatgatga caaggtgtac    420
tacttcttca cggagcgtgc cactgaggag ggctctggca gcttcactca gagccgcagc    480
agtcaccgtg tggcccgtgt ggctcgygtc tgcaagggag acctgggagg aagaagatc    540 ctgcagaaga agtggacttc cttcctgaaa gcccgtctca tctgccacat tccactgtat    600
gagacactgc gtgggtctg cagcctggat gctgaaacct caagccgtac acacttctat    660
gcagccttca cgctgagcac acagtggaag acctggagg cctcagccat ctgccgctat    720
gacctggcag agatccaggc tgtcttttgca ggaccctata tggaatacca ggatggttcc    780
cggcgctggg tcgctatga gggtggggtg cctgagcccc ggcctggctc gtgtatcaca    840
gattcattgc gcagccaagg ctacaattca tcccaagact tgccatccct ggtcctggac    900
tttgtaaagt tgcacccact gatggctcgg cccgttgtgc ccacacgtgg acggcccctg    960
ctgctcaagc gcaacatacg ctacacacac cttacaggga cacctgtcac cacgcctgct   1020
ggacctacct atgacctgct ctttctgggc acagctgatg ctggatcca aaggccgta    1080 gtcctgggct ctgggatgca cattattgaa gagacacaag tgttcaggga gtcccagtct   1140
gtggaaaatc tagtcatctc tctattgcag cacagcctct atgtgggggc tcctagcgga   1200
gtcatccagc taccactctc cagctgctcc cgctaccgat cctgctatga ctgcatcttg   1260
```

-continued

```
gcccgagacc cctactgtgg ctgggaccct ggcacccatg cctgcgcagc agccaccacc      1320
atagccaaca ggacagcact gatacaggac atagagagag gaaatcgagg ctgtgagagc      1380
agcagggata cagggccacc accaccactg aagacccgct ctgtgctccg gggtgatgat      1440
gtcctcctgc cctgtgacca gccatccaac ctggcccggg ccttgtggct actcaatggg      1500
agcatgggcc tgagcgatgg gcaggggtggc taccgtgtgg gcgtggacgg gctgctggtt      1560
acagatgcac agcctgagca cagtggcaac tatggctgct atgccgagga aaatggcctc      1620
cgcaccctgc tggcctccta tagtctcaca gtccggccag ccactcctgc cccagctcca      1680
aaagcccctg ccacacctgg ggcacagctg gcacctgatg tgagactgct ctatgtgcta      1740
gccattgccg cgcttggtgg ccyctgcctc atcctggcct cctccctcct ctatgtggcc      1800
tgtctgcggg aaggcagacg agggcgccga cggaaatact cactgggtcg ggccagccgg      1860
gcaggaggat ctgcggtgca actgcagaca gtctcaggca gggctctgca ggtccatatg      1920
ggctcaatgt caccaccctc tgcatggccc tgtgtgctgg atggtcctga aaccagacaa      1980
gtcctctgcc agccacctaa gccctgcgta cattcacatg cacacatgga agaatgttta      2040
tcggctgggc tgcagtgccc ccaccctcac cttctcctgg tgcattcttg tttcatccct      2100
gcttctggac ttggggtacc ctcccaattg ccacatccta tctggtcctc ttccccagcc      2160
ccatgtggtg acctctttgt caagagcttg ggaacgggcc agcctgggga ggtaagactg      2220
catcactccc ctcctctccc ttcctgtgtg gcccttgtga atcagcctcc ccactctcct      2280
tggtcattct caagagtatg a                                                2301
```

<210> SEQ ID NO 49
<211> LENGTH: 766
<212> TYPE: PRT
<213> ORGANISM: homo sapiens

<400> SEQUENCE: 49

```
Met Gln Ser Lys Cys His Gln Lys Gly Lys Asn Asn Gln Thr Glu Cys
  1               5                  10                  15

Phe Asn His Val Arg Phe Leu Gln Arg Leu Asn Ser Thr His Leu Tyr
             20                  25                  30

Ala Cys Gly Thr His Ala Phe Gln Pro Leu Cys Ala Ala Ile Asp Ala
         35                  40                  45

Glu Ala Phe Thr Leu Pro Thr Ser Phe Glu Glu Gly Lys Glu Lys Cys
     50                  55                  60

Pro Tyr Asp Pro Ala Arg Gly Phe Thr Gly Leu Ile Ile Asp Gly Gly
 65                  70                  75                  80

Leu Tyr Thr Ala Thr Arg Tyr Glu Phe Arg Ser Ile Pro Asp Ile Arg
                 85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Val Arg Glu Ser
        115                 120                 125

Lys Ala Ser Ala Val Gly Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190
```

-continued

```
Leu Ile Cys His Ile Pro Leu Tyr Glu Thr Leu Arg Gly Val Cys Ser
        195                 200                 205

Leu Asp Ala Glu Thr Ser Ser Arg Thr His Phe Tyr Ala Ala Phe Thr
        210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
                    245                 250                 255

Gln Asp Gly Ser Arg Arg Trp Gly Arg Tyr Glu Gly Gly Val Pro Glu
                260                 265                 270

Pro Arg Pro Gly Ser Cys Ile Thr Asp Ser Leu Arg Ser Gln Gly Tyr
            275                 280                 285

Asn Ser Ser Gln Asp Leu Pro Ser Leu Val Leu Asp Phe Val Lys Leu
        290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                    325                 330                 335

Thr Thr Pro Ala Gly Pro Thr Tyr Asp Leu Leu Phe Leu Gly Thr Ala
                340                 345                 350

Asp Gly Trp Ile His Lys Ala Val Val Leu Gly Ser Gly Met His Ile
            355                 360                 365

Ile Glu Glu Thr Gln Val Phe Arg Glu Ser Gln Ser Val Glu Asn Leu
        370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                    405                 410                 415

Asp Cys Ile Leu Ala Arg Asp Pro Tyr Cys Gly Trp Asp Pro Gly Thr
                420                 425                 430

His Ala Cys Ala Ala Ala Thr Thr Ile Ala Asn Arg Thr Ala Leu Ile
            435                 440                 445

Gln Asp Ile Glu Arg Gly Asn Arg Gly Cys Glu Ser Ser Arg Asp Thr
        450                 455                 460

Gly Pro Pro Pro Leu Lys Thr Arg Ser Val Leu Arg Gly Asp Asp
465                 470                 475                 480

Val Leu Leu Pro Cys Asp Gln Pro Ser Asn Leu Ala Arg Ala Leu Trp
                    485                 490                 495

Leu Leu Asn Gly Ser Met Gly Leu Ser Asp Gly Gln Gly Gly Tyr Arg
                500                 505                 510

Val Gly Val Asp Gly Leu Leu Val Thr Asp Ala Gln Pro Glu His Ser
            515                 520                 525

Gly Asn Tyr Gly Cys Tyr Ala Glu Glu Asn Gly Leu Arg Thr Leu Leu
        530                 535                 540

Ala Ser Tyr Ser Leu Thr Val Arg Pro Ala Thr Pro Ala Pro Ala Pro
545                 550                 555                 560

Lys Ala Pro Ala Thr Pro Gly Ala Gln Leu Ala Pro Asp Val Arg Leu
                    565                 570                 575

Leu Tyr Val Leu Ala Ile Ala Ala Leu Gly Gly Leu Cys Leu Ile Leu
                580                 585                 590

Ala Ser Ser Leu Leu Tyr Val Ala Cys Leu Arg Glu Gly Arg Arg Gly
            595                 600                 605
```

```
Arg Arg Arg Lys Tyr Ser Leu Gly Arg Ala Ser Arg Ala Gly Gly Ser
    610                 615                 620

Ala Val Gln Leu Gln Thr Val Ser Gly Arg Ala Leu Gln Val His Met
625                 630                 635                 640

Gly Ser Met Ser Pro Ser Ala Trp Pro Cys Val Leu Asp Gly Pro
                645                 650                 655

Glu Thr Arg Gln Val Leu Cys Gln Pro Pro Lys Pro Cys Val His Ser
                660                 665                 670

His Ala His Met Glu Glu Cys Leu Ser Ala Gly Leu Gln Cys Pro His
            675                 680                 685

Pro His Leu Leu Val His Ser Cys Phe Ile Pro Ala Ser Gly Leu
690                 695                 700

Gly Val Pro Ser Gln Leu Pro His Pro Ile Trp Ser Ser Pro Ala
705                 710                 715                 720

Pro Cys Gly Asp Leu Phe Val Lys Ser Leu Gly Thr Gly Gln Pro Gly
                725                 730                 735

Glu Val Arg Leu His His Ser Pro Pro Leu Pro Ser Cys Val Ala Leu
                740                 745                 750

Val Asn Gln Pro Pro His Ser Pro Trp Ser Phe Ser Arg Val
            755                 760                 765

<210> SEQ ID NO 50
<211> LENGTH: 2951
<212> TYPE: DNA
<213> ORGANISM: homo sapiens

<400> SEQUENCE: 50
ccgcggagcc gcgcgtcgct gtctctatgg ccccggatcc gagcgcaaag aaaacggacc      60
tcagaaaacc aggactagct ctactgtcgg gggcagggtg accccatcag taacctacaa     120
cccctctaga acttcacaac tccctctcac catgggagttt gcatttgatg cagaaaggca     180
tgtgatccct ccctccttct gacctcttag ctggggattc catggccaca caaccctgtg     240
actccatgtc cccccgattc caggaccccc catggcccca tgattccttg actcctatga     300
ccttatgacc cctgaccttc caagtgactt ccttggactt tgaccccctgt gactgtgctt     360 cccattcccc gccccacaa cctgtgactc tggctcccctt tggggtcttt gttagtctgg     420
gcctccccag gaagatgtgg gggaggctct ggcccctcct cctcagcatc ctcacagcaa     480
ctgcagtccc aggaccctca ctgcggagac cgtctagaga actagatgcc accctcgga     540 tgaccatacc ctatgaagag ctctctggga cccggcactt caagggccaa gcccagaact     600
actcaacact gctgctggag gaggcctcag caaggctgct ggtgggagcc cgaggtgccc     660
tgttctctct cagtgccaac gacataggag atggggctca caaagagatc cactgggaag     720
cctccccaga gatgcaaagc aaatgtcatc aaaaagggaa aaacaaccag acggagtgct     780
ttaaccatgt gcggttcctg cagcggctca attctaccca cctctatgca tgtgggactc     840
acgccttcca gccccctctgt gcagccattg atgctgaggc cttcaccttg ccaaccagct     900
tcgaggaggg gaaggagaag tgtccttatg acccagcccg tggcttcaca ggcctcatca     960
ttgatggagg cctctacaca gccactaggt atgaattccg gagcattcct gacatccgcc    1020
ggagccgcca cccacactcc ctgagaactg aggagacacc aatgcattgg ctcaatgatg    1080
cggagtttgt gttctccgtc ctcgtgcggg agagcaaggc cagtgcagtg ggtgatgatg    1140
acaaggtgta ctacttcttc acggagcgtg ccactgagga gggctctggc agcttcactc    1200
agagccgcag cagtcaccgt gtggcccgtg tggctcgygt ctgcaaggga gacctgggag    1260
```

-continued

```
ggaagaagat cctgcagaag aagtggactt ccttcctgaa agcccgtctc atctgccaca    1320
ttccactgta tgagacactg cgtggggtct gcagcctgga tgctgaaacc tcaagccgta    1380
cacacttcta tgcagccttc acgctgagca cacagtggaa gaccctggag gcctcagcca    1440
tctgccgcta tgacctggca gagatccagg ctgtctttgc aggaccctat atggaatacc    1500
aggatggttc ccggcgctgg ggtcgctatg agggtggggt gcctgagccc cggcctggct    1560
cgtgtatcac agattcattg cgcagccaag gctacaattc atcccaagac ttgccatccc    1620
tggtcctgga ctttgtaaag ttgcacccac tgatggctcg gcccgttgtg cccacacgtg    1680
gacggcccct gctgctcaag cgcaacatac gctacacaca ccttacaggg acacctgtca    1740
ccacgcctgc tggacctacc tatgacctgc tctttctggg cacagctgat ggctggatcc    1800
acaaggccgt agtcctgggc tctgggatgc acattattga agagacacaa gtgttcaggg    1860
agtcccagtc tgtggaaaat ctagtcatct ctctattgca gcacagcctc tatgtggggg    1920
ctcctagcgg agtcatccag ctaccactct ccagctgctc ccgctaccga tcctgctatg    1980
actgcatctt ggcccgagac ccctactgtg gctgggaccc tggcacccat gcctgcgcag    2040
cagccaccac catagccaac aggacagcac tgatacagga catagagaga ggaaatcgag    2100
gctgtgagag cagcagggat acagggccac caccaccact gaagacccgc tctgtgctcc    2160
ggggtgatga tgtcctcctg ccctgtgacc agccatccaa cctggcccgg gccttgtggc    2220
tactcaatgg gagcatgggc ctgagcgatg ggcagggtgg ctaccgtgtg ggcgtggacg    2280
ggctgctggt tacagatgca cagcctgagc acagtggcaa ctatgctgc tatgccgagg     2340 aaaatggcct ccgcaccctg ctggcctcct atagtctcac agtccggcca gccactcctg    2400
ccccagctcc aaaagcccct gccacacctg gggcacagct ggcacctgat gtgagactgc    2460
tctatgtgct agccattgcc gcgcttggtg gccyctgcct catcctggcc tcctccctcc    2520
tctatgtggc ctgtctgcgg gaaggcagac gagggcgccg acggaaatac tcactgggtc    2580
gggccagccg ggcaggagga tctgcggtgc aactgcagac agtctcaggc cagtgtcctg    2640
gagaggaaga tgagggtgat gatgaggggg ctgggggcct ggagggcagc tgtctccaga    2700
tcatccctgg ggagggagcc ccagccccac caccccacc gccccaccg ccaccggctg      2760 agctgaccaa tggcttggtg gcactgccca gccggctgcg gaggatgaat ggcaatagct    2820
atgtgcttct gaggcagagc aacaatggag taccagcagg gccctgctcc ttcgccgagg    2880
aactcagccg catcctggaa aaaggaagc acacgcagct cgtggagcag ctagatgaga    2940
gctctgtctg a                                                         2951
```

HUMAN SEMAPHORIN HOMOLOGS AND POLYNUCLEOTIDES ENCODING THE SAME

The present application is a continuation of Ser. No. 09/854,845, filed on May 14, 2001 now U.S. Pat. No. 6,750,054 that claims the benefit of U.S. Provisional Application Nos. 60/205,274 and 60/208,893 which were filed on May 18, 2000 and Jun. 2, 2000, respectively. These U.S. Provisional Applications are herein incorporated by reference in their entirety.

1. INTRODUCTION

The present invention relates to the discovery, identification, and characterization of novel human polynucleotides encoding a protein that shares sequence similarity with mammalian semaphorin proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, the treatment of physiological disorders or diseases, and cosmetic or nutriceutical applications.

2. BACKGROUND OF THE INVENTION

Semaphorins are members of a superfamily of structurally related proteins that have been associated with axon guidance.

Their expression in non-neural tissues indicate that semaphorins can regulate biology in ways beyond axon guidance.

3. SUMMARY OF THE INVENTION

The present invention relates to the discovery, identification, and characterization of nucleotides that encode novel human proteins, and the corresponding amino acid sequences of these proteins. The novel human protein (NHP) described for the first time herein share structural similarity with mammalian semaphorins and particularly semaphorin G (SEQ ID NOS: 1–17) and semaphorin G (subclass 4) (SEQ ID NOS: 18–50).

The novel human nucleic acid sequences described herein, encode alternative proteins/open reading frames (ORFs) of 1049, 1093, 1034, 1078, 1151, 1136, 954, 939, 215, 496, 702, 697, 843, 838, 870, 865, 116, 397, 603, 598, 744, 739, 771, and 766 amino acids in length (see respectively SEQ ID NOS: 2, 4, 6, 8, 10, 12, 14, 16, 19, 21, 23, 25, 27, 29, 31, 33, 35, 37, 39, 41, 43, 45, 47, and 49).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–50 are "knocked-out" they provide a method of identifying phenotypic expression of the particular gene as well as a method of assigning function to previously unknown genes. To this end, several gene trapped knockout ES cells have been generated in murine homologs of the described NHPs. Additionally, the unique NHP sequences described in SEQ ID NOS:1–50 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences. SEQ ID NO:17 and SEQ ID NO:50 describe full length NHP ORFs and flanking sequences.

5. DETAILED DESCRIPTION OF THE INVENTION

The NHP, described for the first time herein, are novel proteins that are widely expressed. SEQ ID NO:1–17 are novel NHPs expressed in, inter alia, human cell lines, and human brain, pituitary, cerebellum, kidney, prostate, testis, thyroid, adrenal gland, pancreas, salivary gland, heart, uterus, cervix, pericardium, fetal kidney and fetal lung cells. SEQ ID NO:18–50 describe for the first time herein, are novel proteins that are expressed in, inter alia, human cell lines, human brain, fetal brain, lymph node, mammary gland, pituitary gland, placenta, prostate, kidney, thyroid, and umbilical vein endothelial cells.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent., as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–50 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–50, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–50 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–50.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ. ID NOS:1–50 provides detailed information about transcriptional changes involved in a specific pathway, potentially leading to the identification of novel components or gene functions that manifest themselves as novel phenotypes.

Probes consisting of sequences first disclosed in SEQ ID NOS:1–50 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–50 can be utilized in microarrays or other assay formats, to screen collections of genetic material from patients who have a particular medical condition. These investigations can also be carried out using the sequences first disclosed in SEQ ID NOS:1–50 in silico and by comparing previously collected-genetic databases and the disclosed sequences using computer software known to those in the art.

Thus the sequences first disclosed in SEQ ID NOS:1–50 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–50. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene-nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, example, obesity, behavioral disorders, colitis or spastic colon, high blood pressure, depression, connective tissue disorders, infertility, etc.) or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered human gene trapped sequences, and cDNA products isolated from human brain and kidney mRNA (SEQ ID NOS: 1–17) and human fetal brain and kidney libraries (Edge Biosystems, Gaithersburg, Md.)(SEQ ID NOS 18–50).

The described sequences share substantial structural similarity with a variety of proteins, including, but not limited to, semaphorins G and F. Because of their potential medical significance, semaphorin protein homologs have been subject to considerable scientific scrutiny as evidenced in U.S. Pat. Nos. 5,981,222 and 6,013,781, which are herein incorporated by reference, and which describe various applications, uses, and compositions in which the presently described NHPs can be advantageously applied.

The NHP sequences described in SEQ ID NOS: 1–17 can contain a variety of polymorphisms such as A–G transitions that can occur in the sequence regions represented by nucleotide positions nos. 100, 232, and 406 of, for example, SEQ ID NO:1 that can give rise to a N or D being present at corresponding amino acid positions 34, 78, and 136 of SEQ ID NO:2, and a polymorphism at nucleotide position 1974 of, for example, SEQ ID NO:1 which can give rise to GTG being present or deleted which causes an accompanying presence or deletion of a V at corresponding amino acid position 658, for example, of SEQ ID NO:2.

The NHP sequences described in SEQ ID NOS: 18–50 can also contain a couple of polymorphisms such as a translationally silent C–T transition that can occur in the sequence regions represented by nucleotide position no. 804 of, for example, SEQ ID NO: 28, and a T–C transition at nucleotide position 2060 of, for example, SEQ ID NO:28 which can give rise to a L or a P being present at corresponding amino acid position 687 of, for example, SEQ ID NO:29.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPs and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli*, *B. subtilis*) transformed with recombinant bacteriophage DNA, plasmid DNA or cosmid DNA expression vectors containing NHP nucleotide sequences; yeast (e.g., *Saccharomryces*, *Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes: A Practical Approach*, New, RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. application Ser. Nos. 60/111,701 and 60/056,713, both of which are herein incorporated by reference, for examples of such transducing sequences) to facilitate passage across cellular membranes if needed and can optionally be engineered to include nuclear localization sequences when desired.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising at a nucleotide sequence encoding an amino acid sequence drawn from the group consisting of SEQ ID NOS: 2, 4, 6, 8, 10, 12, 14, 16, 19, 21, 23, 25, 27, 29, 31, 33, 35, 37, 39, 41, 43, 45, 47, and 49.

2. An isolated nucleic acid molecule comprising a nucleotide sequence that:
   (a) encodes the amino acid sequence shown in SEQ ID NO: 4; and
   (b) hybridizes under stringent conditions to the nucleotide sequence of SEQ ID NO: 3 or the complement thereof.

3. An isolated nucleic acid molecule comprising a nucleotide sequence that encodes the amino acid sequence shown in SEQ ID NO:4.

4. An isolated nucleic acid molecule comprising a nucleotide sequence that encodes the amino acid sequence shown in SEQ ID NO:2.

5. An isolated nucleic acid molecule comprising a nucleotide sequence that encodes the amino acid sequence shown in SEQ ID NO:12.

6. An isolated nucleic acid molecule comprising a nucleotide sequence that:
   (a) encodes the amino acid sequence shown in SEQ ID NO: 29; and
   (b) hybridizes under stringent conditions to the nucleotide sequence of SEQ ID NO: 28 or the complement thereof.

7. An isolated nucleic acid molecule comprising a nucleotide sequence that encodes the amino acid sequence shown in SEQ ID NO: 29.

8. An isolated nucleic acid molecule comprising a nucleotide sequence that encodes the amino acid sequence shown in SEQ ID NO: 33.

9. An isolated nucleic acid molecule comprising a nucleotide sequence that encodes the amino acid sequence shown in SEQ ID NO: 25.

10. A purified polypeptide comprising the amino acid sequence of SEQ ID NO: 2.

* * * * *